(12) United States Patent
Harth et al.

(10) Patent No.: US 8,969,622 B2
(45) Date of Patent: Mar. 3, 2015

(54) DENDRITIC MOLECULAR INTRACELLULAR TRANSPORTERS AND METHODS OF MAKING AND USING SAME

(75) Inventors: Eva M. Harth, Nashville, TN (US); James E. Crowe, Jr., Nashville, TN (US); Kui Huang, Nashville, TN (US); Sharon K. Hamilton, Nashville, TN (US); Heidi E. Hamm, Nashville, TN (US); Bryan Voss, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1114 days.

(21) Appl. No.: 11/844,353

(22) Filed: Aug. 23, 2007

(65) Prior Publication Data

US 2008/0221043 A1 Sep. 11, 2008

Related U.S. Application Data

(60) Provisional application No. 60/839,625, filed on Aug. 23, 2006, provisional application No. 60/869,878, filed on Dec. 13, 2006.

(51) Int. Cl.
| | |
|---|---|
| *A61K 31/00* | (2006.01) |
| *A61K 47/48* | (2006.01) |
| *A61K 49/00* | (2006.01) |
| *A01N 61/00* | (2006.01) |
| *C07C 277/00* | (2006.01) |
| *C07C 279/00* | (2006.01) |
| *C07D 311/90* | (2006.01) |

(52) U.S. Cl.
CPC ....... *A61K 47/48169* (2013.01); *A61K 49/0054* (2013.01); *A61K 49/0052* (2013.01); *C07D 311/90* (2013.01); *Y10S 977/754* (2013.01)
USPC .................. 564/236; 514/1; 514/1.1; 436/56; 977/754; 424/78.27

(58) Field of Classification Search
None
See application file for complete search history.

(56) References Cited

U.S. PATENT DOCUMENTS

| | | | |
|---|---|---|---|
| 4,767,872 A | 8/1988 | Doutheau et al. | 549/551 |
| 5,543,158 A | 8/1996 | Gref et al. | 424/501 |
| 6,048,736 A | 4/2000 | Kosack | 436/536 |
| 6,196,993 B1 | 3/2001 | Cohan et al. | 604/890.1 |
| 7,015,286 B2 | 3/2006 | Heilmann et al. | 525/191 |
| 7,935,782 B2 | 5/2011 | Harth et al. | 528/403 |
| 2002/0123609 A1* | 9/2002 | Frechet et al. | 528/403 |
| 2003/0050426 A1 | 3/2003 | Shastri | 528/92 |
| 2006/0216265 A1* | 9/2006 | Goodman et al. | 424/78.27 |
| 2008/0221043 A1 | 9/2008 | Harth et al. | 424/78.27 |
| 2008/0233053 A1 | 9/2008 | Gross et al. | 424/45 |
| 2009/0054619 A1 | 2/2009 | Baker et al. | 528/354 |
| 2009/0163476 A1 | 6/2009 | Milburn et al. | 548/400 |
| 2009/0306335 A1 | 12/2009 | Harth et al. | 528/403 |
| 2010/0041859 A1* | 2/2010 | Newkome et al. | 528/332 |
| 2011/0274620 A1 | 11/2011 | Harth et al. | 424/489 |

FOREIGN PATENT DOCUMENTS

| | | |
|---|---|---|
| EP | 2209496 | 7/2010 |
| WO | WO 2004072153 A1 * | 8/2004 |
| WO | PCT/US2007/018645 | 8/2007 |
| WO | WO 2008/024435 | 2/2008 |
| WO | PCT/US2008/082529 | 11/2008 |
| WO | WO 2009/061854 | 5/2009 |
| WO | WO 2011/082432 | 7/2011 |

OTHER PUBLICATIONS

Newkome et al. Chemistry: a European Journal 2006 12:3726-3734; available online Mar. 3, 2006.*
Sun et al. Organic Letters 2005 7:3845-3848; published online Aug. 11, 2005.*
Gupta et al. Advanced Drug Delivery Reviews 2005 57:637-651.*
Brinkley Perspectives in Bioconjugate Chemistry ed. Meares. American Chemical Society: Washington DC 1993 59-70.*
Wu et al. Bioconjugate Chemistry 2004 15:185-194.*
Hart et al. Chemical Communications 2003 322-323.*
Mitchell et al. Journal of Peptide Research 2000 56:318-325.*
Croce et al., "Approaches in the development of 3-D nanoscopic, multimodal vectors," E. Poly.Prep, ACS Fall 2005.

(Continued)

*Primary Examiner* — Juliet Switzer
*Assistant Examiner* — Caralynne Helm
(74) *Attorney, Agent, or Firm* — Ballard Spahr LLP

(57) ABSTRACT

In accordance with the purpose(s) of the invention, as embodied and broadly described herein, the invention, in one aspect, relates to compounds comprising the structure:

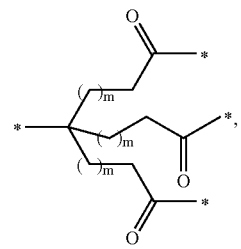

and at least one guanidinium residue, wherein m is zero or a positive integer. Also disclosed are methods of preparing the disclosed compounds. Also disclosed are methods of intracellular delivery comprising administering the disclosed compounds and compositions to a subject. Also disclosed are pharmaceutical compositions comprising a therapeutically effective amount of one or more compounds or compositions of the invention and a pharmaceutically acceptable carrier. This abstract is intended as a scanning tool for purposes of searching in the particular art and is not intended to be limiting of the present invention.

15 Claims, 26 Drawing Sheets

(56) References Cited

OTHER PUBLICATIONS

Chino et al., "Synthesis of a Poly (vinyl ether) containing a benzocyclobutane moiety and its reaction with dienophiles," *J. Poly. Sci. (A): Polymer Chemistry* 37:59-67 (1999).
Chung et al. "Dendritic Oligoguanidines as Intracellular Translocators," *Biopolymers (Pept. Sci.)* 76:83-96 (2004).
Coupade et al. "Novel human-derived cell-penetrating peptides for specific subcellular delivery of therapeutic biomolecules," *Biochem. J.* 390:407-418 (2005).
Feichtinger et al., "Triurethane-protected guanidines and triflyldiurethane-protected guanidines: New reagents for guanidinylation reactions," *J. Org. Chem.* 63:8432-8439 (1998).
Fukati, S., "Membrane-permeable arginine-rich peptides and the translocation mechanisms," *Adv. Drug Del. Rev.* 57:547-558 (2005).
Futaki et al., "Tranlocation of branched-chain, arginine peptides through cell membranes: Flexibility in the spatial disposition of positive charges in membrane-permeable peptides," *Biochemistry* 41:7925-7930 (2002).
Ghoroghchian et al., "Near-infrared-emissive polymersomes: Self-assembled soft matter for in vivo optical imaging," *PNAS*, 102(8):2922-2927 (2005).
Gillies et al., "Dendrimers and dendritic polymers in drug delivery," *J. Drug Discov. Today* 10:35-43 (2005).
Hallahan et al., "Integrin-mediated targeting of drug delivery to irradiated tumor blood vessels," *J. Cancer Cell*. 3:63-74 (2003).
Harth et al., "A facile approach to architecturally defined nanoparticles via intramolecular chain collapse," *J. Am. Chem. Soc.* 124:8653-8660 (2002).
Hatanaka et al., "Synthesis of new heparinoids with high anticoagulant activity," *J. Med. Chem.* 30:810-814 (1987).
Huang et al., "Nanocages derived from shell cross-linked micelle templates," *J. Am. Chem. Soc.* 121:3805-3806 (1999).
Huang et al. "Dendritic molecular transporters provide control of delivery to intracellular compartments." *Bioconjugate Chem.* 18(2):403-409 (2007).
Hawker et al., "New polymer synthesis by nitroxide mediated living radical polymerization," *Chem. Rev.* 101(12):3661-3688 (2001).
Kearsey, J. "Strategies for intracellular drug delivery." The Drug Delivery Companies Report Autumn/ Winter. 2004 Pharmaventures Ltd.
Lee et al., "Designed dendrimers for biological applications," *Nat. Biotechnol*. 23:1517-1526 (2005).
Lu et al., "Effects of molecular weight on the structure of poly(phenylene sulfide) crystallized at low temperature," *Macromolecules* 30(20):6243-6250 (1997).
Lui et al., "Designing dendrimers for drug delivery," *J. Pharm. Sci. Technol. Today* 2:393-401 (1999).
McGehee et al., "Semiconducting (conjugated) polymers as materials for solid-state lasers," *Adv. Materials* 12(22):1655-1668 (2000).
Newkome et al., "Cascade polymers: Synthesis and characterization of one-directional arborols based on adamantine," *J. Org. Chem.*, 56:7162-7167 (1991).
Somarajan et al., "Controlled electrophoretic deposition of uniquely nanostructured star polymer films," *J. Phys. Chem.* 112:23-28 (2008).
Smulders et al., "Seeded emulsion polymerization of block copolymer core-shell nanoparticles with controlled particle size and molecular weight distribution using xanthate-based RAFT polymerization," *Macromolecules* 34:4474-4483 (2004).
Vivès et al., "A truncated HIV-1 tat protein basic domain rapidly translocates through the plasma membrane and accumulates in the cell nucleus," *J. Chem.* 272(25):16010-16017 (1997).
Wender et al., "Dendrimeric molecular transporters: Synthesis and evaluation of tunable polyguanidino dendrimers that facilitate cellular uptake," *Org. Lett.* 7(22):4815-4818 (2005).
Wender et al., "The design, synthesis, and evaluation of molecules that enable or enhance cellular uptake: Peptoid molecular transporters," *Proc. Natl. Acad. Sci.* 97:13003-13008 (2000).
Wu et al., "Preparation and encapsulation of highly fluorescent conjugated polymer nanoparticles," *Langmuir*, 22:2956-2960 (2006).
Zhao et al., "Intracellular cargo delivery using tat peptide and derivatives," *Med. Res. Rev.* 24:112 (2004).
U.S. Appl. No. 12/265,701, filed Nov. 5, 2008, Harth, Office Action dated Jan. 8, 2010, Jan. 8, 2010.
U.S. Appl. No. 12/265,701, filed Nov. 5, 2008, Harth, Response to Office Action dated Jan. 8, 2010, Jul. 8, 2010.
U.S. Appl. No. 12/265,701, filed Nov. 5, 2008, Harth, Examiner Interview Summary, Sep. 23, 2010.
U.S. Appl. No. 12/265,701, filed Nov. 5, 2008, Harth, Notice of Allowance Sep. 23, 2010.
Burke et al., "RenaGel, a novel calcium- and aluminium-free phosphate binder, inhibits phosphate absorption in normal volunteers," *Nephrol. Dial. Transplant*., 12(8):1640-1644 (1997).
Cardona et al., "Dendrimers functionalized with a single fluorescent dansyl group attached "off center": Synthesis and photophysical studies," *Journal of the American Chemical Society*, Jul. 2000, 122:6139-6144.
Hamilton et al., "Effective Delivery of IgG-antibodies into infected cells via dendritic molecular transporter conjugate IgGMT," *Molecular Biosystems*, 4 (12): 1209-1211 (2008).
Hans et al., "Biodegradable nanoparticles for drug delivery and targeting," *Curr. Opin. Solid State Mater. Sci.*, 6:319-327 (2002).
Kallinteri et al., "Novel functionalized biodegradable polymers for nanoparticle drug delivery systems," *Biomacromolecules* 6:1885-1894 (2005).
Kricheldorf et al., "Polylactones 36. Macrocyclic Polymerization of Lactides with Cyclic Bu2Sn Initiators Derived from 1,2-Ethanediol, 2-Mercaptoethanol, and 1,2-Dimercaptoethane," *Macromolecules*, 25:1375-1381 (1996).
Kumar, et al., "Preparation and characterization of cationic PLGA nanospheres as DNA carriers," *Biomaterials*, 25:1771-1777 (2004).
Latere et al., "2-Oxepane-1,5-dione : a precursor of a novel class of versatile semicrystalline biodegradable (co)polyesters," *Macromolecules*, 35:7857-7859 (2002).
Lee et al., "Formation of rotaxane dendrimers by supramolecular click chemistry," *Bull. Korean Chem. Soc.*, 28(10):1837-1940 (2007).
Lubetkin et al., "A novel route for the preparation of narrow particle size distribution emulsions and microcapsules," *Pesti. Sci.*, 55:1123-1125 (1999).
Mecerreyes, et al., "Ring-opening polymerization of 6-hydroxynon-8-enoic acid lactone: novel biodegradable copolymers containing allyl pendent groups," *J. Polym. Sci. Part A: Polym. Chem.* 38:870-875 (2000).
Möller et al., "Sn(OTf)2 and Sc(OTf)3: Efficient and versatile catalysts for the controlled polymerization of lactones ," *J. Polym. Sci. Part A:Polym Chem.*, 38:2067-2074 (2000).
Newkome et al., "Synthesis of benzyl-terminated dendrons for use in high-resolution capillary gas chromatography tetrahedron," *Tetrahedron Letters 2001*, 42:7537-7541.
Parrish et al., "PEG- and peptide-grafted aliphatic polyesters by click chemistry," *J. Am. Chem. Soc.*, 127:7404-7410 (2005).
Parrish et al., "Functional polyesters prepared by polymerization of α-allyl (valerolactone) and its copolymerization with ε-caprolactone and δ- valerolactone," *J. Polym. Sci.: Part A: Polym Chem*, 40:1983-1990 (2002).
Riva et al., Functionalization of poly(ε-caprolactone) by pendant hydroxyl, carboxylic acid and epoxide groups by atom transfer radical addition, *Polymer*, 46:8511-8518 (2005).
Sasatsu et al., "In vitro and in vivo characterization of nanoparticles made of MeO-PEG amine/PLA block copolymer and PLA," *Inter. J. Pharm.*, 317:167-174 (2006).
Van Horn et al., "Toward Cross-linked degradable polyester materials: investigations into the compatibility and use of reductive amination chemistry for cross-linking," *Macromolecules*, 40(5):1480-1488 (2007).
Yadav et al., "Synthesis of biologically active compounds of agricultural interest," *Pure and Appl. Chem*, 62:7:1333-1338 (1990).
Zweers et al., "Biodegradable nanoparticles for local drug delivery," *J. Controlled Release*, 87:252-254 (2003).

(56) References Cited

OTHER PUBLICATIONS

European Search Opinion issued Jul. 4, 2012 by the European Patent Office for Application No. 20080846997 filed Nov. 5, 2008 (Applicant—Vanderbilt University // Inventor—Harth, et al.; (pp. 1-3).
Preliminary Amendment filed May 27, 2010 to the European Patent Office for Application No. 20080846997 filed Nov. 5, 2008 (Applicant—Vanderbilt University // Inventor—Harth, et al.; (pp. 1-145).
Supplemental European Search Report issued Jul. 4, 2012 by the European Patent Office for Application No. 20080846997 filed Nov. 5, 2008 (Applicant—Vanderbilt University // Inventor—Harth, et al.; (pp. 1-3).
Amendments After Notice of Allowance filed Dec. 9, 2010 to the United States Patent and Trademark Office for U.S. Appl. No. 12/265,701, filed Nov. 5, 2008 (Applicant—Vanderbilt University // Inventor—Harth, et al.; (pp. 1-2).
Notice of Allowance and Fees Due issued Dec. 16, 2010 by the United States Patent and Trademark Office for U.S. Appl. No. 12/265,701, filed Nov. 5, 2008 (Applicant—Vanderbilt University // Inventor—Harth, et al.; (pp. 1-2).
Notice of Allowance issued Jan. 5, 2011 by the United States Patent and Trademark Office for U.S. Appl. No. 12/265,701, filed Nov. 5, 2008 (Applicant—Vanderbilt University // Inventor—Harth, et al.; (pp. 1-3).
Notice to File Corrected Application Papers issued Nov. 3, 2010 by the United States Patent and Trademark Office for U.S. Appl. No. 12/265,701, filed Nov. 5, 2008 (Applicant—Vanderbilt University // Inventor—Harth, et al.; (pp. 1-4).
Response to Amendments issued Dec. 30, 2010 by the United States Patent and Trademark Office for U.S. Appl. No. 12/265,701, filed Nov. 5, 2008 (Applicant—Vanderbilt University // Inventor—Harth, et al.; (pp. 1-2).
Response to Notice to File Corrected Application filed Dec. 29, 2010 to the United States Patent and Trademark Office for U.S. Appl. No. 12/265,701, filed Nov. 5, 2008 (Applicant—Vanderbilt University // Inventor—Harth, et al.; (pp. 1-15).
Response to Notice to File Corrected Application filed Mar. 7, 2011 to the United States Patent and Trademark Office for U.S. Appl. No. 12/265,701, filed Nov. 5, 2008 (Applicant—Vanderbilt University // Inventor—Harth, et al.; (pp. 1-25).
Non-final Office Action issued May 30, 2012 by the United States Patent and Trademark Office for U.S. Appl. No. 12/953,173, filed Nov. 23, 2010 (Applicant—Vanderbilt University // Inventor—Harth, et al.; (pp. 1-9).
Response to Restriction Requirement filed May 14, 2012 to the United States Patent and Trademark Office for U.S. Appl. No. 12/953,173, filed Nov. 23, 2010 (Applicant—Vanderbilt University // Inventor—Harth, et al.; (pp. 1-5).
Restriction/Election Requirement issued Dec. 14, 2011 by the United States Patent and Trademark Office for U.S. Appl. No. 12/953,173, filed Nov. 23, 2010 (Applicant—Vanderbilt University // Inventor—Harth, et al.; (pp. 1-11).
International Preliminary Report on Patentability issued Jul. 4, 2012 by the International Searching Authority for Application PCT/US2011/020148 filed Jan. 4, 2011(Applicant—Vanderbilt University // Inventor—Harth, et al.; (pp. 1-5).
International Search Report issued Apr. 6, 2011 by the International Searching Authority for Application PCT/US2011/020148 filed Jan. 4, 2011(Applicant—Vanderbilt University // Inventor—Harth, et al.; (pp. 1-1).
Written Opinion issued Apr. 6, 2011 by the International Searching Authority for Application PCT/US2011/020148 filed Jan. 4, 2011(Applicant—Vanderbilt University // Inventor—Harth, et al.; (pp. 1-4).
Applicant Response to Pre-Exam Formalities filed Aug. 27, 2010 to the United States Patent and Trademark Office for U.S. Appl. No. 12/651,710, filed Jan. 4, 2010 (Applicant—Vanderbilt University // Inventor—Harth, et al.; (pp. 1-526).

Final Rejection issued Jan. 14, 2013 by the United States Patent and Trademark Office for U.S. Appl. No. 12/651,710, filed Jan. 4, 2010 (Applicant—Vanderbilt University // Inventor—Harth, et al.; (pp. 1-7).
Non-Final Office Action issued Apr. 23, 2012 by the United States Patent and Trademark Office for U.S. Appl. No. 12/651,710, filed Jan. 4, 2010 (Applicant—Vanderbilt University // Inventor—Harth, et al.; (pp. 1-11).
Notice of Abandonment issued Sep. 16, 2010 by the United States Patent and Trademark Office for U.S. Appl. No. 12/651,710, filed Jan. 4, 2010 (Applicant—Vanderbilt University // Inventor—Harth, et al.; (pp. 1-2).
Notice to File Corrective Application Papers issued Jan. 21, 2011 by the United States Patent and Trademark Office for U.S. Appl. No. 12/651,710, filed Jan. 4, 2010 (Applicant—Vanderbilt University // Inventor—Harth, et al.; (pp. 1-2).
Petition to Revive Application Granted issued Jan. 3, 2011 by the United States Patent and Trademark Office for U.S. Appl. No. 12/651,710, filed Jan. 4, 2010 (Applicant—Vanderbilt University // Inventor—Harth, et al.; (pp. 1-5).
Request for Reconsideration of the Holding of Abandonment filed Oct. 25, 2010 to the United States Patent and Trademark Office for U.S. Appl. No. 12/651,710, filed Jan. 4, 2010 (Applicant—Vanderbilt University // Inventor—Harth, et al.; (pp. 1-541).
Requirement for Restriction/Election issued Nov. 16, 2011 by the United States Patent and Trademark Office for U.S. Appl. No. 12/651,710, filed Jan. 4, 2010 (Applicant—Vanderbilt University // Inventor—Harth, et al.; (pp. 1-10).
Response to Notice to File Corrective Application Papers filed Jul. 21, 2011 to the United States Patent and Trademark Office for U.S. Appl. No. 12/651,710, filed Jan. 4, 2010 (Applicant—Vanderbilt University // Inventor—Harth, et al.; (pp. 1-4).
Response to Office Action filed Oct. 23, 2012 to the United States Patent and Trademark Office for U.S. Appl. No. 12/651,710, filed Jan. 4, 2010 (Applicant—Vanderbilt University // Inventor—Harth, et al.; (pp. 1-11).
Response to Restriction/Election filed Feb. 16, 2012 to the United States Patent and Trademark Office for U.S. Appl. No. 12/651,710, filed Jan. 4, 2010 (Applicant—Vanderbilt University // Inventor—Harth, et al.; (pp. 1-13).
Preliminary Amendment filed Jul. 5, 2012 to the United States Patent and Trademark Office for U.S. Appl. No. 13/520,775, filed Jan. 4, 2011 (Applicant—Vanderbilt University // Inventor—Harth, et al.; (pp. 1-4).
Akers, HJ, "Ocular bioavailability of topically applied ophthalmic drugs," *Am Pharm*, 1983, NS23(1): pp. 33-36.
Bourges et al., "Intraocular implants for extended drug delivery: Therapeutic application," *Advanced Drug Deliver Review*, 2006, 58(11): pp. 1182-1202.
Gross et al., "Retinal ganglion cell dysfunction induced by Hypoxia and Glutamate: Potential neuroprotective effects of β-blockers," *Survey of Ophthalamology*, 1999, 43(S1): pp. S162-S170.
Hermanson, Greg. *Bioconjugate Techniques* 1996, pp. 220-221.
Konstas et al., "Twenty-four hour control of intraocular pressure with dorzolamide and timolol maleate in exfoliation and primary open-angle glaucoma," *Eye*, 2000, 14: pp. 73-77.
Taniguchi, et al., "A chemoselective approach to grafting biodegradable polyesters," *Macromolecules*, 2005, 38(2): pp. 216-219.
Song et al. Journal of Controlled Release; 413(2-3), pp. 197-212, 1997.
Non-Final Rejection issued Sep. 26, 2014 by U.S. Appl. No. 12/651,710, filed Jan. 4, 2010 and published as US 2011-0274620 A1 on Nov. 10, 2011 (Applicant—Vanderbilt University // Inventor—Harth, et al.) (15 pages).
Response to Election Under Restriction Requirement filed Dec. 1, 2014 to U.S. Appl. No. 13/520,775, filed Jan. 28, 2013 and published as US 2013-0142733 A1 on Jun. 6, 2013 (Applicant—Vanderbilt University // Inventor—Harth, et al.) (10 pages).
Restriction Requirement issued Oct. 1, 2014 to U.S. Appl. No. 13/520,775, filed Jan. 28, 2013 and published as US 2013-0142733 A1 on Jun. 6, 2013 (Applicant—Vanderbilt University // Inventor—Huth, et al.) (10 pages).

* cited by examiner

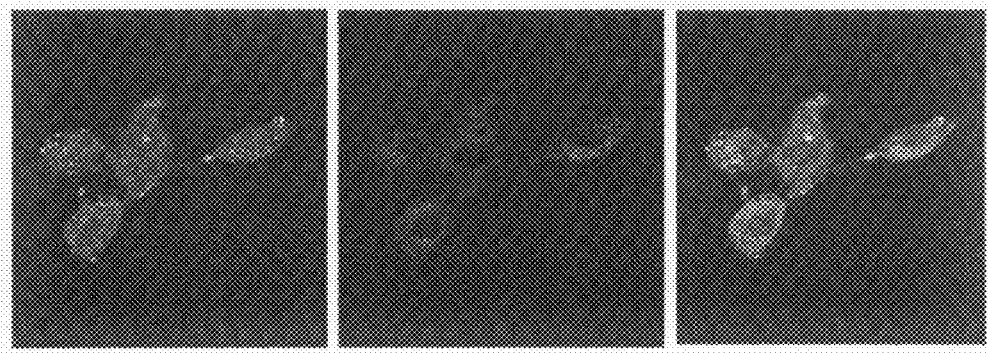
FIGURE 34
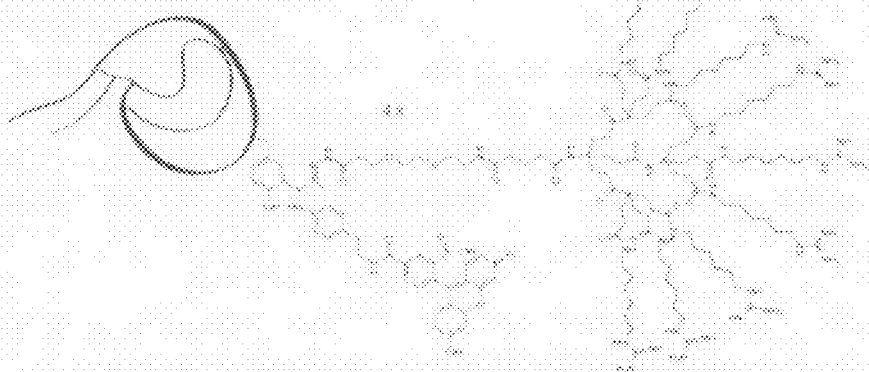
Aprotinin-Fluorophore-Transporter Conjugate
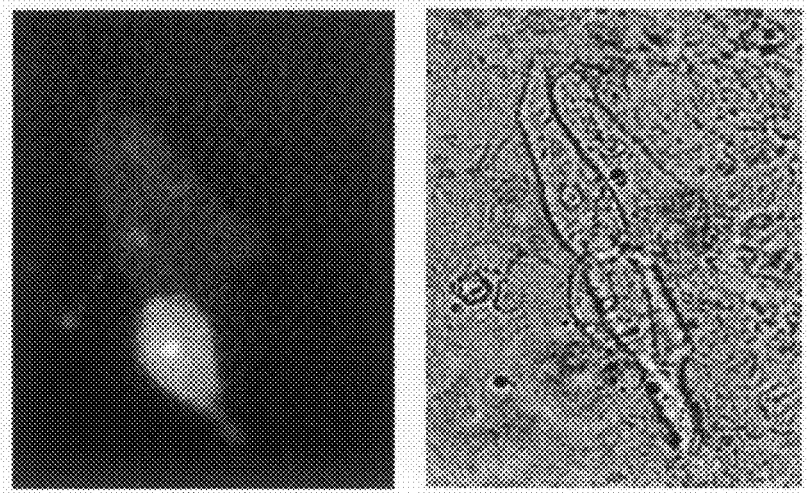
FIGURE 35

DENDRITIC MOLECULAR INTRACELLULAR TRANSPORTERS AND METHODS OF MAKING AND USING SAME

CROSS-REFERENCE TO RELATED APPLICATIONS

This application claims the benefit of, U.S. Application No. 60/839,625, filed Aug. 23, 2006, and U.S. Application No. 60/869,878, filed Dec. 13, 2006, which are hereby incorporated herein by reference in their entireties.

ACKNOWLEDGEMENT

This invention was made with government support under Grants NIH EY06062, EY10291, and HL84388, awarded by the National Institutes of Health. The government has certain rights in the invention.

BACKGROUND

The development of novel approaches that allow or enhance cellular uptake of a variety of physiologically and therapeutically active agents relies on the elucidation of new molecular tranporter/translocator molecules and methodologies. [Fukati, S. Adv. Drug Del. Rev. 2005, 57, 547.; Langel, Ü. Cell-Penetrating Peptides; CRC Press: Boca Raton, Fla., 2002.] In the past several years, strategies to overcome the limiting uptake of the plasma membrane have included peptide vectors, such as Tat peptide and other various arginine rich oligopeptides. [Wender, P. A.; Mitchell, D. J.; Pattabiraman, K.; Pelkey, E. T.; Steinman, L.; Rothbard, J. B. Proc. Natl. Acad. Sci. 2000, 97, 13003.; Zhao, M.; Weissleder, R. Med. Res. Rev. 2004, 24, 1.] Arginine-rich HIV-Tat peptide ($R_{49}$KKRRQRRR$_{57}$) and its derivatives have been given much attention; primarily because of their high efficiency, short sequence, and capabilities of transporting various types of molecular structures, such as small molecular weight compounds, oligonucleotides, magnetic beads, plasmid DNA, and even a full 129 kDa protein across the membranes of most cell types. [Wender, P. A.; Mitchell, D. J.; Pattabiraman, K.; Pelkey, E. T.; Steinman, L.; Rothbard, J. B. Proc. Natl. Acad. Sci. 2000, 97, 13003.; Zhao, M.; Weissleder, R. Med. Res. Rev. 2004, 24, 1.] Studies of short oligomers composed of six to fifteen contiguous arginine residues as well as nonlinear branched peptides containing eight arginine units were shown to cross cell membranes efficiently and outperformed Tat in uptake assays. [Wender, P. A.; Kreider, E.; Pelkey, E. T.; Steinman, L.; Rothbard, J. B.; VanDeusen, C. L. Org. Lett. 2005, 7, 4815.] Although the exact translocation mechanism remains to be understood, it is known that the high arginine content plays an important role for translocation. [Fukati, S. Adv. Drug Del. Rev. 2005, 57, 547.] However, these peptide or peptoid-based molecular transporters are limited by high cost, scalability, solubility, and stability. Therefore, there is significant need for the development of new cell permeable transporter molecules with membrane translocating activity. Efficient intracellular delivery can avoid non-specific effects, reduce toxicity, and allow a reduction in dosage levels. In particular, sufficiently efficient technologies can deliver drugs to the cytoplasm or the nucleus to better target more efficient novel technologies through accumulation of the therapeutic in subcellular locations.

SUMMARY

In accordance with the purpose(s) of the invention, as embodied and broadly described herein, the invention, in one aspect, relates to compounds comprising the structure:

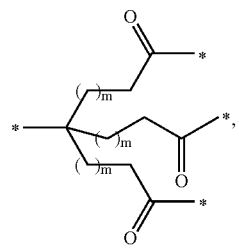

and at least one guanidinium residue, wherein m is zero or a positive integer.

In a further aspect, the invention relates to methods of preparing compounds having the structure:

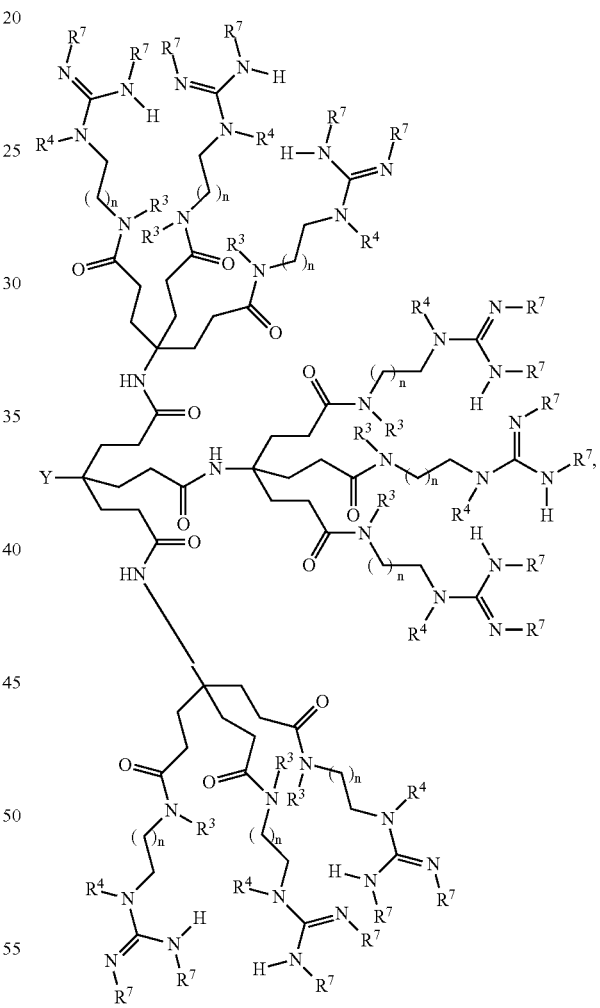

wherein n is an integer from 1 to 9, wherein $R^3$ is hydrogen or alkyl, wherein $R^4$ and $R^7$ are, independently, hydrogen, alkyloxycarbonyl, alkyl, or acyl; wherein $R^7$ is hydrogen, alkyl, or acyl; wherein Y comprises a nitro group, an amide group, azide group, or an alkyloxycarbonyl protected amine group, the method comprising the steps of: providing a first compound comprising the structure:

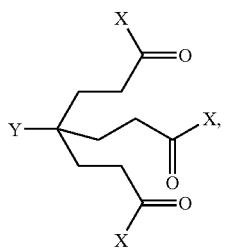

wherein X comprises OH, halogen, or OC(O)-alkyl; coupling the first compound with at least about three molar equivalents of a second compound comprising the structure:

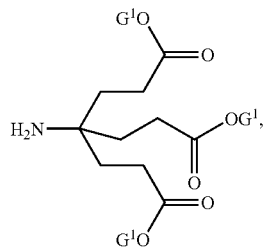

wherein $G^1$ is an ester-protecting group; removing the ester-protecting group; reacting the product of step (c) with at least about three molar equivalents of a third compound comprising the structure:

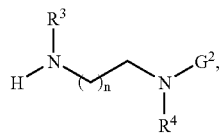

wherein $G^2$ is an amine-protecting group; removing the amine-protecting group; and functionalizing the product of step (e) with at least three molar equivalents of a guanidine-providing agent.

In a yet further aspect, the invention relates to intracellular delivery compositions comprising the general structure P-L-B-F, wherein P is payload moiety; wherein L is a linking moiety comprising the structure:

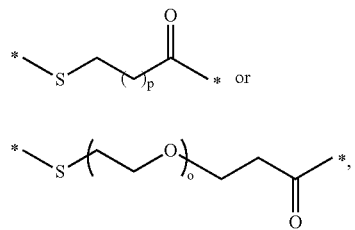

wherein o and p are, independently, zero or a positive integer; wherein B is a branching moiety comprising the structure:

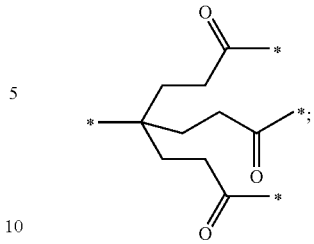

and wherein F is a functional moiety comprising at least one guanidinium residue.

In a further aspect, the invention relates to compounds comprising the structure:

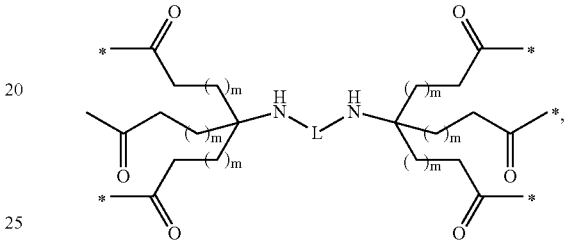

wherein each m is independently zero or a positive integer, and wherein L is a linking moiety comprising optionally substituted alkyl, optionally substituted alkoxyl, optionally substituted heteroalkyl, or optionally substituted heteroaryl.

In a further aspect, the invention relates to a compound comprising the structure:

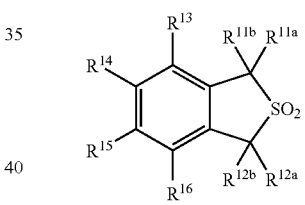

wherein $R^{11a}$, $R^{11b}$, $R^{12a}$, and $R^{12b}$ are, independently, hydrogen, alkyl, alkoxyl, acyl, or carbonyl; wherein $R^{13}$, $R^{14}$, $R^{15}$, and $R^{16}$ are, independently, hydrogen, alkyl, alkenyl, alkynyl, alkoxyl, acyl, or carbonyl, with the proviso that at least one of $R^{13}$, $R^{14}$, $R^{15}$, or $R^{16}$ is a polymerizable group; and wherein the compound eliminates $SO_2$ to form a reactive intermediate at a reaction temperature. In a further aspect, at least one of $R^{13}$, $R^{14}$, $R^{15}$, and $R^{16}$ is alkenyl or alkynyl. In a yet further aspect, $R^{14}$ is vinyl. In a still further aspect, $R^{11a}$, $R^{11b}$, $R^{12a}$, and $R^{12b}$ are hydrogen. In a still further aspect, $R^{14}$ is vinyl and $R^{13}$, $R^{15}$, and $R^{16}$ are hydrogen.

In a further aspect, the invention relates to a compound comprising the structure:

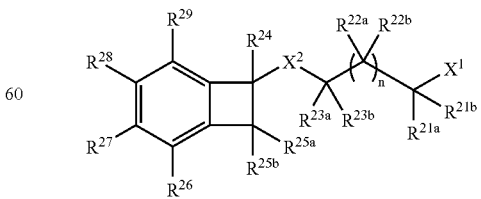

wherein $X^1$ is hydroxyl, primary amino, secondary amino, tertiary amino, thiol, or carboxyl; wherein n is zero or a positive integer; wherein $R^{21a}$, $R^{21b}$, $R^{22a}$, and $R^{22b}$, $R^{23a}$, and $R^{23b}$ are, independently, hydrogen, alkyl, alkoxyl, acyl, or carbonyl; wherein $X^2$ is oxygen, secondary nitrogen, tertiary nitrogen, or sulfur; wherein $R^{24}$, $R^{25a}$, $R^{25b}$, $R^{26}$, $R^{27}$, $R^{28}$, and $R^{29}$ are, independently, hydrogen, alkyl, alkenyl, alkynyl, alkoxyl, acyl, or carbonyl; and wherein the cyclobutane ring undergoes ring opening to form a reactive intermediate at a reaction temperature.

In a further aspect, the invention relates to a method of nanoparticle formation comprising the steps of providing a reactor capable of imparting a stimulus and adding to the reactor a block copolymer comprising at least two reactive residues, thereby imparting the stimulus on at least a portion of the block copolymer; wherein the at least two reactive residues form reactive intermediates upon exposure to the stimulus, and wherein the reactive intermediates are capable of undergoing a bond-forming reaction.

In a further aspect, the invention relates to a block copolymer comprising the structure A-B, wherein A is an oligomeric block comprising at least two reactive residues, and wherein B is a block comprising at least one functional moiety.

In a yet further aspect, the invention relates to methods of intracellular delivery comprising administering an effective amount of one or more compounds of the invention or one or more compositions of the invention to a subject.

In a yet further aspect, the invention relates to pharmaceutical compositions comprising a therapeutically effective amount of one or more compounds of the invention or one or more compositions of the invention and a pharmaceutically acceptable carrier for administration in a mammal.

In a yet further aspect, the invention relates to the products of the disclosed methods.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several embodiments and together with the description serve to explain the principles of the invention.

FIG. 25 shows a schematic illustrating conjugation of the disclosed dendrimeric materials with the disclosed organic quantum dot materials (conjugation with cleavable linker).

FIG. 34 shows micrographs of HeLa cells exposed 20 µM FD-2 for 1 h, fixed with 3.3% paraformaldehyde, stained with 100 nM Mitotracker® Red 580 FM. The illuminated regions show cell penetration (left), mitochondria location (center), and overlap (right).

DETAILED DESCRIPTION

Figure 1:
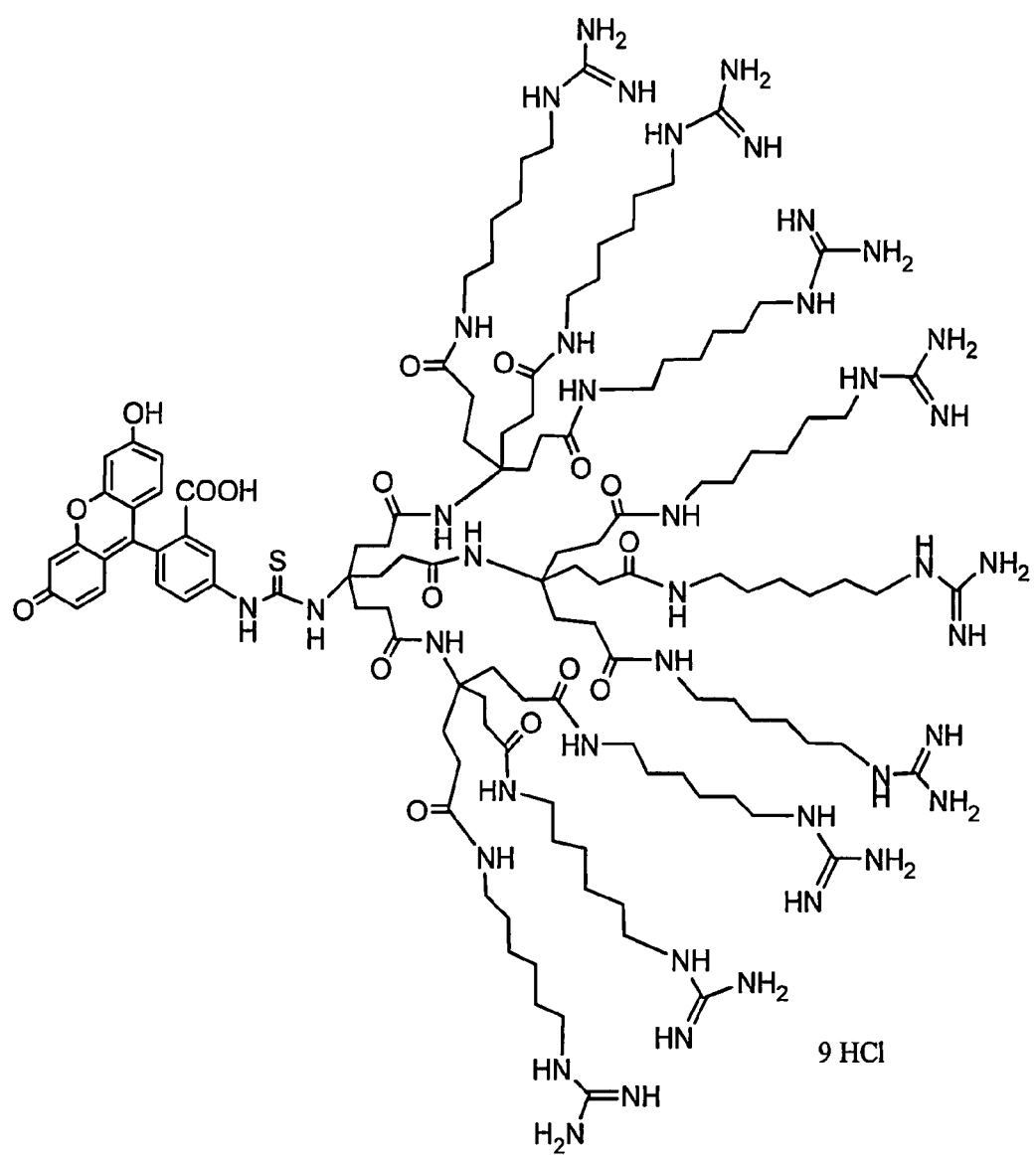
FIG. 1 shows a schematic representation of the structures for FD-1 and FD-2.

The present invention can be understood more readily by reference to the following detailed description of aspects of the invention and the Examples included therein and to the Figures and their previous and following description.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can need to be independently confirmed.

Before the present compounds, compositions, articles, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a component," "a polymer," or "a residue" includes mixtures of two or more such components, polymers, or residues, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the terms "optional" or "optionally" means that the subsequently described event or circumstance may or may not occur, and that the description includes instances where said event or circumstance occurs and instances where it does not.

As used herein, the term "organic quantum dot" refers to a generally carbon based compound having a generally particle-like overall structure and comprising a generally central functional moiety. In one aspect, an organic quantum dot is prepared via intramolecular chain collapse. In a further aspect, an organic quantum dot can be prepared from a block copolymer comprising at least two reactive moieties and at least one functional moiety.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

As used herein, the term "oligomer" refers to a relatively low molecular weight polymer in which the number of repeating units is between two and ten, for example, from two to eight, from two to six, or form two to four. In one aspect, a collection of oligomers can have an average number of repeating units of from about two to about ten, for example, from about two to about eight, from about two to about six, or form about two to about four.

As used herein, the term "reactive residue" refers to a moiety (e.g., a monomer residue) capable of undergoing chemical reaction at a reaction temperature and/or in response to a stimulus to form a reactive intermediate. In one aspect, a reactive residue is a moiety capable undergoing an intramolecular cross-linking reaction to provide intramolecular chain collapse.

As used herein, the term "polymerizable group" refers to a group (i.e., a chemical functionality) capable of undergoing a polymerization reaction at a polymerization temperature and/or in response to a polymerization initiator to form a polymer or an oligomer. In one aspect, the polymerization reaction is a radical polymerization (e.g., a vinyl polymerization). It is understood that catalysts can be employed in connection with the polymerization reaction. It is contemplated that, in various aspects, polymerizable groups can be used in step-growth or chain growth reactions. Exemplary polymerizable groups include residues of vinyl, styryl, acryloyl, methacryloyl, aryl, and heteroaryl compounds.

As used herein, the term "reactive intermediate" refers to a chemical species formed from a reactive moiety and in response to a stimulus and/or at a reaction temperature and capable of undergoing further chemical reaction (e.g., cross-linking) with another reactive intermediate. In one aspect, two reactive intermediates can undergo a cross-linking reaction to provide intramolecular chain collapse.

As used herein, the term "o-quinoid moiety" refers to a reactive intermediate formed from, for example, a benzocyclobutene moiety a reaction temperature and/or in response to a stimulus. In one aspect, an o-quinoid moiety can have the general structure:

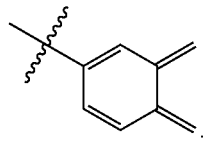

It is understood that a reactive moiety capable of forming an o-quinoid moiety can be provided as, for example, a residue or as a pendant group in a copolymer. In a further aspect, an o-quinoid moiety can be further substituted.

As used herein, the term "functional moiety" refers to a moiety (e.g., a monomeric residue) capable of performing a function, for example an imaging function or a drug-delivery function. In one aspect, a functional moiety can be provided in a generally central portion of an organic quantum dot. In various further aspects, a functional moiety can comprise a semiconducting moiety, an imaging moiety, and/or a drug-delivery moiety.

As used herein, the term "stimulus" refers to an external condition or event that is capable of acting upon a reactive species, for example a reactive moiety, to produce a reactive intermediate, for example an o-quinoid moiety. In various aspects, a stimulus can refer to temperature (i.e, thermal stimulus), a chemical species (i.e., a chemical stimulus) such as a radical or an increase or decrease in pH, or light (i.e., an electromagnetic stimulus) or a mixture thereof).

As used herein, the term "subject" means any target of administration. The subject can be an animal, for example, a mammal (e.g., a human, horse, pig, rabbit, dog, sheep, goat, non-human primate, cow, cat, guinea pig, or rodent), a fish, a bird or a reptile or an amphibian. The term does not denote a particular age or sex. Thus, adult and newborn subjects, as well as fetuses, whether male or female, are intended to be covered. In a further example, the subject can be a human. In an even further example, the subject can be a cell. A "patient" refers to a subject afflicted with a disease or disorder. The term "patient" includes human and veterinary subjects.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. In various aspects, a preparation can be administered therapeutically; that is, administered to treat an existing disease or condition. In further various aspects, a preparation can be administered prophylactically; that is, administered for prevention of a disease or condition. In a further aspect, "administering" and "administration" can refer to administration to cells that have been removed from a subject (e.g., human or animal), followed by re-administration of the cells to the same, or a different, subject.

As used herein, the term "effective amount" refers to such amount as is capable of performing the function of the compound or property for which an effective amount is expressed. As will be pointed out below, the exact amount required will vary from process to process, depending on recognized variables such as the compounds employed and the processing conditions observed. Thus, it is not typically possible to specify an exact "effective amount." However, an appropriate effective amount may be determined by one of ordinary skill in the art using only routine experimentation. In various aspects, an amount can be therapeutically effective; that is, effective to treat an existing disease or condition. In further various aspects, a preparation can be prophylactically effective; that is, effective for prevention of a disease or condition.

As used herein, the term "biologically active agent" or "bioactive agent" means an agent that is capable of providing a local or systemic biological, physiological, or therapeutic effect in the biological system to which it is applied. For example, the bioactive agent can act to control infection or inflammation, enhance cell growth and tissue regeneration, control tumor growth, act as an analgesic, promote anti-cell attachment, and enhance bone growth, among other functions. Other suitable bioactive agents can include anti-viral agents, hormones, antibodies, or therapeutic proteins. Other bioactive agents include prodrugs, which are agents that are not biologically active when administered but, upon administration to a subject are converted to bioactive agents through metabolism or some other mechanism. Additionally, any of the compositions of the invention can contain combinations of two or more bioactive agents. It is understood that a biologically active agent can be used in connection with administration to various subjects, for example, to humans (i.e., medical administration) or to animals (i.e., veterinary administration).

As used herein, the term "pharmaceutically active agent" includes a "drug" or a "vaccine" and means a molecule, group of molecules, complex or substance administered to an organism for diagnostic, therapeutic, preventative medical, or veterinary purposes. This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA) or ribonucleic acid (RNA). Pharmaceutically active agents include the herein disclosed categories and specific examples. It is not intended that the category be limited by the specific examples. Those of ordinary skill in the art will recognize also numerous other compounds that fall within the categories and that are useful according to the invention. Examples include a radiosensitizer, the combination of a radiosensitizer and a chemotherapeutic, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal anti-inflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides. It is understood that a pharmaceutically active agent can be used in connection with administration to various subjects, for example, to humans (i.e., medical administration) or to animals (i.e., veterinary administration).

As used herein, the term "imaging moiety" refers to any chemical groups or sunstance useful for imaging applications, as known to those of skill in the art. Examples of imaging agents include radioconjugate, cytotoxin, cytokine, Gadolinium-DTPA or a quantum dot, iron oxide, manganese oxide. In one aspect, an imaging agent can be provided in nanoparticular form or in microparticular form. In a further aspect, an imaging agent comprises Gadolinium-DTPA and iron oxide nanoparticles (magnetite), as specific MRI contrast agents. In a yet further aspect, an imaging agent comprises at least one near infrared dye, for example near infrared dyes based on a porphyrin and/or a phthalocyanine. See Ghoroghchian et al., Near-infrared-emissive polymersomes: Self-assembled soft matter for in vivo optical imaging, *PNAS*, 2005, vol. 102, no. 8, 2922-2927. In a still further aspect, the imaging agent comprises two or more quantum dots, wherein the two or more quantum dots have different emission wavelengths. It is understood more than one imaging agent can be used in connection with the disclosed inventions, such as quantum dot—Gd-DTPA—iron oxide nanoparticle co-encapsulated species.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 40 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkyloxycarbonyl" as used herein to refers to a group comprising the general structure:

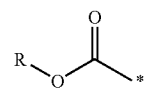

wherein R is an alkyl group, which can be substituted or unsubstituted. Examples of R substituents include t-butyl, benzyl, allyl, and 2,2,2-trichloroethyl. In one aspect, an alkyloxycarbonyl group can be used as a protecting group for an amine moiety. Examples of such protecting groups include Boc (tert-butyloxycarbonyl), Cbz (benzyloxycarbonyl), Alloc (allyloxycarbonyl), and Troc (2,2,2-trichloroethyloxycarbonyl).

The term "alkenyl" as used herein is a hydrocarbon group of from 2 to 40 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 40 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon tripple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or substituted or unsubstituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)$A^1$ or —C(O)O$A^1$, where $A^1$ can be a substituted or unsubstituted alkyl, cycloalkyl, alkenyl, cycloalkenyl, alkynyl, cycloalkynyl, aryl, or heteroaryl group as described herein. The term "polyester" as used herein is represented by the formula -($A^1O(O)C-A^2-C(O)O)_a$— or -($A^1O(O)C-A^2-OC(O))_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an interger from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein. The term "polyether" as used herein is represented by the formula -($A^1O-A^2O)_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "hydroxyl" as used herein is represented by the formula —OH.

The term "ketone" as used herein is represented by the formula $A^1C(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or a substituted or unsubstituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or a substituted or unsubstituted alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, a substituted or unsubstituted alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, a substituted or unsubstituted alkyl, cycloalkyl, alkenyl, cycloalkenyl, alkynyl, cycloalkynyl, aryl, or heteroaryl group as described herein.

The term "thiol" as used herein is represented by the formula —SH.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. DENDRIMERIC COMPOUNDS

Dendrimers can be ideal building blocks for biomedical applications, because of their precise architecture, high loading capacity, tunable solubility, immunogenicity, and bioconjugation capability. [Gillies, E. R.; Fréchet, J. M. J. Drug Discov. Today 2005, 10, 35.; Lee, C. C.; MacKay, J. A.; Fréchet, J. M. J.; Szoka, F. C. Nat. Biotechnol. 2005, 23, 1517.] The combination of the unique properties of dendrimers with membrane-permeable guanidino groups can lead to a more efficient-synthesis of membrane-permeable carrier molecules possessing high efficiency, for example, for bulk production.

The compounds of the invention are desirably based upon a compact, high branching multiplicity dendrimer, for example, the classic Newkome-type dendrimer. [Newkome, G. R.; Behera, R. K.; Moorefield, C. N.; Baker, G. R. J. Org. Chem. 1991, 56, 7162.] Newkome type dendrimers are typically 1→3 C-branched polyamide macromolecules, built from "Behera's Amine" monomer or its derivatives, and can be attached to a variety of starting cores, surfaces, and polymers.

It is also understood that the compounds of the invention can be tailored to enhance accumulation in specific sublocations of cells, such as the nucleus, the cytosol, or the mitochondria. Tailoring can be the selection of chemical moieties or groups having an affinity for a targeted subcellular region of a cell, for example an organelle, and the functionalization of the compounds with the selected chemical moieties or groups. Such tailoring of the compound structure can be accomplished using organic synthetic methodology know to those of skill in the art.

In one aspect, the invention relates to compounds comprising the structure:

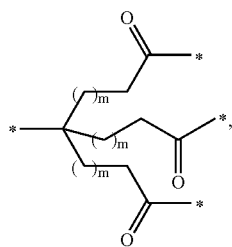

and at least one guanidinium residue, wherein m is zero or a positive integer. In certain aspects, m can be 0, 1, 2, 3, 4, 5, or 6 and each residue can be substituted or unsubstituted. In a further aspect, m is 1.

In one aspect, the invention relates to compounds comprising the structure:

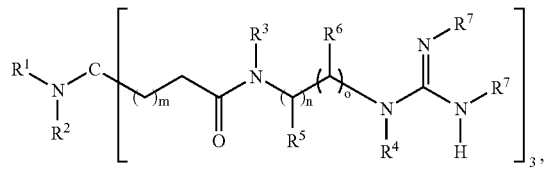

wherein n and o are, independently, zero or a positive integer; wherein $R^1$ and $R^2$ are, independently, hydrogen, oxygen, alkyl, acyl, thioacyl, or carbonyl; wherein $R^3$ is hydrogen, alkyloxycarbonyl, or alkyl; $R^4$ is hydrogen, or alkyloxycarbonyl; wherein $R^5$ and $R^6$ are, independently, hydrogen, or alkyl; and wherein $R^7$ is hydrogen or alkyloxycarbonyl.

In a further aspect, the compounds can comprise the structure:

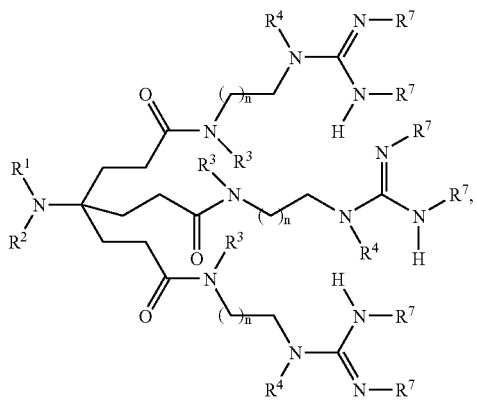

wherein n is an integer from 1 to 9; wherein $R^1$ and $R^2$ are, independently, hydrogen, oxygen, nitrogen, alkyl, acyl, thioacyl, carbonyl, or amine; wherein $R^3$ is hydrogen or alkyl; and wherein $R^4$ is hydrogen, or alkyloxycarbonyl, alkyl, or acyl. In certain aspects, n can be 0, 1, 2, 3, 4, 5, 6, 7, 8, or 9. In a further aspect, n is 1 or 5. In a further aspect, $R^4$ can be hydrogen or alkyloxycarbonyl. In a further aspect, $R^7$ is Boc, for example, t-Boc.

In one aspect, the compound comprises the structure:

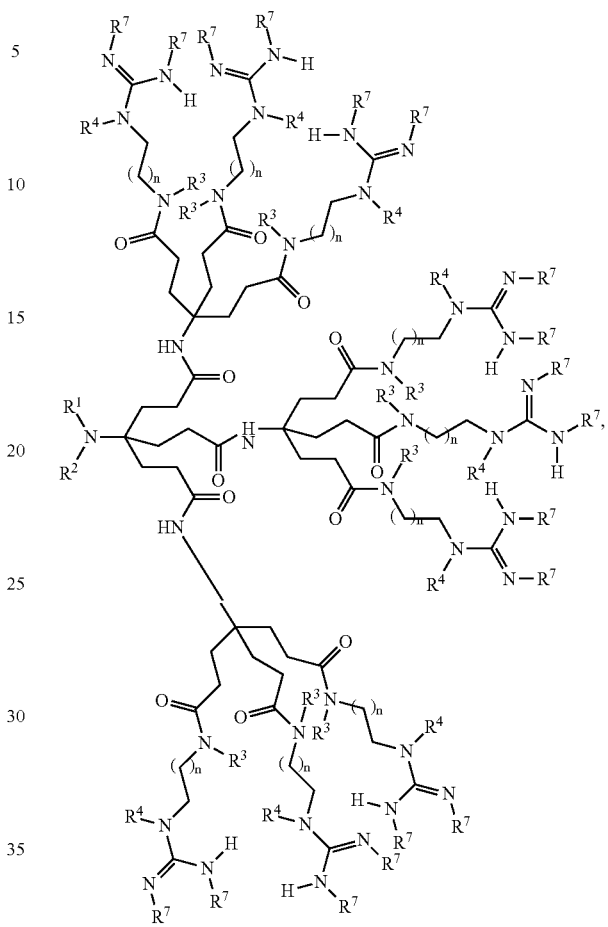

wherein n is an integer from 1 to 9; wherein $R^1$ and $R^2$ are, independently, hydrogen, amino, hydroxyl, alkyl, alkoxyl, acyl, carbonyl, or thioacyl; wherein $R^3$ is hydrogen or alkyl; and wherein $R^4$ is hydrogen, or alkyloxycarbonyl.

C. METHODS OF MAKING DENDRIMERIC COMPOUNDS

Figure 6A:
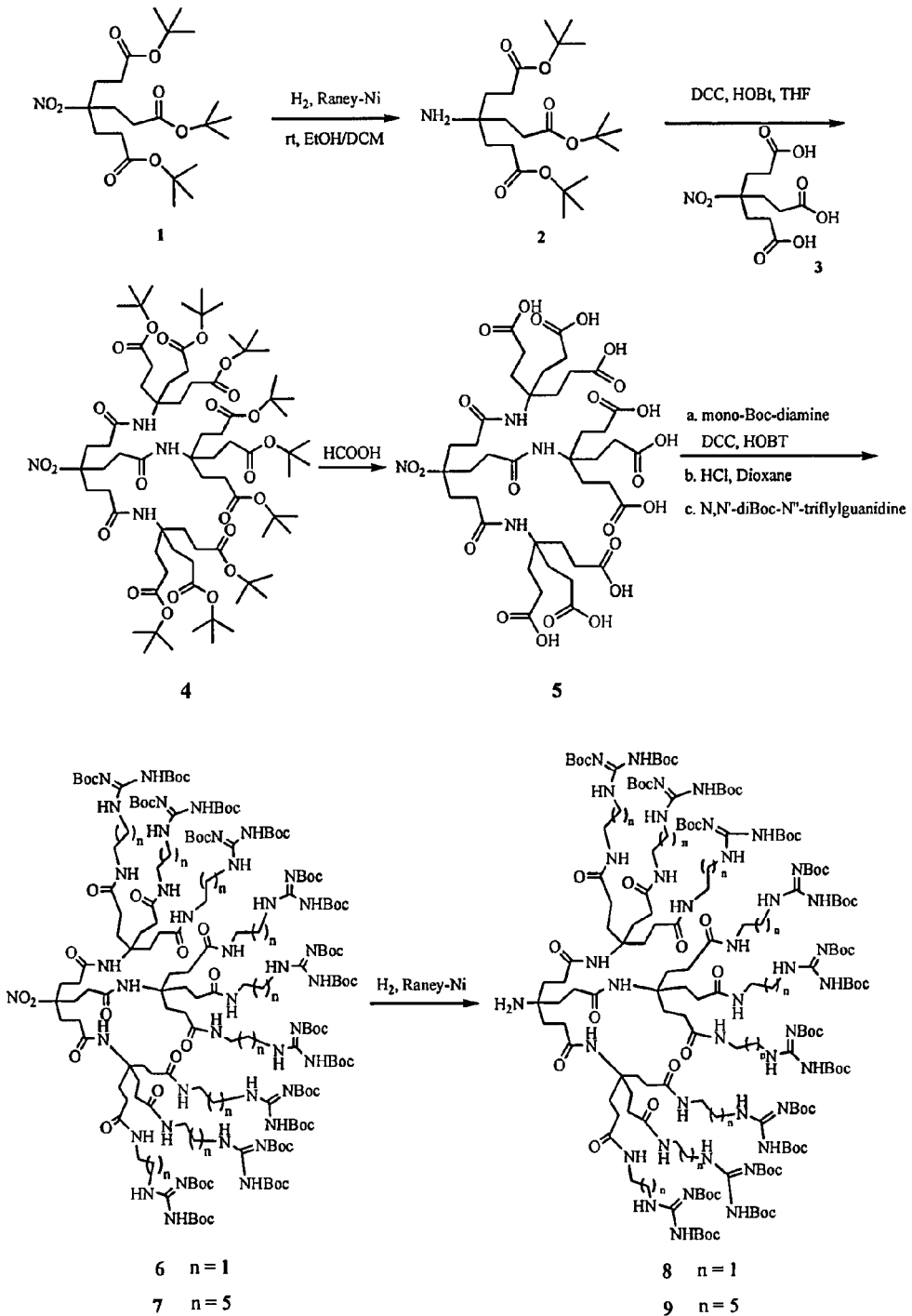
FIGS. 6A and 6B show an exemplary synthetic scheme for the preparation of FD-1, FD-2, and intermediates thereof.
Figure 6B:
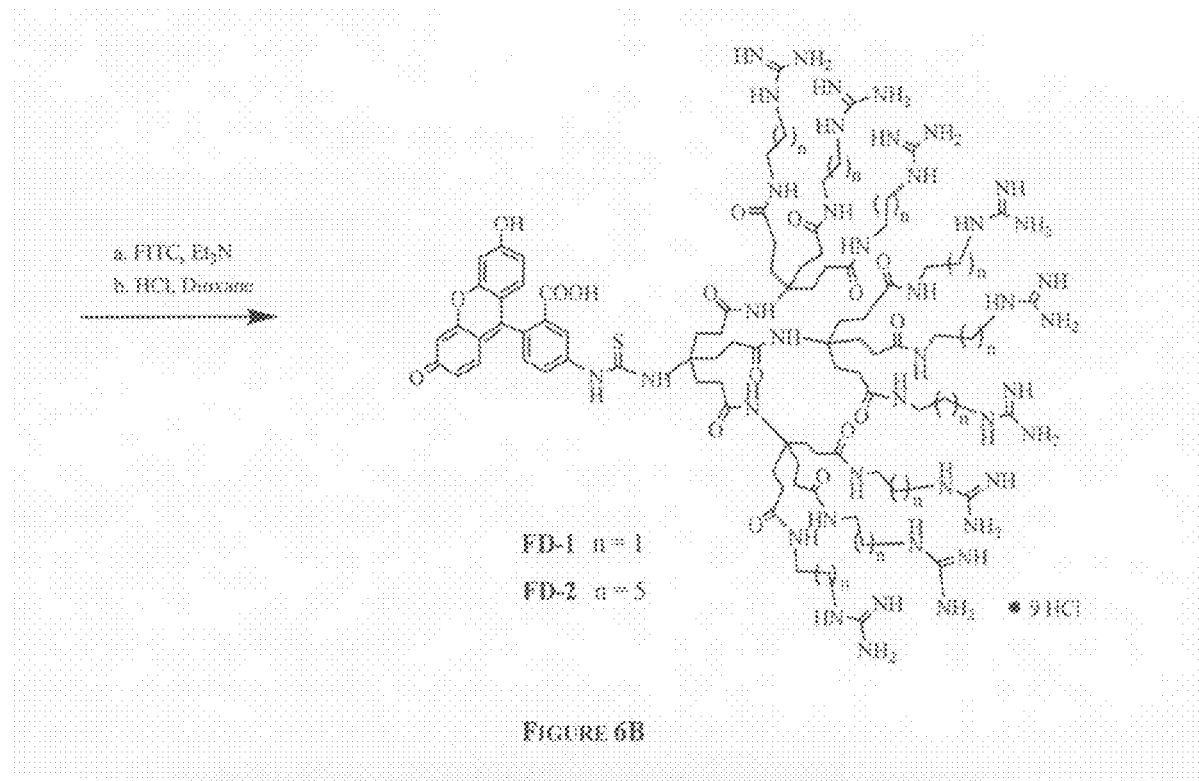

The disclosed methods typically employ a divergent method to prepare a G-1 dendrimer scaffold with nine end functionalities. Although the Newkome type dendrimer is well known, one of the drawbacks for a broader application of conventional methods is the elaborate synthesis of the monomer. In contrast, the "Behera's amine" gives the most compact, low molecular weight polyamide dendrimer possible; achieving the necessary nine end functionalities in just one generation of dendritic growth. As set forth below and in the Experimental section, following synthesis of the monomer through improved hydrogenation and work-up procedures, the G-1 dendritic nona-acid scaffold can be prepared in high yields (see FIGS. 6A and 6B).

In order to introduce the guanidinium groups to the dendrimer exterior as shown in FIG. 1, the nine carboxylic acid groups were first converted into nine protected amine groups, by reaction with, for example, N-Boc ethylendiamine and N-Boc-1,6-diaminehexane through amide coupling reactions. After removal of the protecting groups, the nine free amines can be reacted with a guandinylating reagent [Feichtinger, K.; Sings, H. L.; Baker, T. J.; Matthews, K.; Goodman, M. J. Org. Chem. 1998, 63, 8432.] to give a guanidinylated dendritic scaffold in high yield.

For uptake evaluation and imaging function, a fluorophore can be conjugated to the focal point of the molecular transporter. The attachment of a fluorescein isothiocyanate (FITC) moiety to the guanidinylated scaffold can be achieved with a reduction of the nitro group at the focal point to an amino group via hydrogenation at room temperature in quantitative yields, followed by direct reaction with FITC to form the Boc-protected FITC-labeled guanidino-dendrimer. After deprotection of the Boc-protected guanidine groups, FITC-labeled dendritic molecules can be obtained and further purified by dialysis or HPLC.

In one aspect, the invention relates to methods of preparing compounds having the structure:

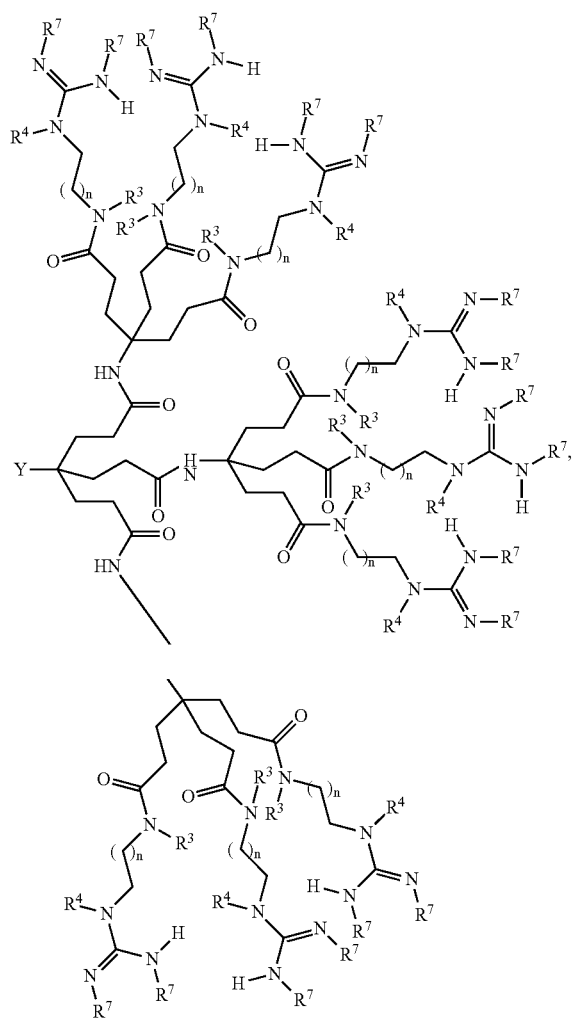

wherein n is an integer from 1 to 9, wherein $R^3$ is hydrogen or alkyl, wherein $R^4$ and $R^7$ are, independently, hydrogen, alkyloxycarbonyl, alkyl, or acyl; wherein $R^7$ is hydrogen, alkyl, or acyl; wherein Y comprises a nitro group, an amine group, an amide group, azide group, or an alkyloxycarbonyl protected amine group or a derivative thereof, the method comprising the steps of providing a first compound comprising the structure:

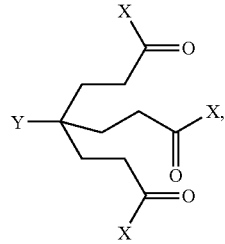

wherein X comprises OH, halogen, or OC(O)-alkyl; coupling the first compound with at least about three molar equivalents of a second compound comprising the structure:

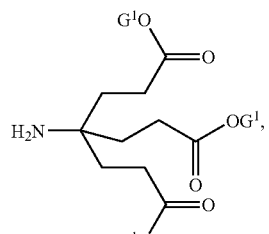

wherein $G^1$ is an ester-protecting group; removing the ester-protecting group; reacting the product of step (c) with at least about three molar equivalents of a third compound comprising the structure:

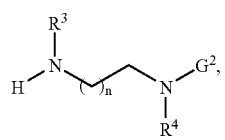

wherein $G^2$ is an amine-protecting group; removing the amine-protecting group; and functionalizing the product of step (e) with at least three molar equivalents of a guanidine-providing agent.

In a further aspect, the guanidine-providing agent comprises at least one of N,N'-diBoc-N''-triflylguanidine, N,N'-diCbz-N''-triflylguanidine, N,N'-dialloc-N''-triflylguanidine, N,N'-ditroc-N''-triflylguanidine, 1,3-diboc-2-(2-hydroxyethyl)guanidine, N,N'-diBoc-1H-pyrazole-1-carboxamidine, N,N'-diCbz-1H-pyrazole-1-carboxamidine, 1H-pyrazole-1-carboxamidine hydrochloride, 1,3-diboc-2-(2-hydroxyethyl)guanidine, 2-(2-aminoethyl)-1,3-diboc-guandine, or 1,3-diboc-2-(carboxymethyl)guanidine In a further aspect, the method further comprises the step of transforming Y into an amine to provide a compound comprising the structure:

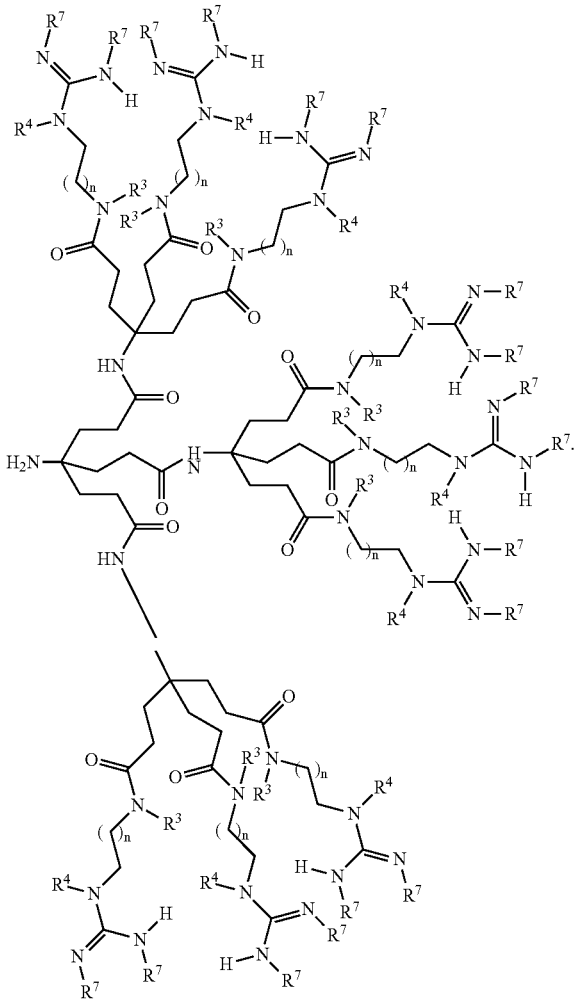

In a further aspect, the method further comprises the step of removing $R^7$. The removing step can be, for example, treatment with one or more reagents known to those of skill in the art for removing protecting groups.

In one aspect, the providing step comprises synthesis of the starting materials. Each starting material can be obtained commercially and/or prepared by those of skill in the art from commercially available compounds. For example, the nitro-ester shown below can be prepared using methodology from Newkone, G. R.; Behera, R. K.; Moorefield, C. N.; Baker, G. R.; *J. Org. Chem.* 1991, 56, 7162:

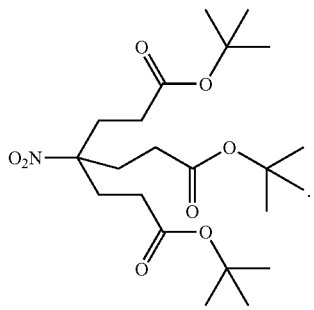 [SMILES: CC(C)(C)OC(=O)CCC(CCC(=O)OC(C)(C)C)(CCC(=O)OC(C)(C)C)[N+](=O)[O-] ; "."]

In a further aspect, the ester-protecting group comprises methyl, ethyl, or t-butyl.

In a further aspect, the amine-protecting group comprises a butyloxycarbonyl group, a trifluoroacyl group, a 9-fluorenyl-methyloxycarbonyl group, an alloc group, or a carbobenzyloxy group.

In a further aspect, the method further comprises the step of acylating the amine with a compound comprising the structure:

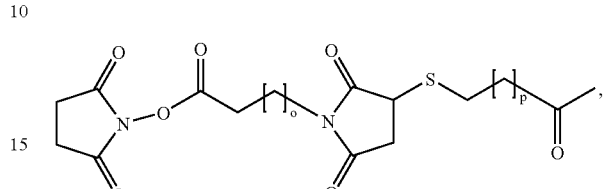

wherein o and p are, independently, zero or a positive integer.

In a yet further aspect, the method further comprises the step of reacting the product of the acylating step with a payload compound comprising at least one amine group and at least one of a luminescent group, a biologically active group, or a pharmaceutically active group.

In a further aspect, the method further comprises the step of acylating the amine with a fourth compound comprising the structure:

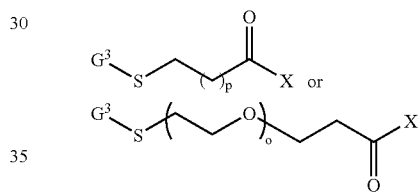

wherein o and p are, independently, zero or a positive integer, and wherein $G^3$ is an thiol-protecting group.

In a further aspect, the thiol protecting group comprises the structure:

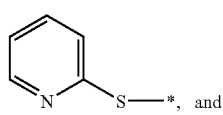

wherein the fourth compound comprises the structure:

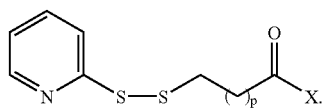

In a further aspect, the thiol-protecting group comprises the structure:

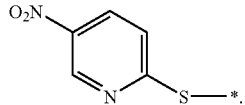

In a further aspect, the method further comprises the step of removing the thiol-protecting group, thereby providing a deprotected thiol. In a yet further aspect, the method further comprises the step of attaching the deprotected thiol to a thiol-functionalized payload. In a still further aspect, the thiol-functionalized payload comprises at least one of a luminescent group, a biologically-active group, or a pharmaceutically-active group.

D. COMPOSITIONS

In one aspect, the invention relates to compositions comprising one or more compounds of the invention or one or more products of the methods of the invention.

1. Intracellular Delivery Compositions

In one aspect, the invention relates to intracellular delivery compositions comprising the general structure P-L-B-F, wherein P is payload moiety; wherein L is a linking moiety comprising the structure:

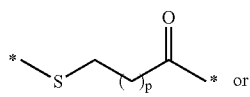

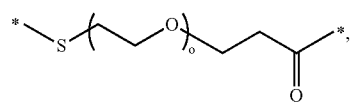

wherein o and p are, independently, zero or a positive integer; wherein B is a branching moiety comprising the structure:

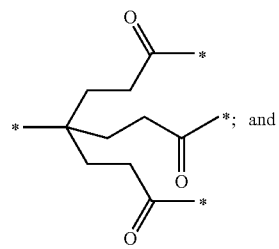

wherein F is a functional moiety comprising at least one guanidinium residue. In a further aspect, p is an integer from 0 to 6, for example, 0, 1, 2, 3, 4, 5, or 6. In a further aspect, the composition comprises at least six guanidinium residues, at least seven guanidinium residues, at least eight guanidinium residues, or at least nine guanidinium residues.

In one aspect, L-B-F comprises the structure:

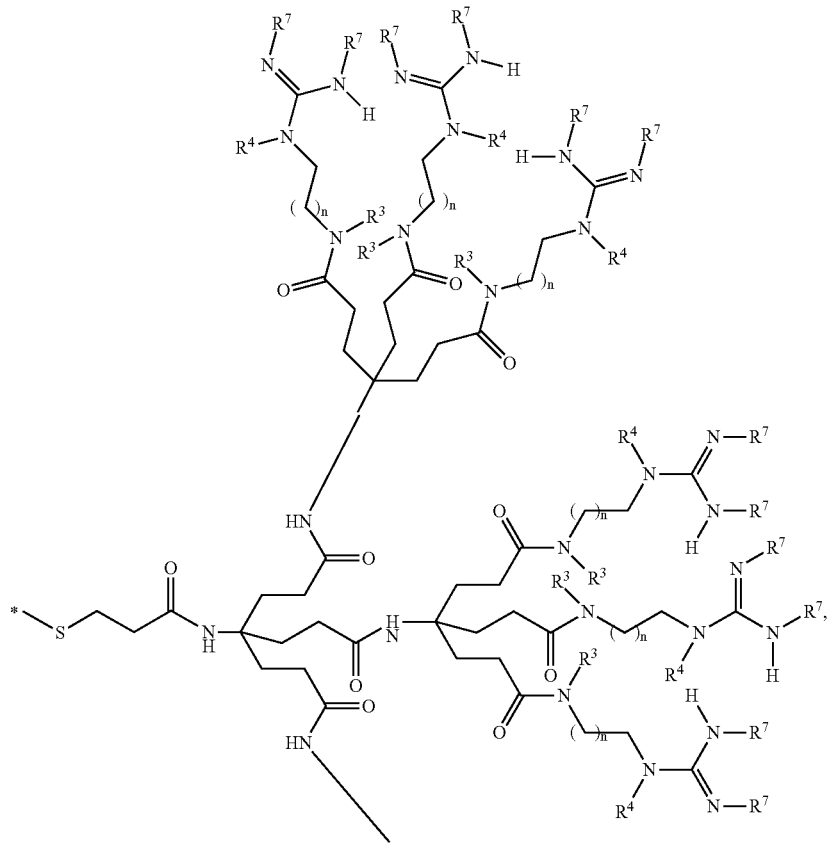

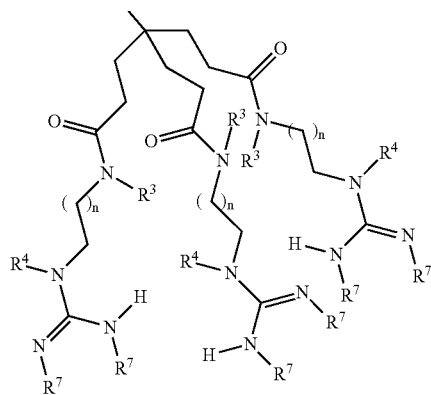
20
wherein n is an integer from 1 to 9; wherein $R^3$ is hydrogen or alkyl; wherein $R^4$ is hydrogen, alkyl or acyl; and wherein $R^7$ is hydrogen, alkyl or acyl.
In a further aspect, P-L-B-F comprises the structure:
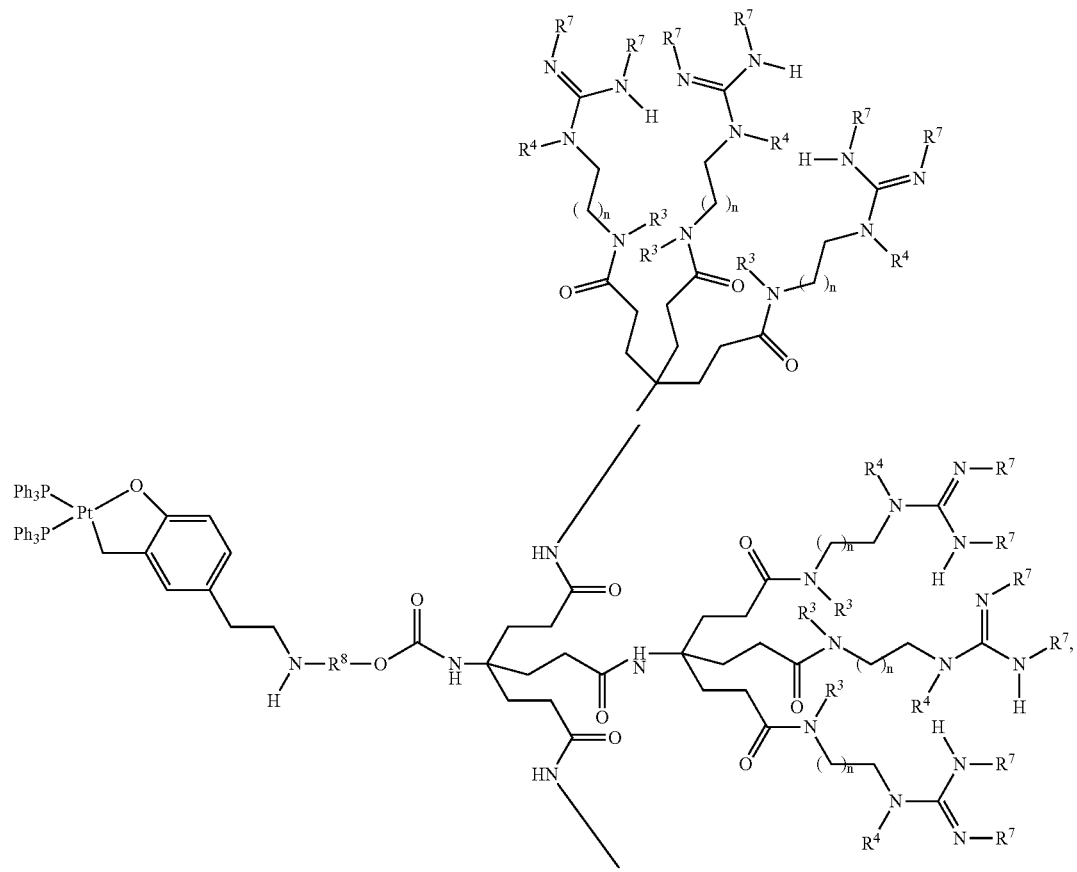

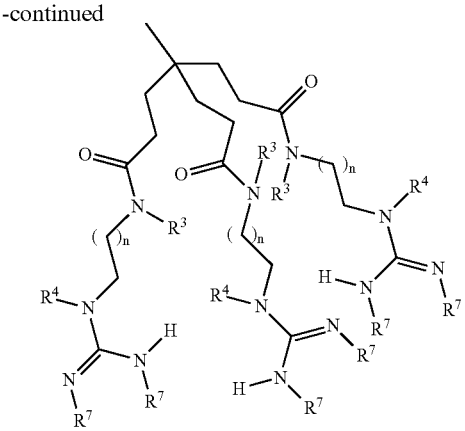

wherein n is an integer from 1 to 9; wherein $R^3$ is hydrogen or alkyl; wherein $R^4$ is hydrogen, alkyl or acyl; wherein $R^7$ is hydrogen, alkyl or acyl; and wherein $R^8$ comprises the structure:

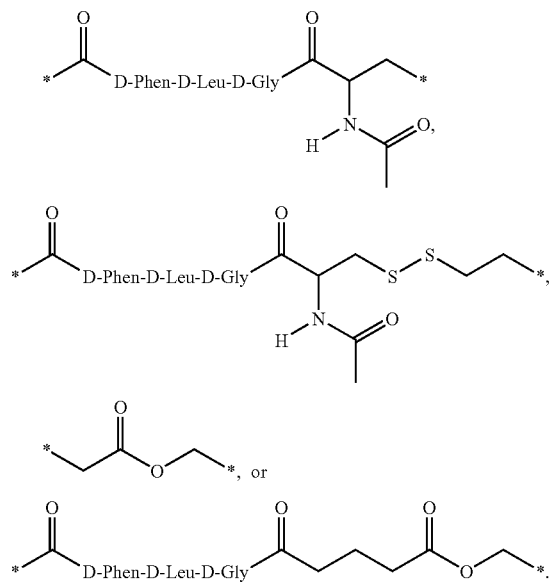

a. Payloads

Typically, the compounds of the invention can be functionalized to carry a payload. In various aspects, a payload compound can be attached or associated with a compound of the invention by covalent bonding, by ionic bonding, by coordination bonding, or by hydrogen bonding. In further aspects, a payload compound can be associated with a compound of the invention by hydrophilic interactions or hydrophobic interactions. In certain aspects, a payload compound is part of a compound of the invention, while in certain further aspects, payload compound is a separate compound from of a compound of the invention.

In one aspect, the payload moiety bears a thiol moiety. In a further aspect, the payload moiety is a luminescent group. For example, the luminescent group can comprise the structure:

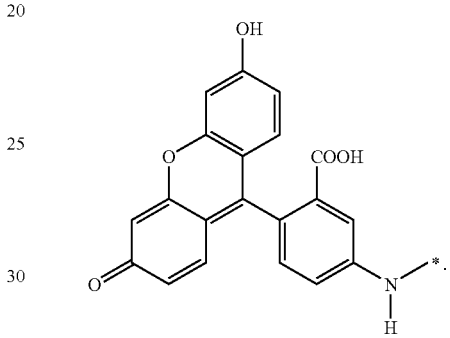

In certain aspects, the luminescent group is selected from a dansyl group, a coumarin group, an FITC group, a DOTA group, a catechol group, or a DPTA group. DOTA, catechol, and/or DPTA groups can be used for complexing, for example, lanthanides. Catechol can be used for complexing, for example, quantum dots, lanthanides, metals (such as iron or copper (e.g., radioactive Cu)), ironoxides, metal oxides, and/or platinum (e.g., cis-platinum).

In a further aspect, the payload moiety is a biologically-active group. For example, the biologically-active group can be selected from one or more of an oligonucleotide, a plasmid DNA, a protein, an immunoglobulin, an antisense oligoDNA, a peptide nucleic acid (PNA), or a peptide. For example, in various aspects, the biologically-active group can comprise one or more of β-galactosidase, horseradish peroxidase, RNase, anti-apoptotic proteins Bcl-X(L)/PEA-15, catalase, green fluorescence protein, heat shock protein 70, human glutamate dehydrogenase, ovalbumin, neuroptotectant Bcl-xL, E2 protein, phosphorothioate antisense oligonucleotides, anti-tetanus F(ab')$_2$, G protein, p16$^{INK4a}$, caspase-3, p14$^{INK4a}$, p27$^{kip1}$, Bak BH3 domain peptide, cGPK-Iα inhibitory peptide, IKKβ C-terminal peptide, PKA inhibitory peptide, MEK 1 N-terminal peptide, luciferin, RhoA, APOBEC-1, Cre recombinase, H-Ras, Filmin-1, p16, HPC-1/syntaxin, Cdk2, E2f-1/p73/p53, influenza virus, bacteria, birdflu virus, and/or bacteria.

In a further aspect, the payload moiety is a pharmaceutically-active group. For example, the pharmaceutically-active group is selected from a small molecular weight drug, a silica nanoparticle, a metal nanoparticle, a protein, a peptide, a linear polymer backbone, a hydrogel, a collapsed nanoparticle, a dendrimers, or a hyperbranched polymeric structure. For example, in various aspects, the pharmaceutically-active group can comprise one or more of superparamagnetic iron oxide particles, doxorubicin, methotrexate, liposome, multiple sclerosis agents, cis-platinum, paclitaxel, hormones, antioxidants, antimicrobials, antibacterial agents, antidepressants, sedatives, antihypertensive drugs, antibodies, a carbohydrate-based drug, cardioprotective ϵPKC agonist peptide, Fab fragments of the anti-melanoma antibody NRML-05, pan-carcinoma antibody NRLU-10, anti-CEA immunotoxin, liposome drugs, fusogenic, dendritic cell vaccines, VHL tumor suppressor peptide, HER-2, Pro-apoptoxic Smac peptide, viralcapsids, and/or bacteria.

b. Intracellular Delivery

In one aspect, the invention relates to methods of intracellular delivery comprising administering an effective amount of one or more compounds of the invention or one or more compositions of the invention to a subject. The subject is a mammal, for example, a human. In a further aspect, the subject is a cell. The delivery can be, for example, oral, transmucosal, rectal, or subcutaneous administration or, for example, intravenous, intrathecal, intramuscular, intranasal, intraperitonel, or intraocular injection.

2. Pharmaceutical Compositions

A pharmaceutical composition comprising a therapeutically effective amount of one or more compounds of the invention or one or more compositions of the invention and a pharmaceutically acceptable carrier for administration in a mammal, for example, a human. The compositions can be, for example, granules, powders, tablets, or capsules.

a. Dosage

A "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

b. Carriers

A "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents, and dispersing agents. Prevention of the action of microorganisms may be ensured by the inclusion of various antibacterial and antifungal agents such as paraben, chlorobutanol, phenol, sorbic acid, and the like. It can also be desirable to include isotonic agents such as sugars, sodium chloride, and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

E. SYNTHESIS AND CHARACTERIZATION OF "BOW-TIE" DENDRITIC MOLECULAR TRANSPORTERS BY ORTHOGONAL AND CLICK APPROACH

Disclosed is the synthesis and characterization of "Bow-Tie" dendritic architectures with orthogonally reactive groups, defined composition and functionality, which can be used as multi-drug carries for specific intracellular delivery. Huisgen cycloadditions or so called "click" reactions have been shown to be extremely versatile tools for advanced macromolecular design. However, little attempt has been made to utilize this approach to prepare multifunctional dendritic structures. In the disclosed approach, two orthogonal protected dendritic structures are combined by utilizing the "click" reaction. This strategy allows the controlled deprotection of the trifluoro protecting group to selectively attach the dithiopyridylpropionic acid the periphery of the macromolecule. In a further step, the BOC groups of the second dendritic scaffolds are deprotected to be guanydilated to the ethyl- or hexyl linker of the system. The bow-tie structure is the first of its kind that consists of a molecular transporter part and drug delivery entity on the other. The chemistry applied for the construction is high-yielding and, thus, gives the bow-tie delivery structure in the most straightforward approach. In this fashion, nine drug molecules, for example peptides, genes and oligonucleotides can be transported across cellular membranes.

Synthetic Pathway of Acid-labile Azide-linker-Dendron:
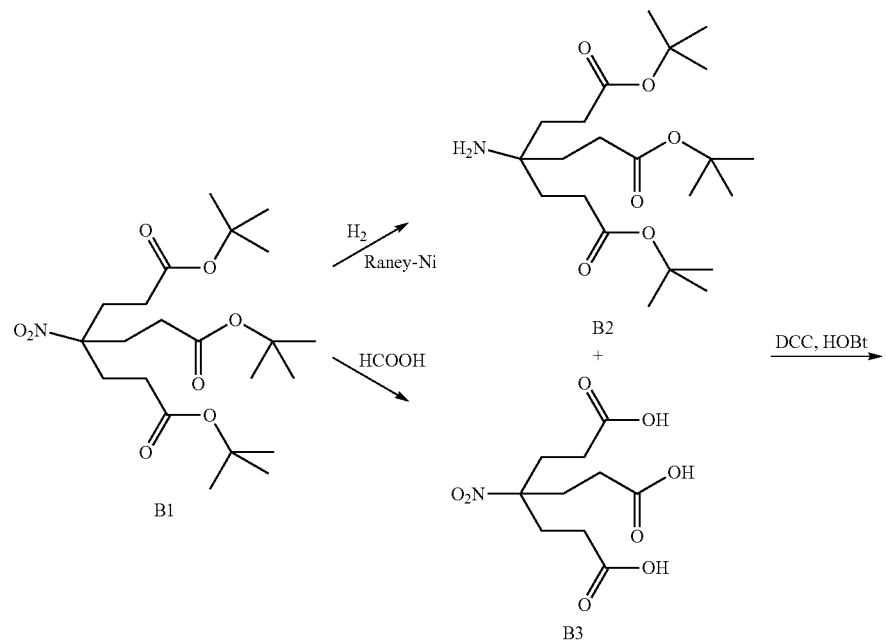
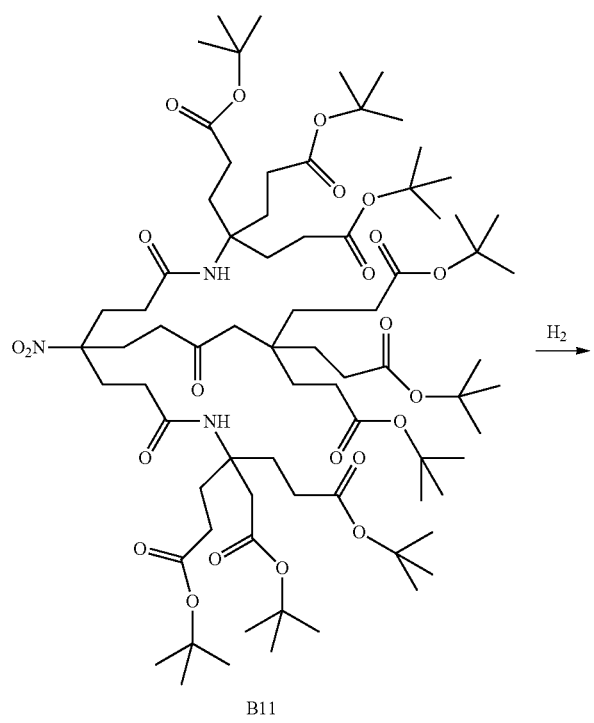

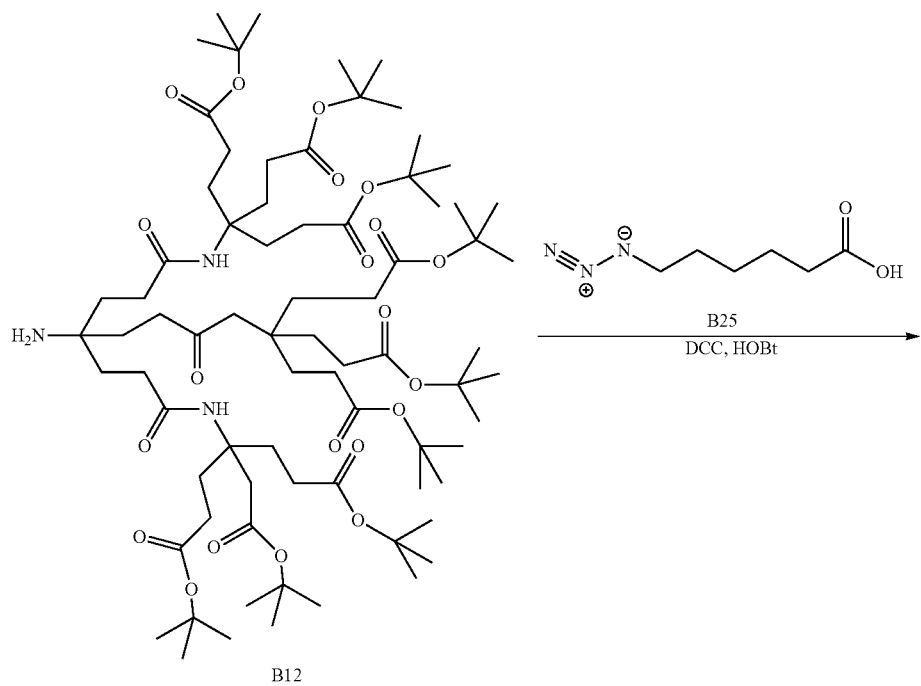
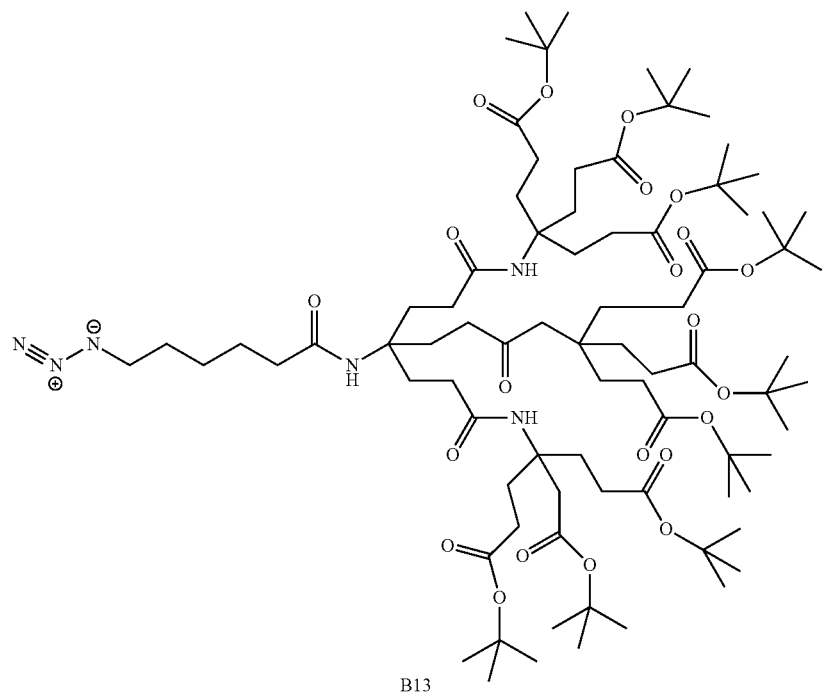

Synthetic Pathway for Base-labile Alkyne-linker-Dendron:
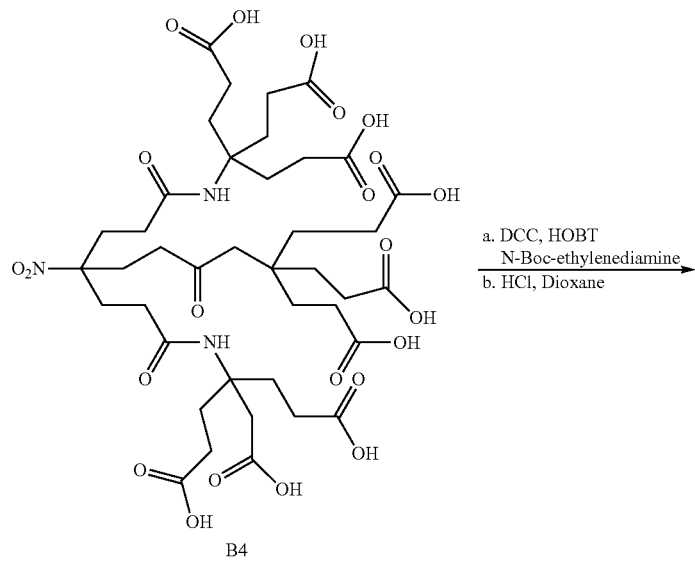
B4
a. DCC, HOBT, N-Boc-ethylenediamine
b. HCl, Dioxane
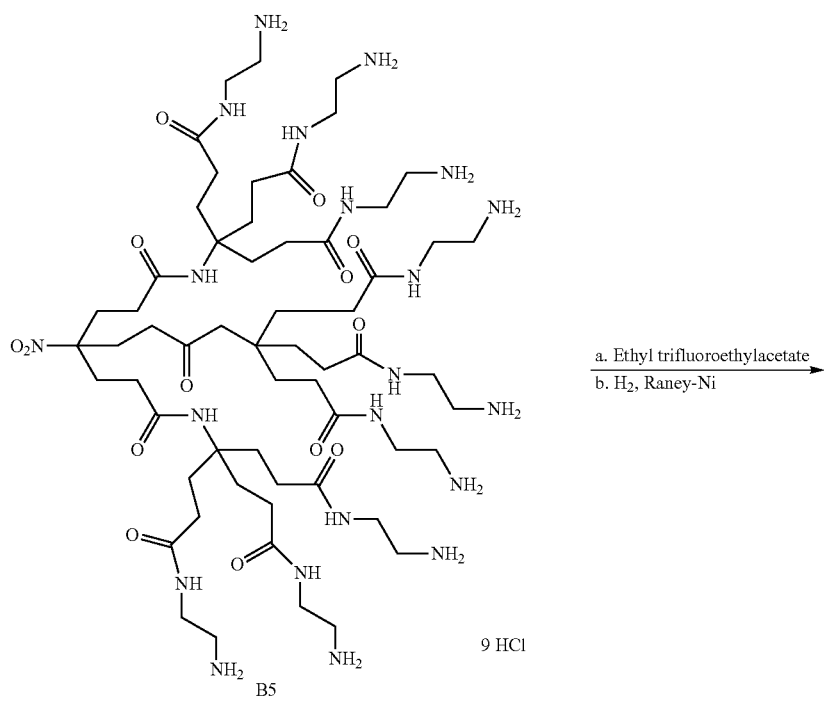
B5 · 9 HCl
a. Ethyl trifluoroethylacetate
b. H₂, Raney-Ni

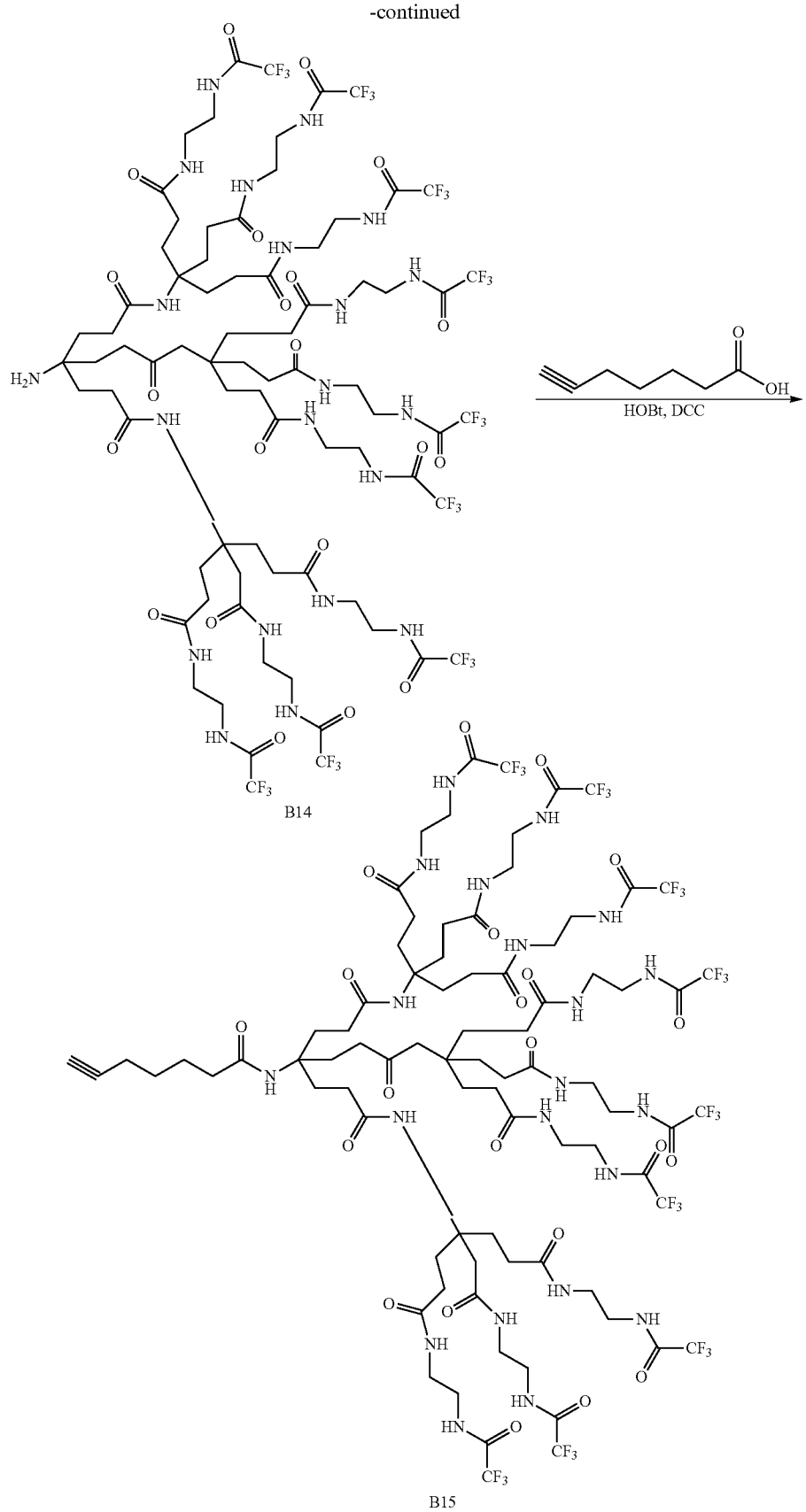
Bifunctional Bow-Tie Synthesis by Click Reaction:

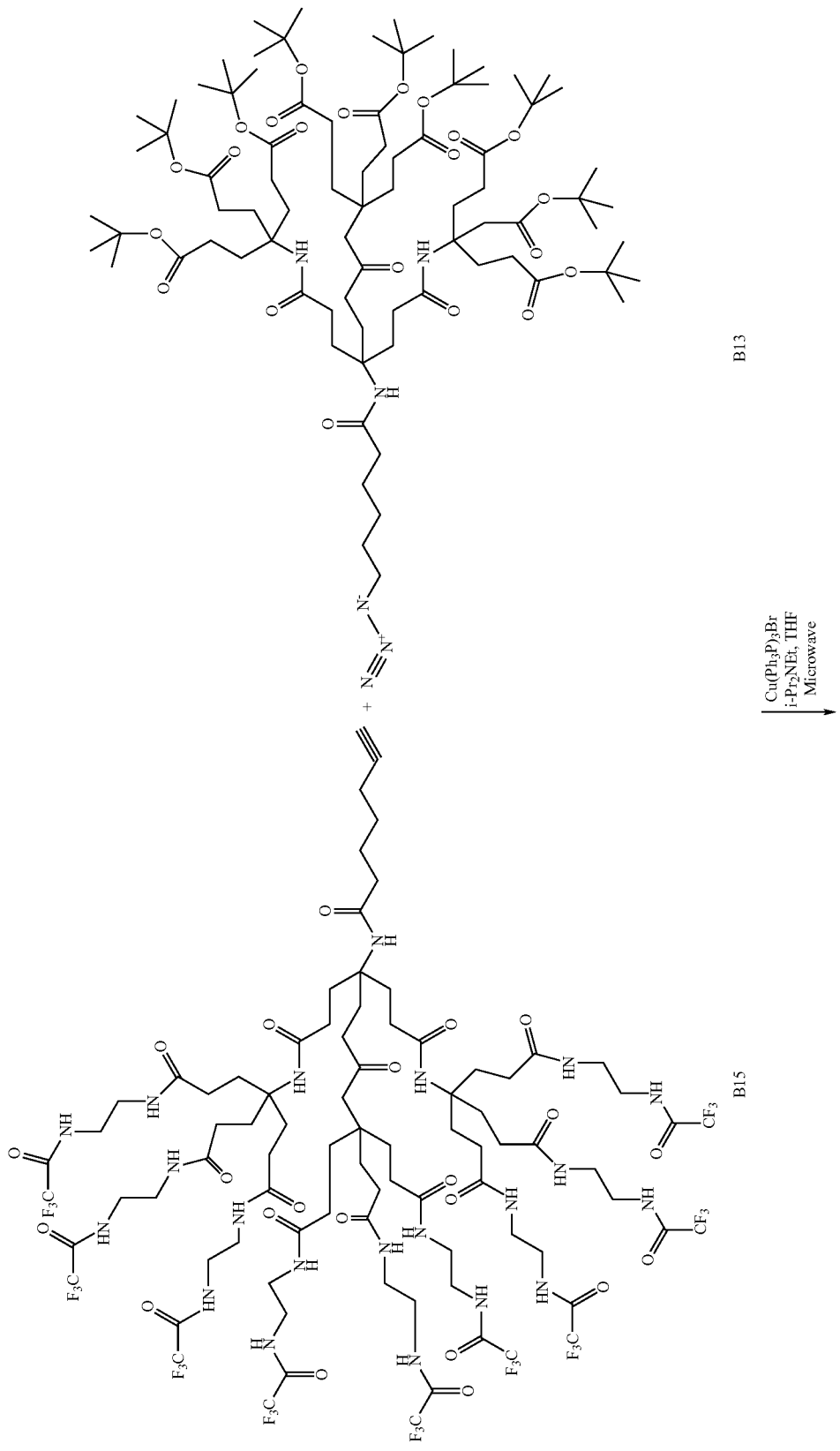

-continued
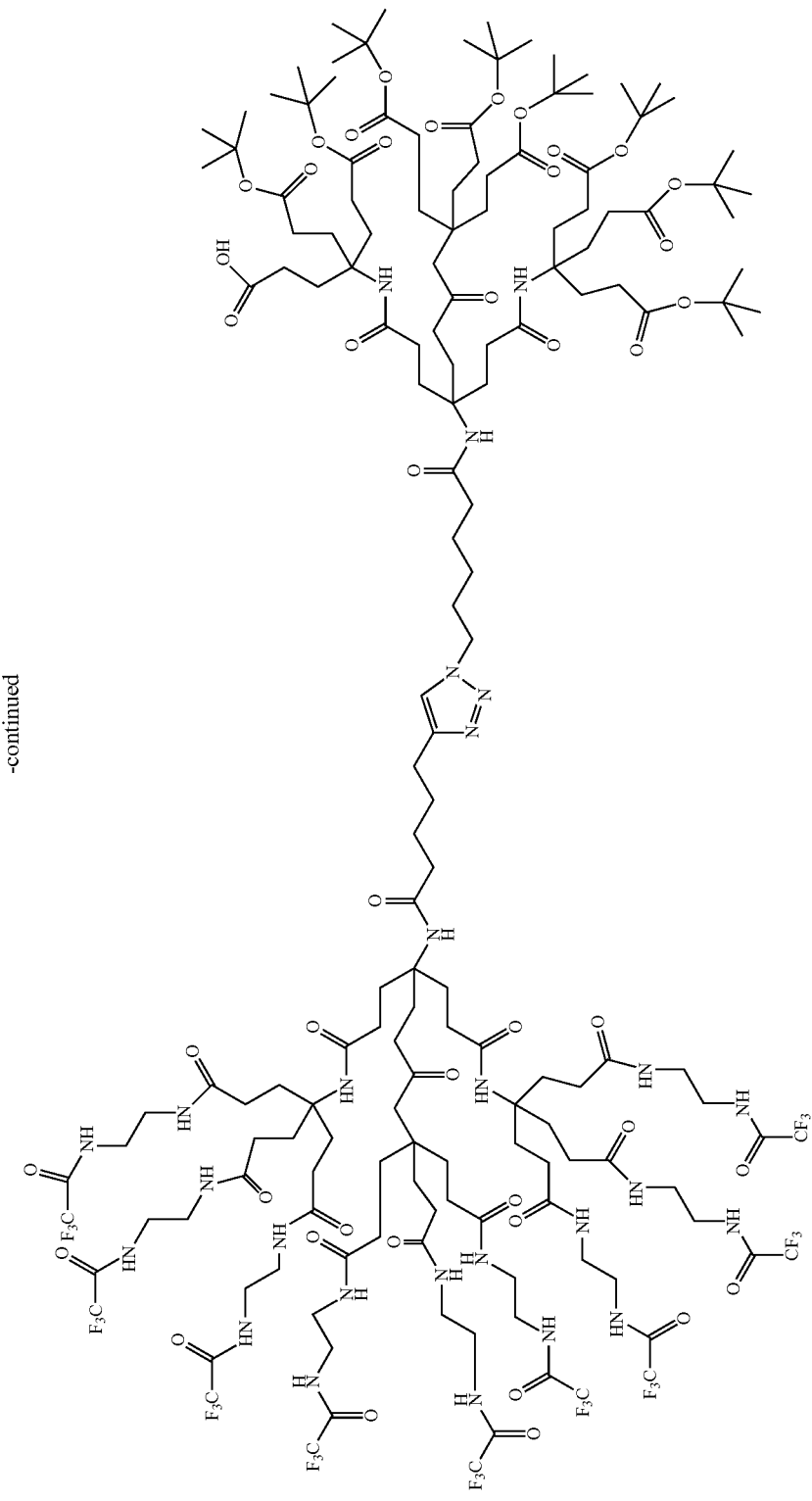
B16

Further Functionalization for Synthesis of Cell-Permeable
Multi-Drug Carrier Conjugates:

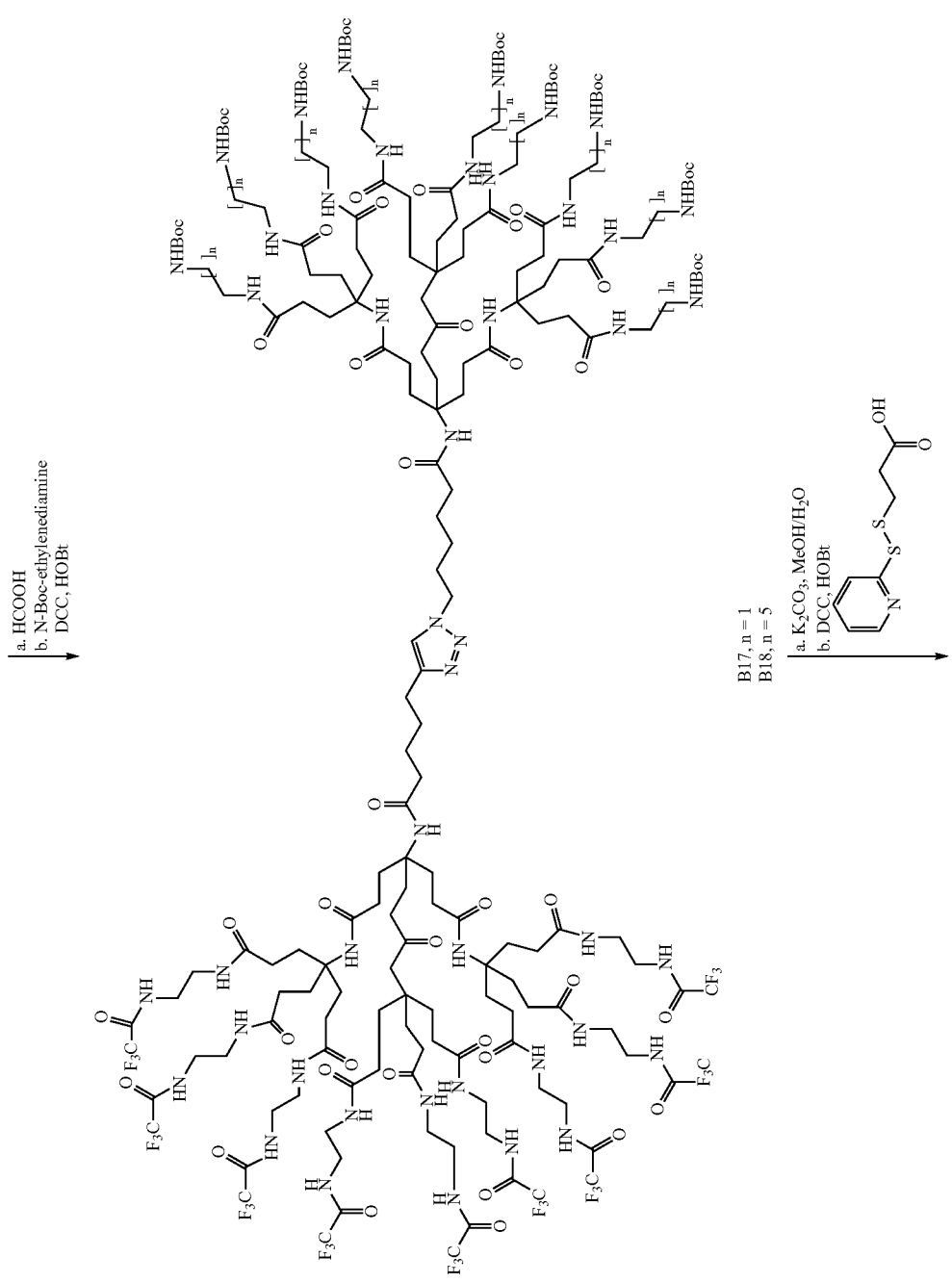

-continued
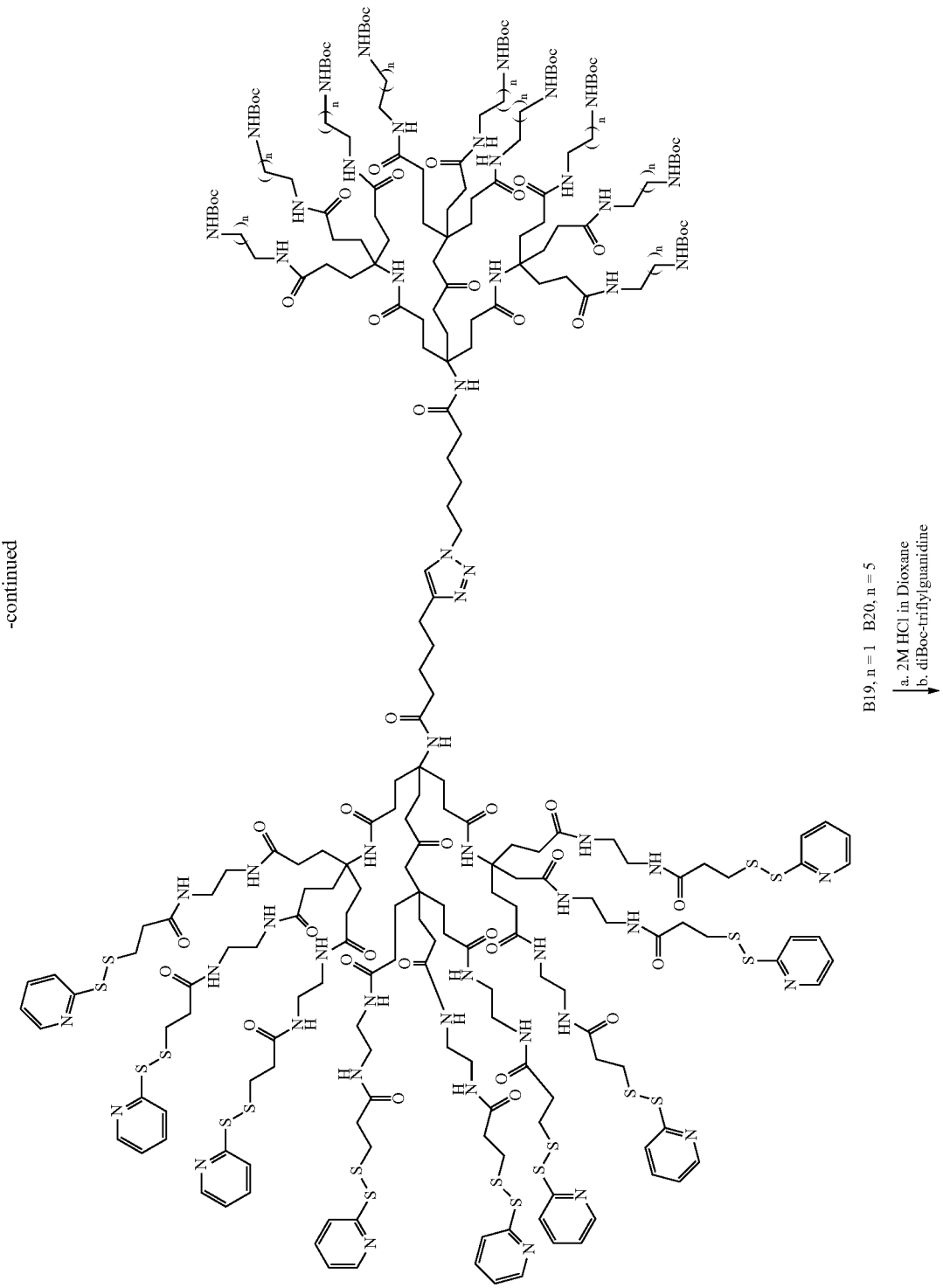
B19, n = 1  B20, n = 5
a. 2M HCl in Dioxane
b. diBoc-triflylguanidine -continued
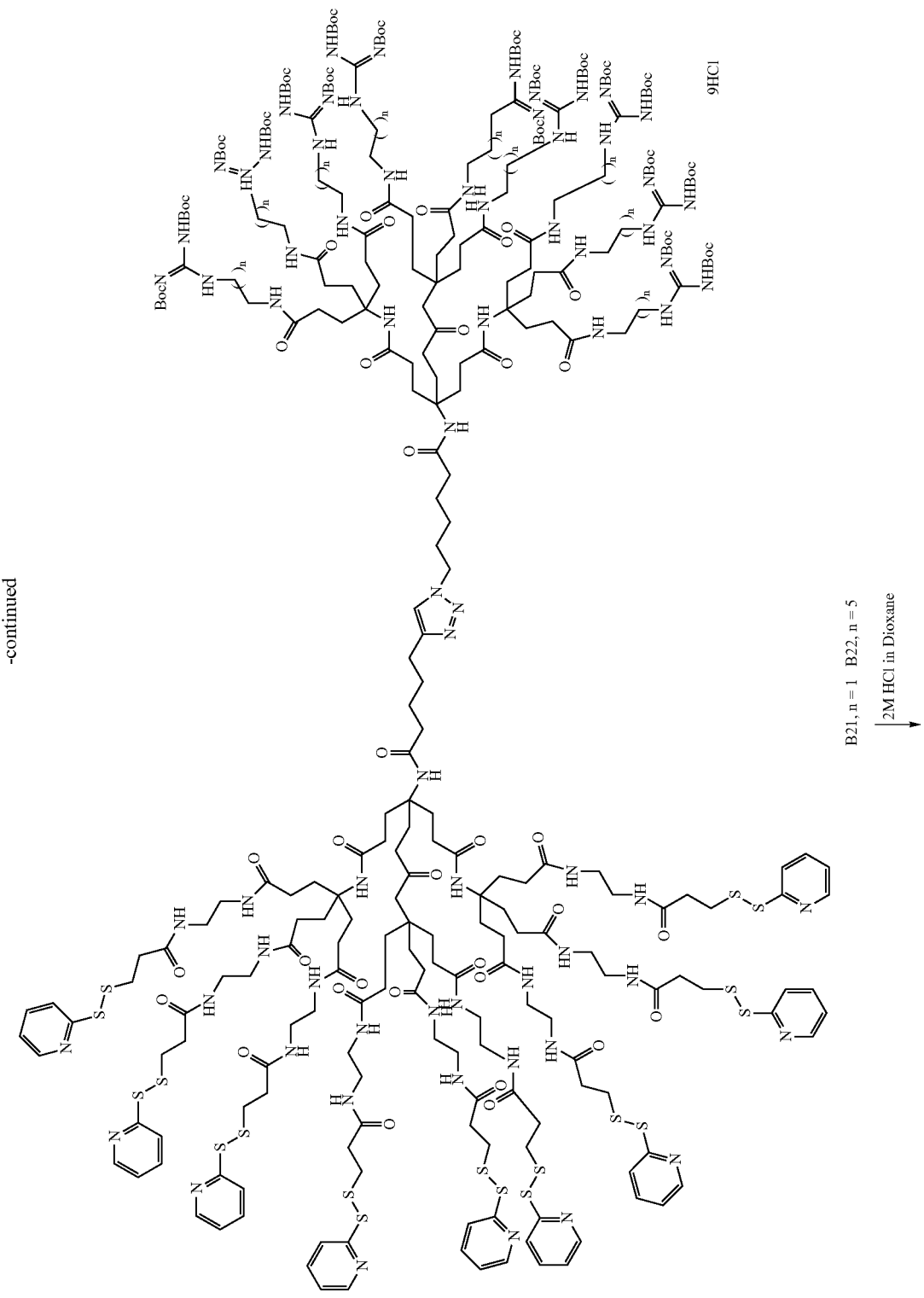
B21, n = 1  B22, n = 5
2M HCl in Dioxane -continued
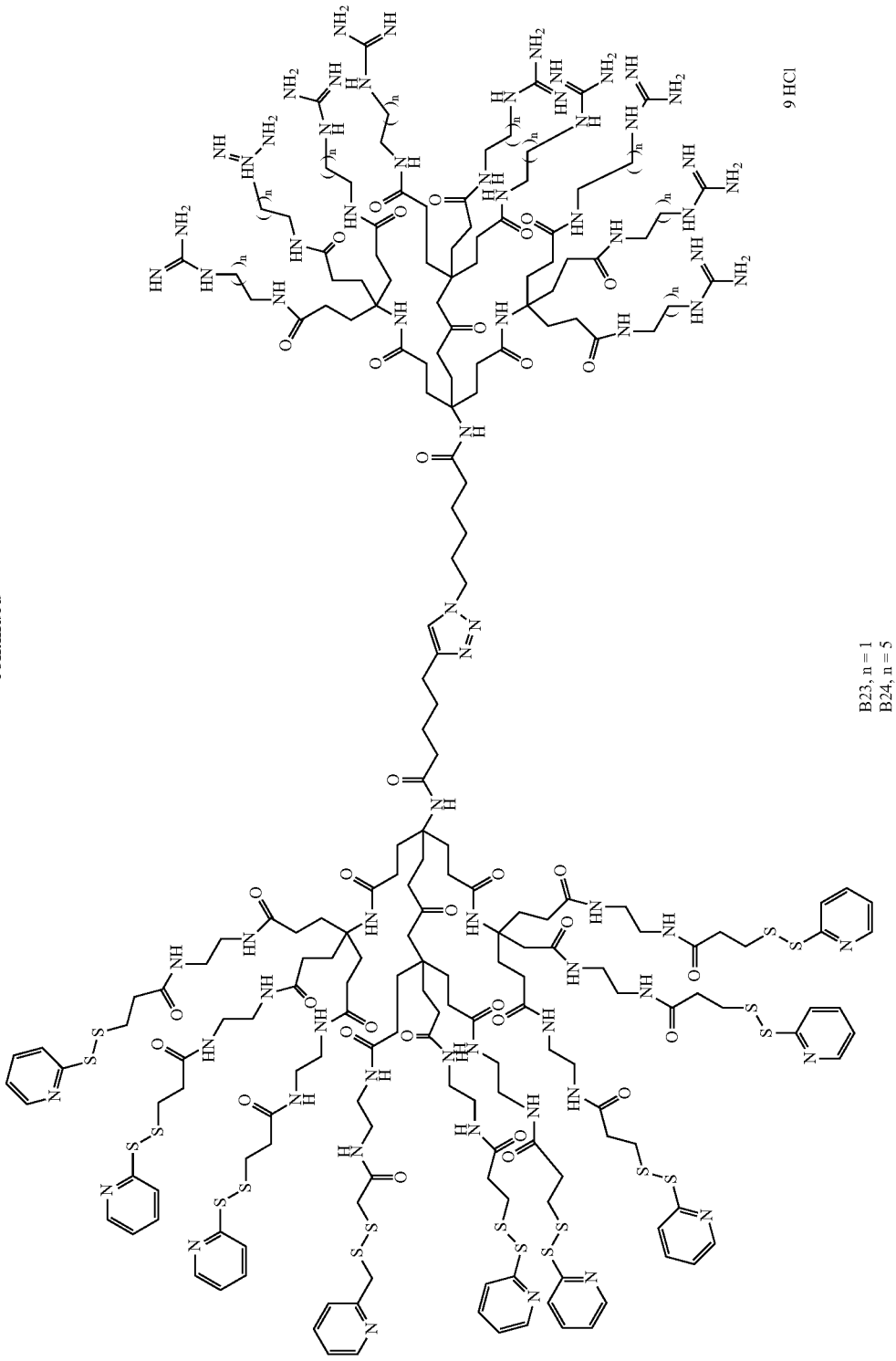
9 HCl
B23, n = 1
B24, n = 5

In one aspect, the invention relates to compounds comprising the structure:

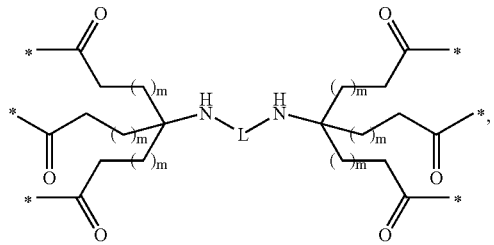

wherein each m is independently zero or a positive integer, and wherein L is a linking moiety comprising optionally substituted alkyl, optionally substituted alkoxyl, optionally substituted heteroalkyl, or optionally substituted heteroaryl.

In a further aspect, L comprises a structure:

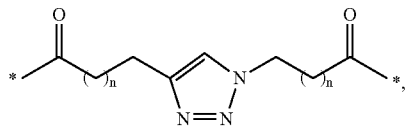

wherein each n is independently selected from 0-8. That is, L can comprise the reaction product of a "click" reaction.

In a further aspect, the compound can comprise a structure

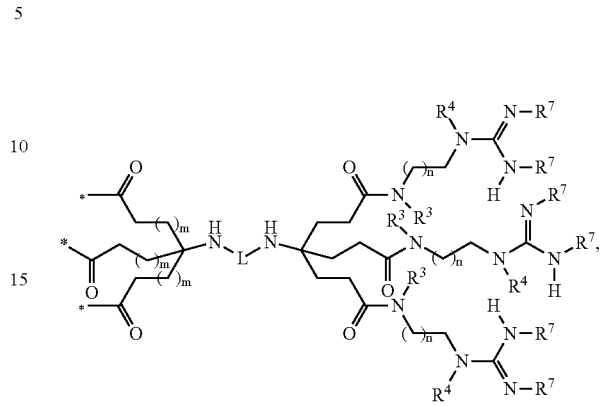

wherein n is an integer from 1 to 9; wherein $R^3$ is hydrogen or alkyl; wherein $R^4$ is hydrogen, or alkyloxycarbonyl, alkyl, or acyl; and wherein $R^7$ is hydrogen or alkyloxycarbonyl.

In a yet further aspect, the compound can comprise the structure:

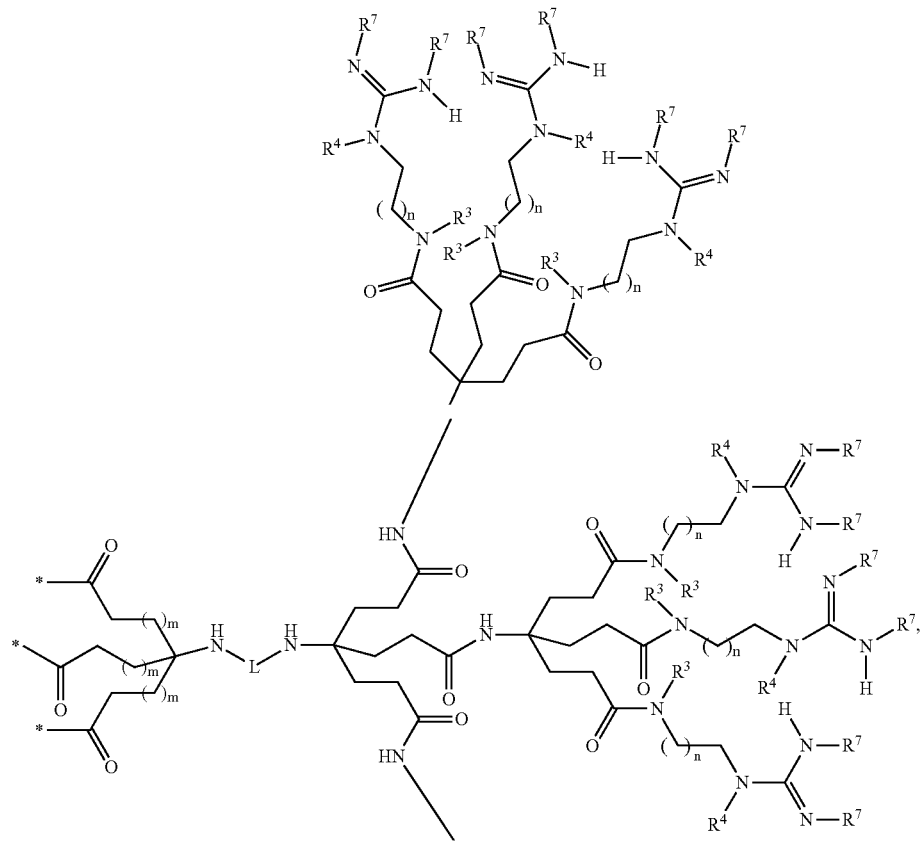

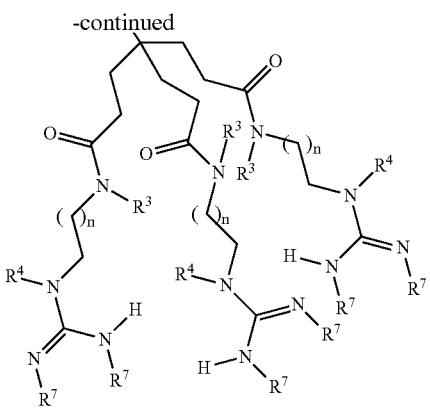

wherein n is an integer from 1 to 9; wherein $R^3$ is hydrogen or alkyl; wherein $R^4$ is hydrogen, or alkyloxycarbonyl, alkyl, or acyl; and wherein $R^7$ is hydrogen or alkyloxycarbonyl.

In a still further aspect, the compound can comprise the structure:

wherein n is an integer from 1 to 9; wherein $R^3$ is hydrogen or alkyl; wherein $R^4$ is hydrogen, or alkyloxycarbonyl, alkyl, or acyl; and wherein $R^7$ is hydrogen or alkyloxycarbonyl.

In an even further aspect, the compound can comprise the structure:

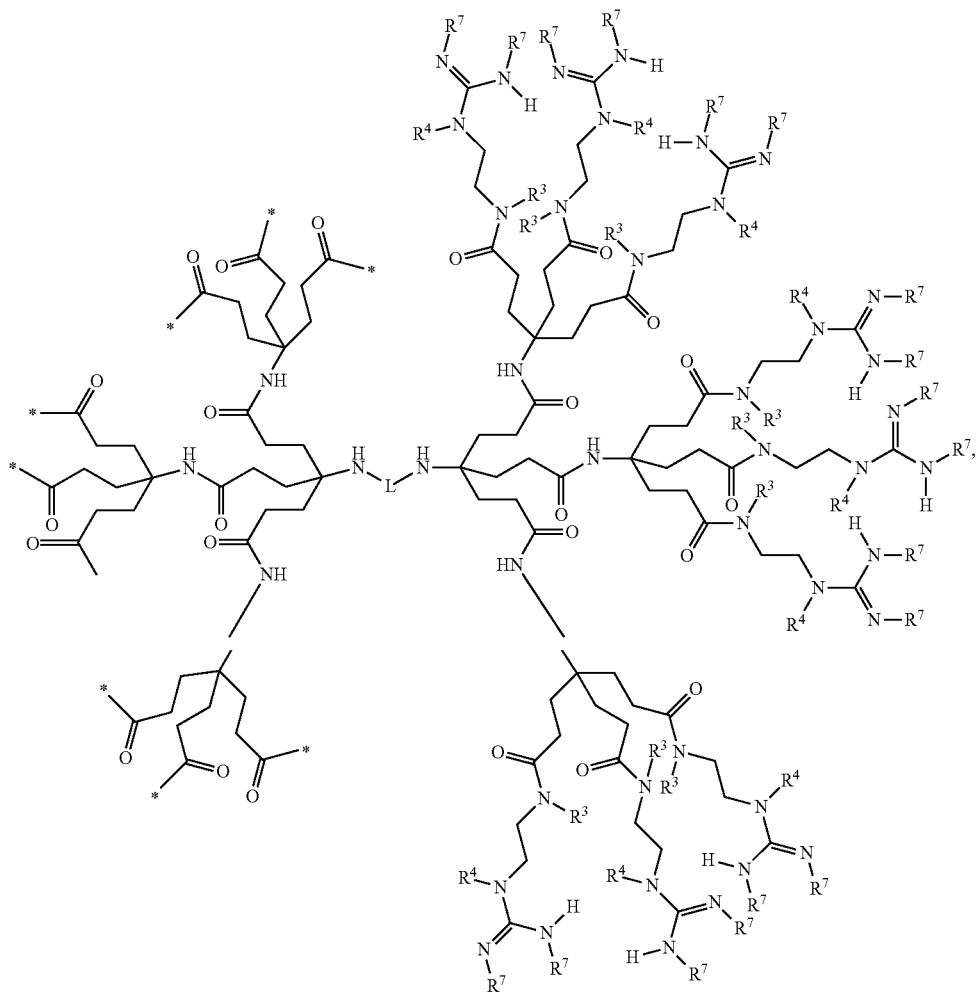

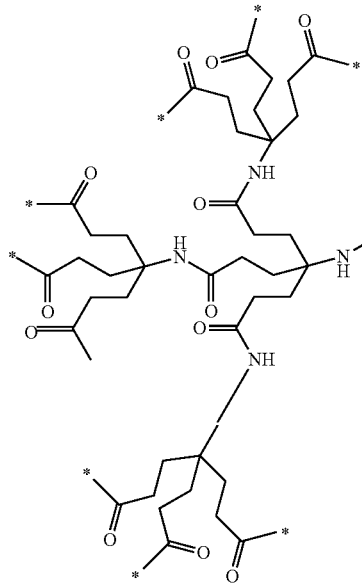
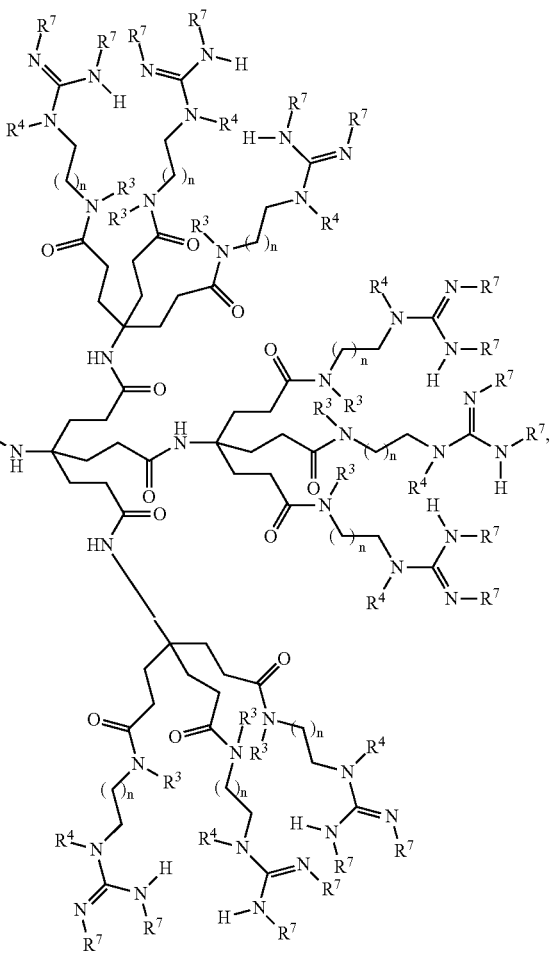

wherein each n is independently an integer from 0 to 9; wherein $R^3$ is hydrogen or alkyl; wherein $R^4$ is hydrogen, or alkyloxycarbonyl, alkyl, or acyl; and wherein $R^7$ is hydrogen or alkyloxycarbonyl.

Figure 32:
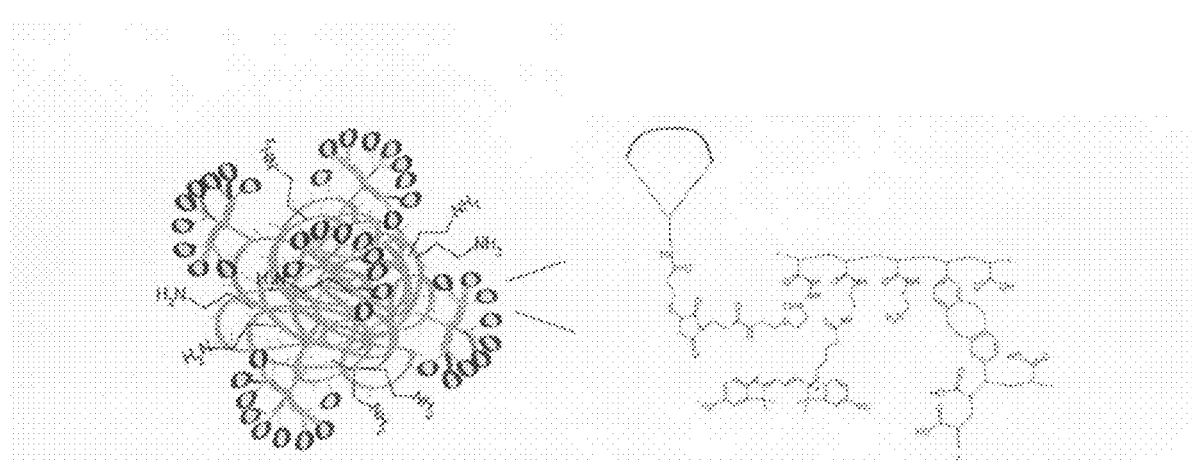
FIG. 32 demonstrates the flexibility of assembly of the disclosed delivery systems.
Figure 33:
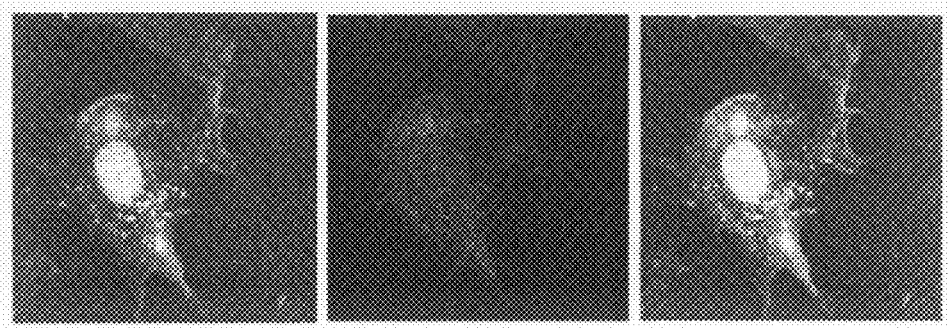
FIG. 33 shows micrographs of HeLa cells exposed 10 µM FD-1 for 1 h, fixed with 3.3% paraformaldehyde, stained with 100 nM Mitotracker® Red 580 FM. The illuminated regions show cell penetration (left), mitochondria location (center), and overlap (right).
Figure 36:
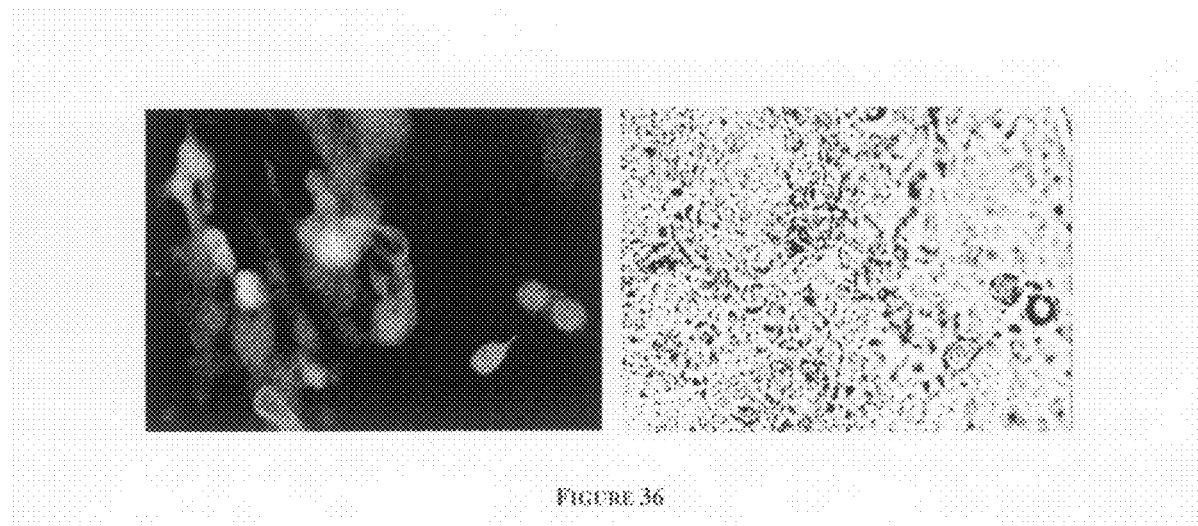
FIG. 36 shows micrographs demonstrating intercellular transport of an aprotinin-fluorophore-transporter conjugate (FD-2) into HAEC cells.
Figure 37:
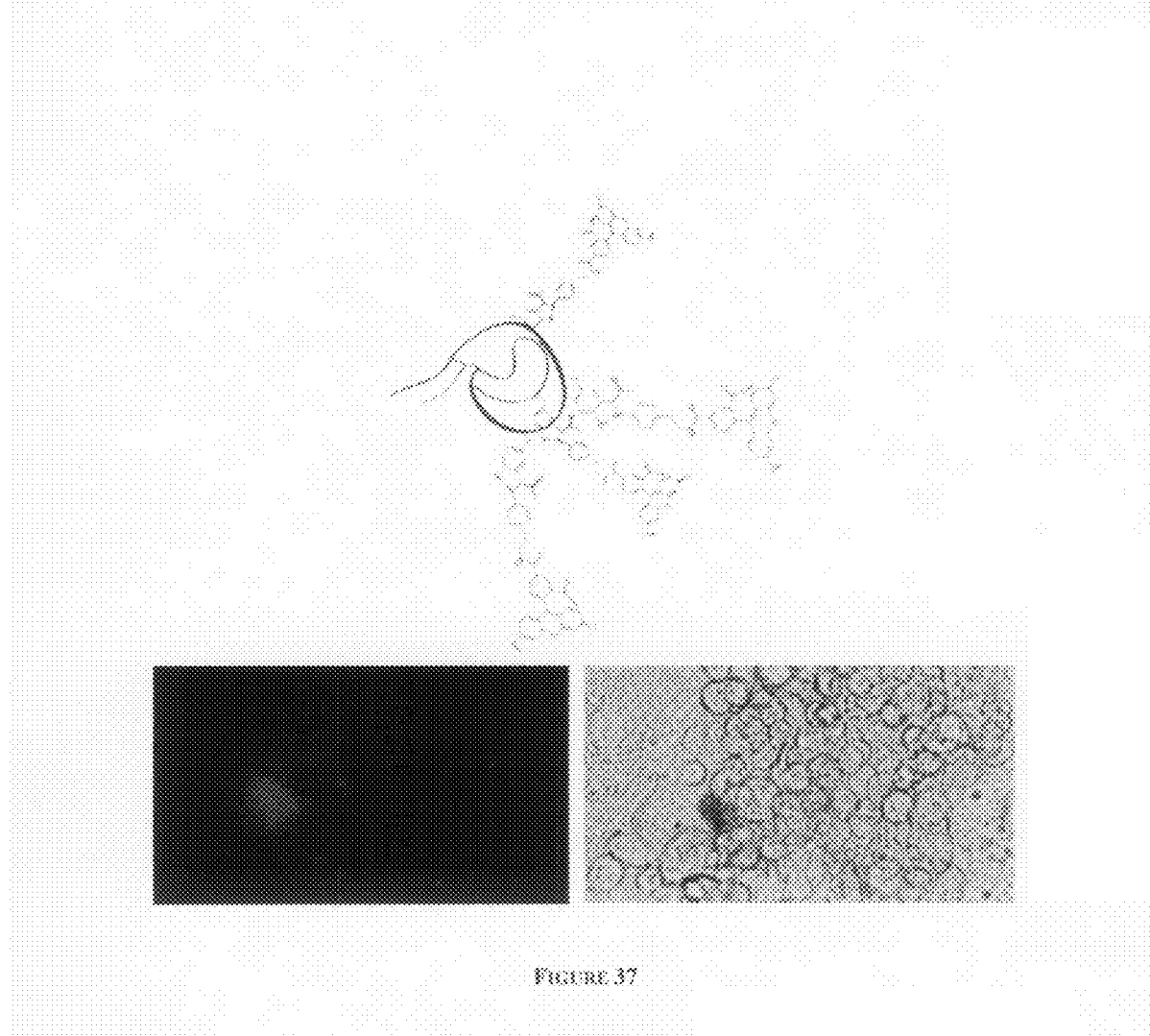
FIG. 37 shows micrographs demonstrating no uptake (i.e., no intercellular transport into HAEC cells) of a control aprotinin-fluorophore conjugate (illustrated).
Figure 38:
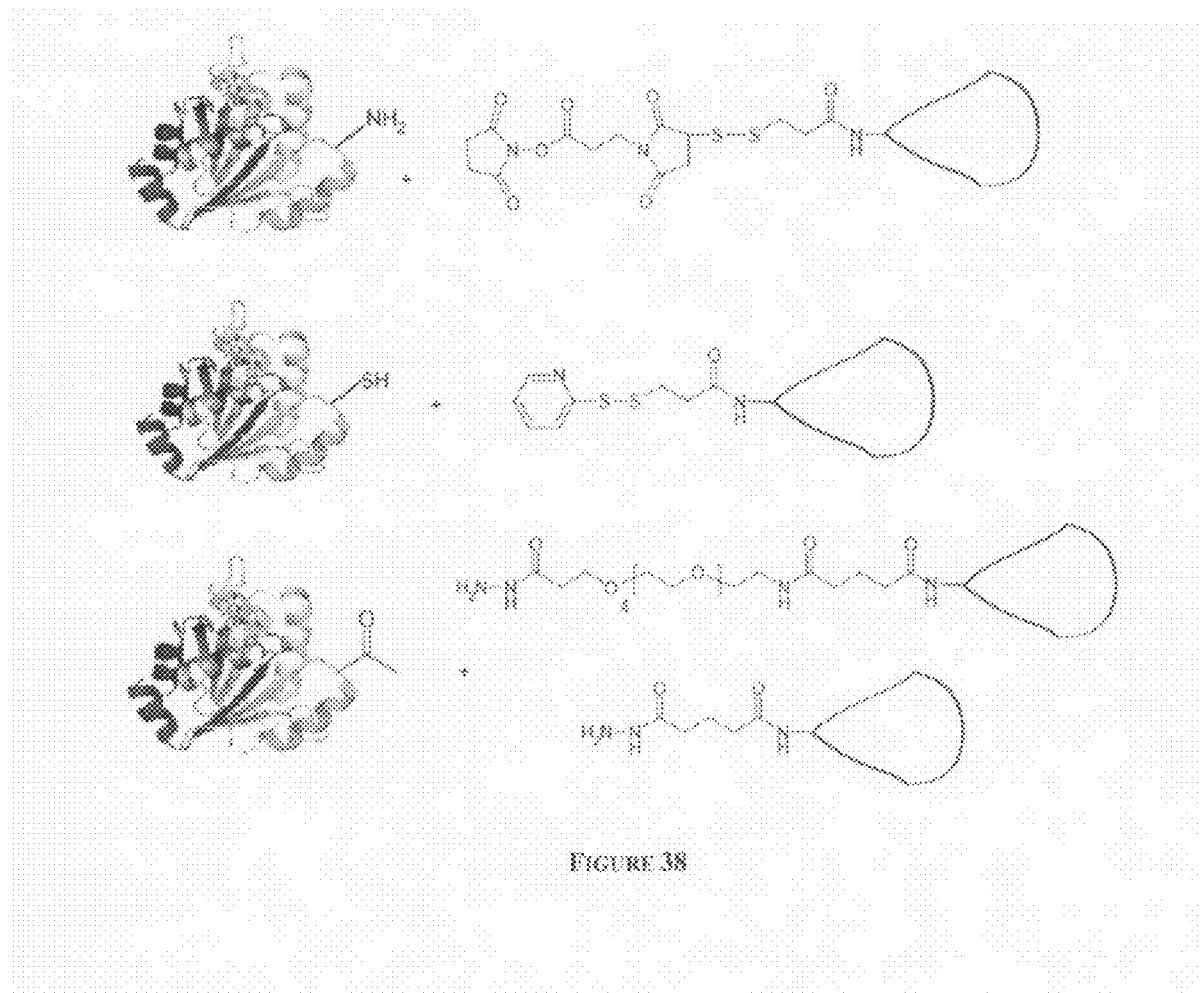
FIG. 38 illustrates several chemical strategies for binding transporter moities to various protein functional groups (e.g., amine, thiol, carbonyl).
Figure 39:
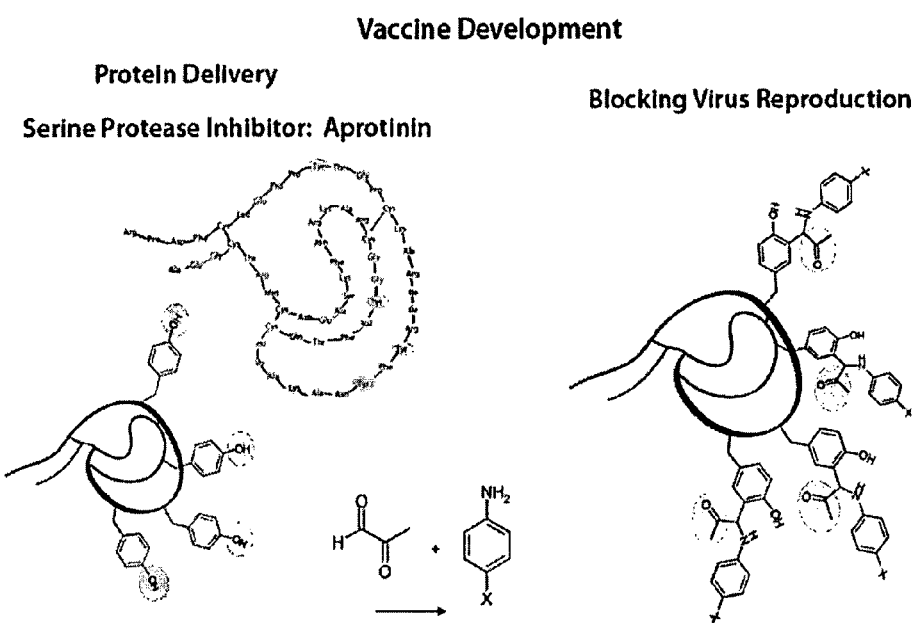
FIG. 39 presents strategies for vaccine development by incorporation of aprotinin through conjugation to carbonyl-functionalized proteins (e.g., tyrosine residues) by Mannich reaction.
Figure 40:
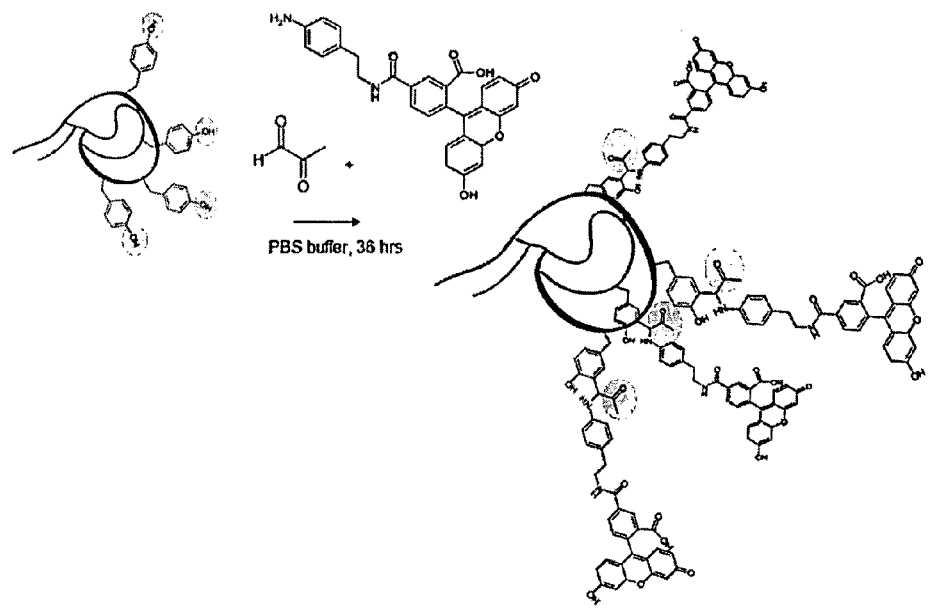
FIG. 40 illustrates incorporation of fluorophores through conjugation to carbonyl-functionalized proteins (e.g., tyrosine residues) by Mannich reaction.
Figure 41:
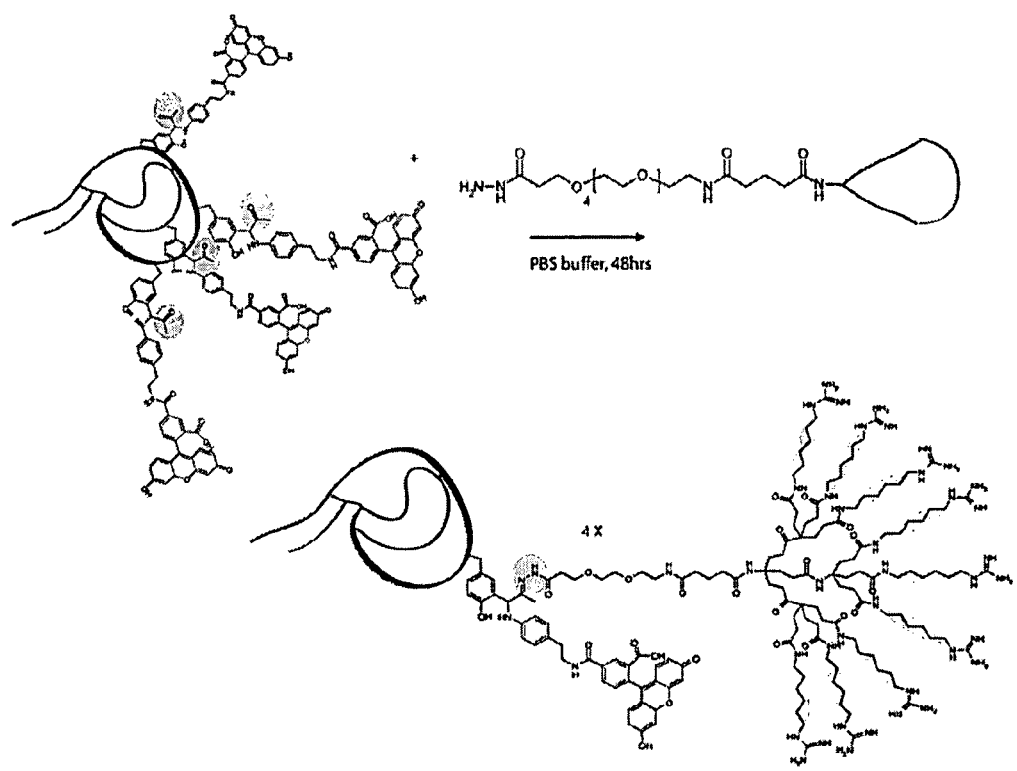
FIG. 41 illustrates incorporation of transporter moieties through conjugation to carbonyl-functionalized proteins.

It is demonstrated that the disclosed transporter (e.g., FD-2, hexyl linker) shows selectivity towards the mitochondria of a cell. (see FIG. 33) The FD-1 shows selectivity towards the cell nucleus (see FIG. 32). A common obstacle in macromolecular drug delivery is the cellular uptake into cell compartments that do not release the drug delivery vector into the cytosol or mitochondria in which the drug becomes effective. Most other delivery pathways into the cell end up in the lysosome and do not get released (endocytosis). The therapeutic efficacy of drug molecules typically depends on its ability to reach desired target tissues, cells and intracellular organelles.

The mitochondria play a key role in apoptosis (cancer therapy), familial amyotrophic lateral sclerosis (ALS, Lou Gehrig's disease), Leber hereditary optic neuropathy (LHON), lactic acidosis, strokelike syndrome (MELAS) Huntington's disease, and Alzheimer's disease, Kearns-Sayre Syndrome (KSS), myoclonic epilepsy, ragged-red fibers (MERRF), cluster of metabolic diseases (SyndromeX), progressive external ophthalmophlegia (PEO) and antioxidants. By targeting the mitochondria, the disclosed compounds, compositions, and methods can play a role in therapy or prevention of disease processes relating to mitochondria function.

When the disclosed transporter is attached to the disclosed nanoparticle, it can enter the cell and also can achieve localization in the entire cell, including the mitochondria. The nanoparticle allows delivering a high drug load and, thus, can facilitate delivery of small and other molecules, such as peptides, nucleotides and such. The structures can be further modified with amines to allow complexation with plasmic DNA and covalent attachment s though covalent approaches. (see FIGS. 24, 25, 26, 27, 28, and 29).

A nanoparticle with a number of molecular transporter moieties conjugated to the periphery crosses the plasmic membrane and localizes in the cytosol and, particularly, in the mitochondria of the cells. Techniques are disclosed that allow the attachment of the molecular transporter the scaffolds that increase the drug load significantly. Attachment to the "bow-tie" structure and/or the attachment to nanoparticles from intramolecular chain collapse techniques also increase the drug load significantly.

The dendritic transporter allows the conjugation of nine bioactive conjugates and the drug load is increased nine fold by attaching a dendric molecule to the focal point of the dendritic molecular transporter (bow-tie). A well-defined macromolecule is designed, that is "clicked" together in a Huisgen type reaction. The deprotection of the basic/acidic protecting groups allows the modification to a delivery system with a short ethyl linker or hexyl linker before guanidylation to maintain uptake into specific subcellular locations. The disulfide linker is only one of the examples of a linker chemistry attached to the drug part of the bow-tie structure. All other linkers presented can be applied as well.

The drug load can be increased nine-fold by attaching a dendric molecule to the focal point of the dendritic molecular transporter (bow-tie). A well-defined macromolecule is designed, that is "clicked" together in a Huisgen type reaction. The deprotection of the basic/acidic protecting groups allows the modification to a delivery system with a short ethyl linker or hexyl linker before guanidylation to maintain uptake into specific subcellular locations.

Here, the drug load can be increased to a theoretical amount of 100-300 positions to conjugate small molecule drugs, peptides, oligonucleotides and more. The functionalization of the particle with a varied amount of amines allows together with the attachment of transporter allows the development of a gene delivery system. A "drug" can also be conjugated though a disulfide bond in a covalent conjugation approach. For example, proteins can be delivered. (see FIGS. 37, 38, 40, and 41).

F. ORGANIC QUANTUM DOTS VIA INTRAMOLECULAR CHAIN COLLAPSE

The synthesis and application of polymeric nanoparticles has attracted significant attention due to, in part, the realization that functionalized nanoparticles can be considered as building blocks for a variety of nanotechnological applications, ranging from vectors for drug and DNA delivery systems to templating agents for nanoporous microelectronic materials. Typical strategies for preparing nanoparticles can be broadly classified into two main approaches, top-down approaches—where emulsion polymerization techniques result in particles from 20 to 50 nm—and bottom-up approaches—which either rely on the synthesis of discrete spherical macromolecules such as dendrimers (1-10 nm) or the self-assembly of linear block copolymers into polymeric micelles followed by chemical cross-linking to give nanoparticles with typical dimensions ranging from 20 to 200 nm. As a consequence, the ability to routinely prepare nanoparticles in the 5-20 nm size range is limited.

To address this issue, strategies involving the collapse and intramolecular coupling of single-polymer chains to give discrete nanoparticles have been developed. However, typical intramolecular chain collapse strategies can fail to provide resultant nanoparticles with satisfactory functionality. Moreover, these strategies can also fail to provide reactive monomers capable of undergoing the requisite intramolecular chain collapse at desirable temperatures and/or under desirable conditions. In contrast, the disclosed methods and compounds address these shortcomings.

1. Copolymers for Intramolecular Chain Collapse

Figure 7:
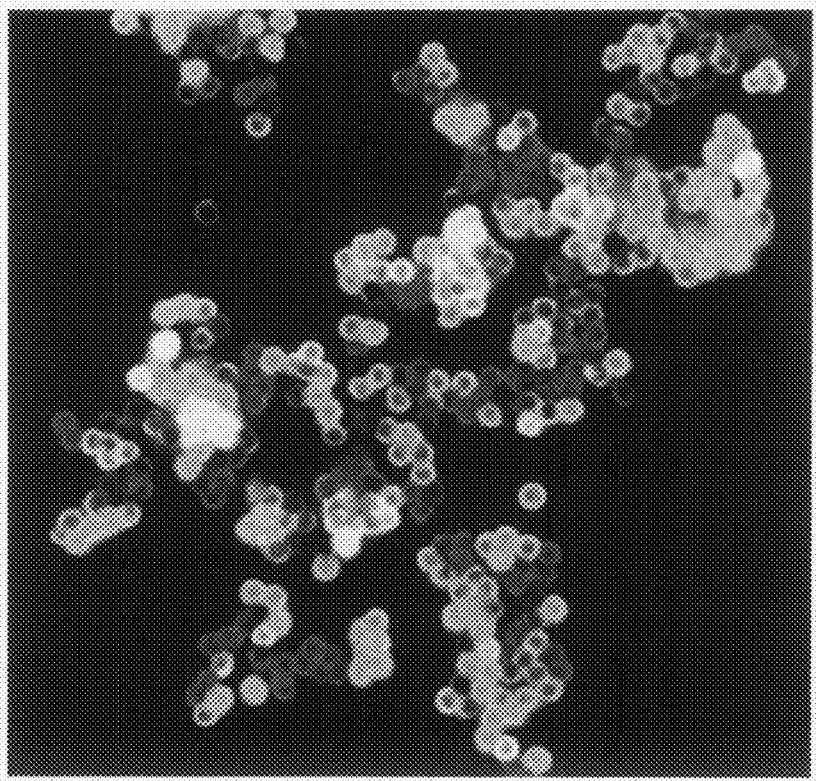
FIG. 7 shows a micrograph of a collection of organic quantum dots formed via intramolecular chain collapse. The various dots are imaged having different colors as a function of the selected functional moiety.
Figure 8:
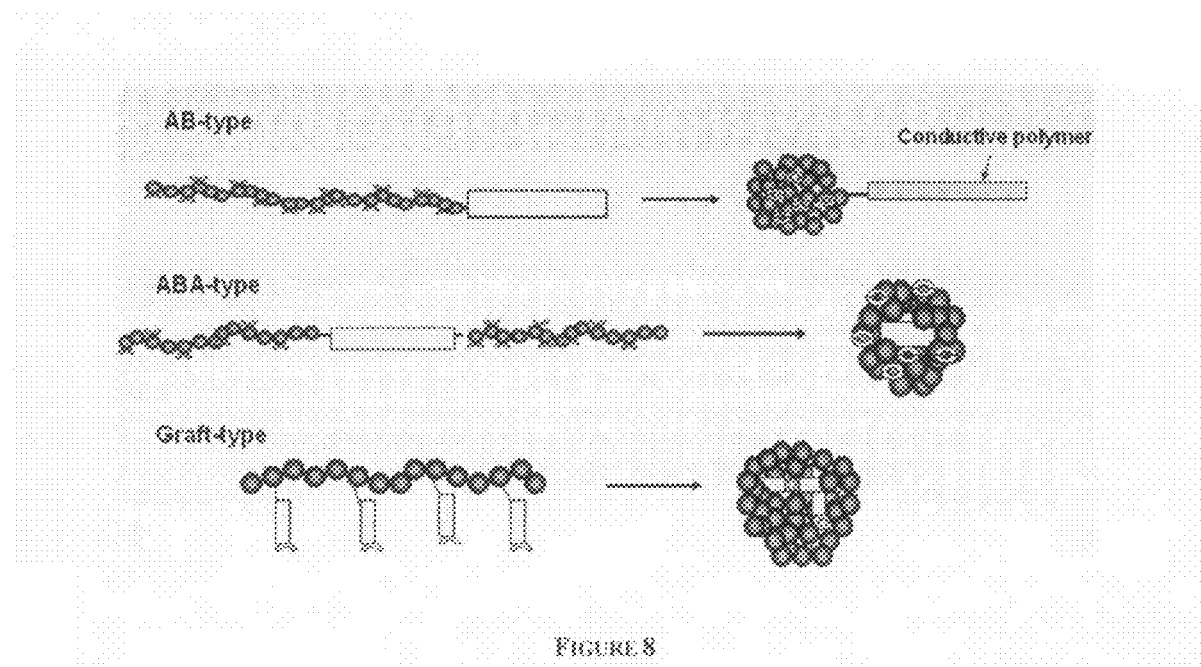
FIG. 8 shows a schematic representation of a synthetic scheme for preparing the various types of disclosed organic quantum dots.
Figure 9:
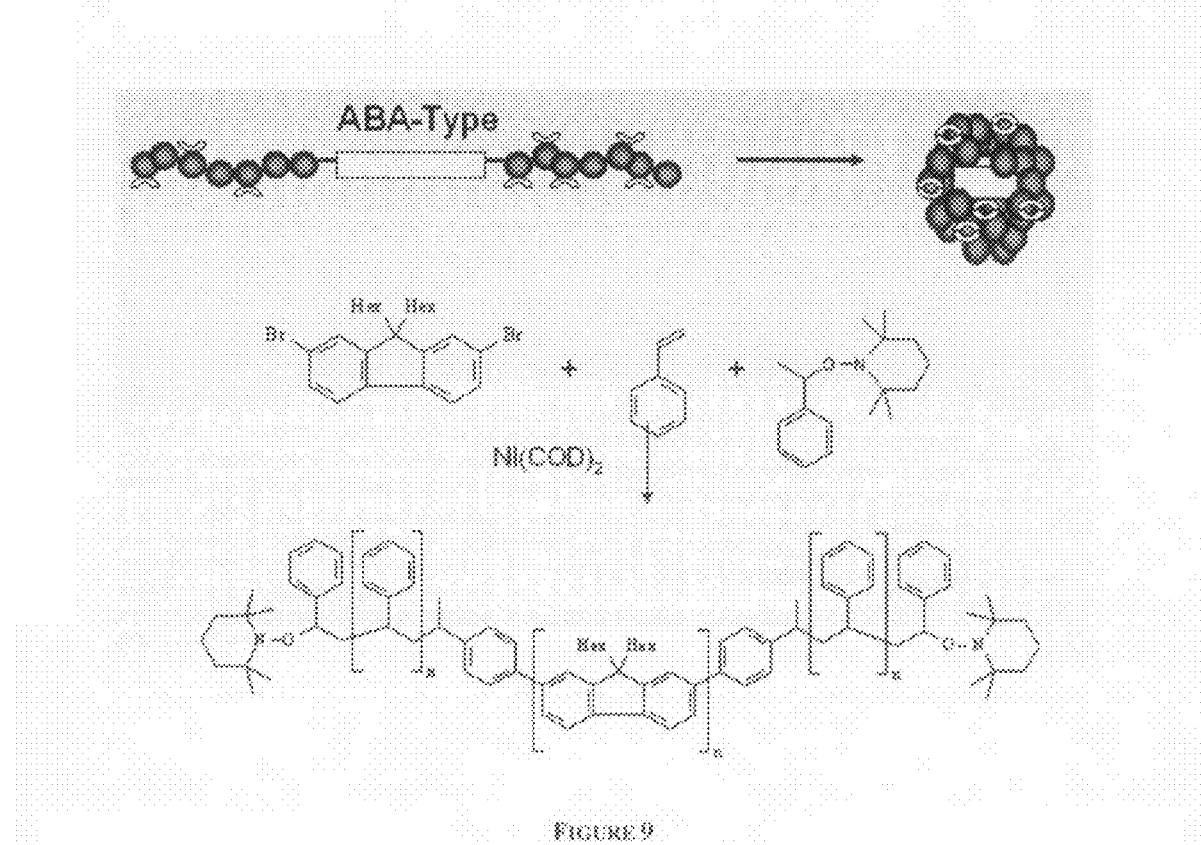
FIG. 9 shows a schematic representation of a synthetic scheme for preparing ABA-type organic quantum dots.
Figure 10:
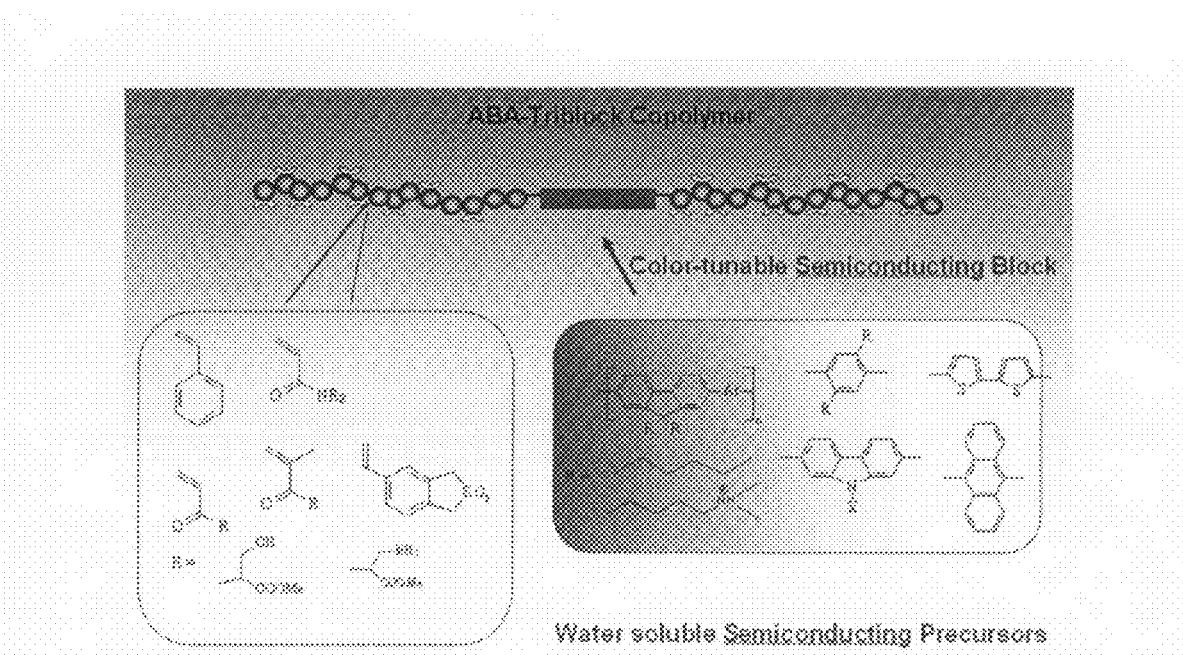
FIG. 10 shows a schematic representation of the composition of an ABA-type organic quantum dot precursor, an ABA triblock copolymer.
Figure 11:
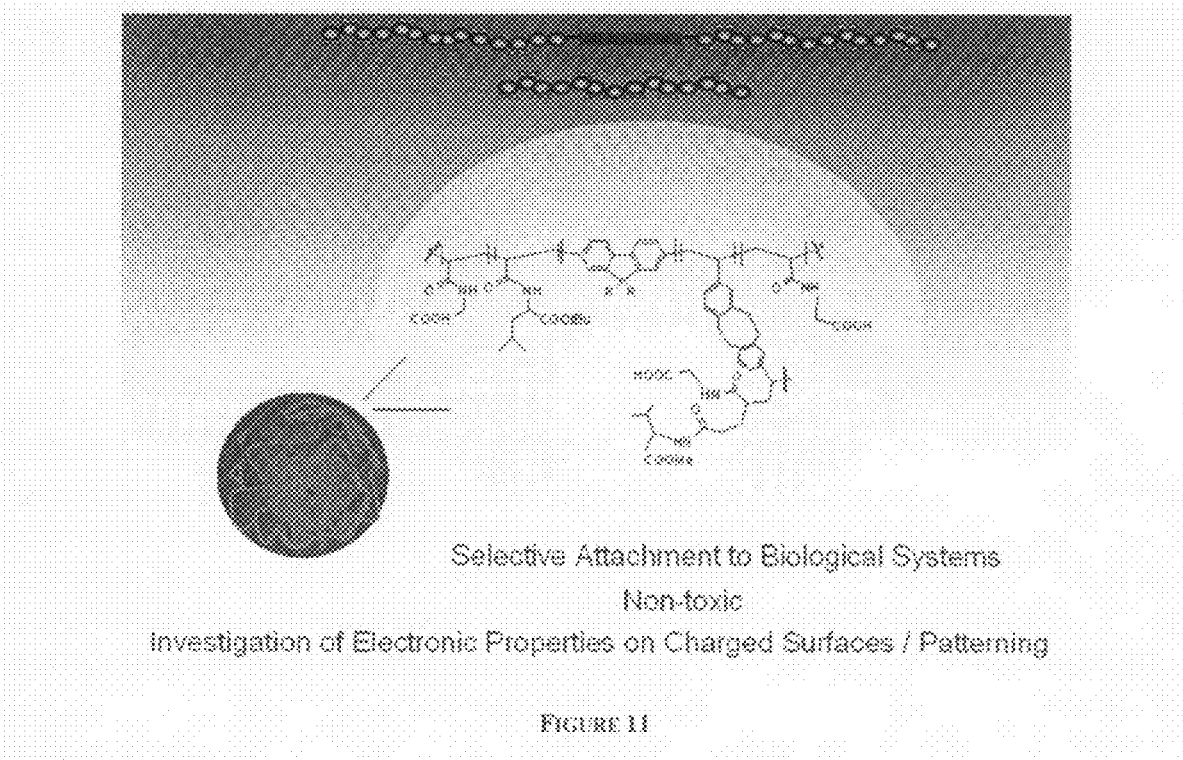
FIG. 11 shows a schematic representation of an organic quantum dot and its applicability as a biological probe and/or a drug-delivery vehicle.

"Organic quantum dots" can be formed from AB-block, ABA-block, and graft-type copolymers via intramolecular chain collapse (see FIG. 7 and FIG. 8). Such organic quantum dots can comprise a functional moiety, e.g. a color-tunable semiconducting block (see FIG. 9, FIG. 10, and FIG. 11). Methods and compositions for preparing copolymers capable of undergoing intramolecular chain collapse are known and described in, for example, Harth et al., "A Facile Approach to Architecturally Defined Nanoparticles via Intramolecular Chain Collapse," *J. Am. Chem. Soc.*, 2002, 124, 8653-8660, which is incorporated herein by reference in its entirety.

The field of living free radical polymerizations, where the high degree of control is a result of equilibrium between dormant and reactive propagating radicals, can be useful for developing strategies for nanoparticle formation. In such polymerizations, the reactive radical chain ends are present in extremely low concentrations. This general concept, that is, only the reactive species need to be at ultra-dilute concentrations, can be applied to the formation of nanoparticles by intramolecular coupling. In this case, the linear polymer, which contains numerous latent coupling groups along the backbone, can be added slowly to a heated solvent in which the coupling groups are either thermally or chemically activated. As a consequence, the traditional conditions of ultra-high dilution typically need only be met for the reactive intermediates and not for the polymers themselves. Following this coupling event, the nanoparticles are typically unreactive to further coupling reaction, which allows their concentration to increase to relatively high levels, (0.1-1.0 M) without intermolecular cross-linking reactions leading to gelation or coupling of individual nanoparticles. The ability to work at 0.1-1.0 M concentrations can be compared to the typically impractical concentration levels (ca. $10^{-6}$ M) required for traditional ultrahigh dilution techniques.

Figure 12:
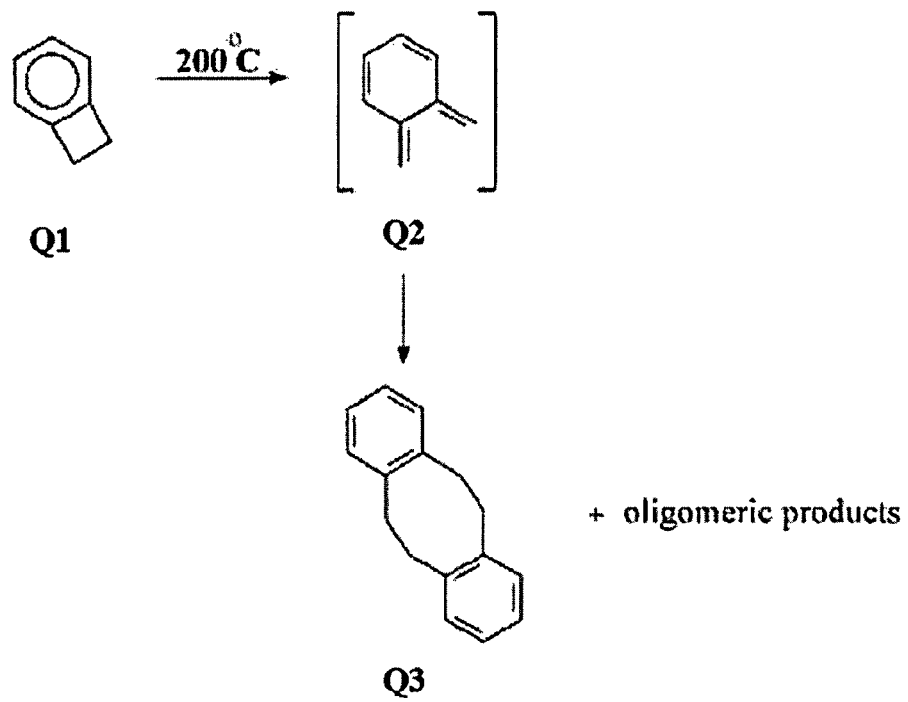
FIG. 12 shows a schematic for coupling reactions of benzocyclobutene derivatives.
Figure 13:
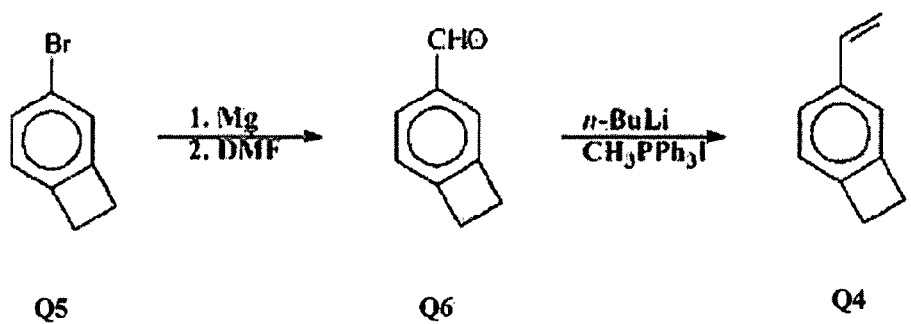
FIG. 13 shows an exemplary synthesis of benzocyclobutene monomer Q4.
Figure 14:
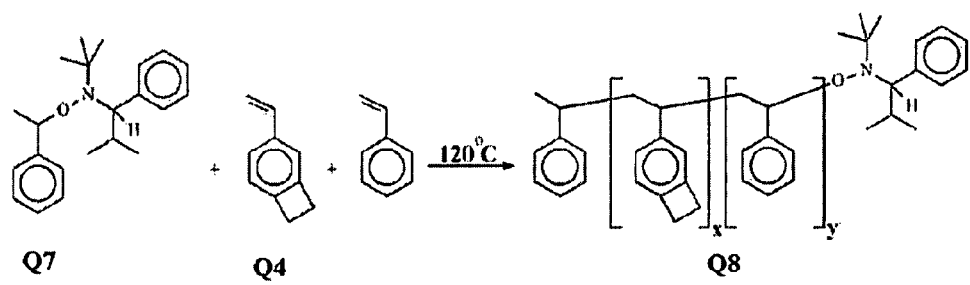
FIG. 14 shows an exemplary synthesis of benzocyclobutene functionalized linear polystyrene Q8.
Figure 15:
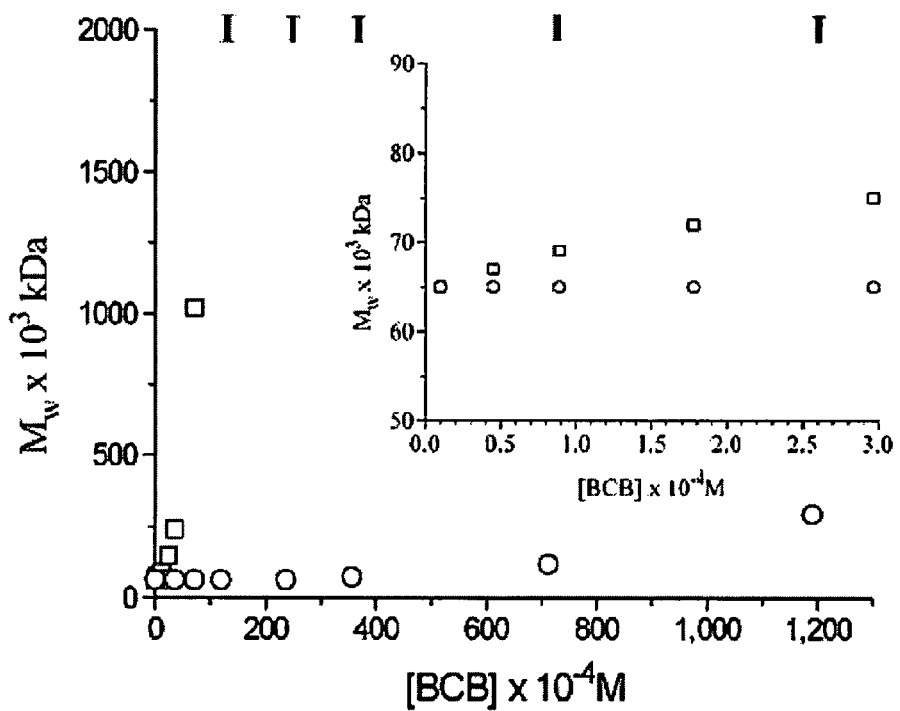
FIG. 15 shows a graph of the variation in molecular weight of final macromolecule, Mw, with total concentration of BCB groups in solution (circles represent ultra-high dilution strategy; squares represent continuous addition strategy; I represents that an insoluble gel was produced) (starting linear polymer, mw=95,000, PDI=1.11).
Figure 16:
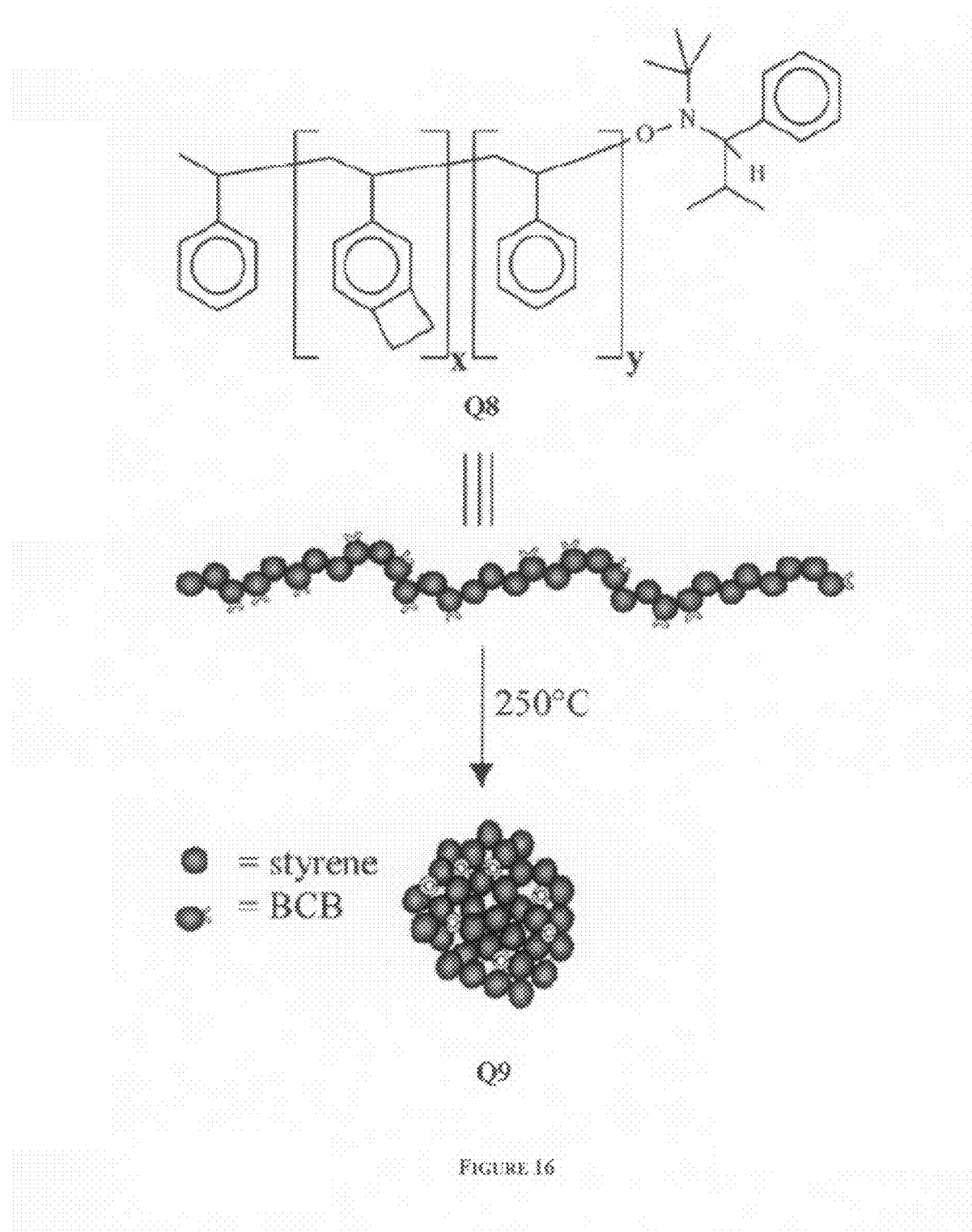
FIG. 16 shows a schematic representation of the intramolecular collapse of the linear polymer Q8 to give the nanoparticle Q9.

The nature of the cross-linking group can be important; it can be selectively activated and react rapidly, leading to efficient intramolecular bond formation. It can also be important that this reaction is irreversible and leads to a coupled structure that is subsequently unreactive under the reaction conditions. To fulfill these goals, attention was directed to the benzocyclobutene group (BCB), which has found wide use as a latent Diels-Alder reagent in organic synthesis and in the formulation of thermosetting materials. Upon heating, the benzocyclobutene group, Q1, undergoes ring opening to give a relatively reactive o-quinoid structure, Q2, which primarily reacts via an irreversible dimerization reaction to form the dibenzocyclooctadiene derivative, Q3, as well as a mixture of unidentified oligomeric materials (FIG. 12). The direct result of this chemistry is the selective formation of cross-links from the coupling of two or more benzocyclobutene units. Having identified the benzocyclobutene functionality as the critical coupling group for the preparation of nanoparticles, the desired monomer, 4-vinylbenzocyclobutene, Q4, was prepared from 4-bromobenzocyclobutene, Q5, by initial Grignard formation followed by reaction with N,N-dimethylformamide to give the aldehyde, Q6. Wittig coupling of Q6 with methyltriphenylphosphonium bromide afforded the desired styrene derivative, Q4, in high yield (FIG. 13). The incorporation of the cyclobutene group into the monomer, Q4, did not decrease its stability when compared to styrene, and Q4 proved to be stable to a wide variety of reaction conditions. One key to the success of this intramolecular chain collapse strategy is the minimization or elimination of intermolecular cross-linking between BCB groups on different chains. Since the balance between intramolecular coupling and intermolecular cross-linking can be influenced by the number and placement of BCB units along the polymeric backbone, accurate control of the starting linear polymers structure also can be important. To achieve this and to permit a wide variety of linear polymers to be conveniently prepared, the polymerization of the desired monomer, 4-vinylbenzocyclobutene, Q4, was examined under living free radical conditions. Copolymerization of Q4 with vinyl monomers such as styrene, methyl methacrylate, or n-butyl acrylate in the presence of the R-hydrido alkoxyamine, Q7, proved to be a controlled procedure, leading to random incorporation of the reactive BCB units and low polydispersities for the resulting copolymers, Q8 (FIG. 14). At molecular weights less than 120000 amu the polydispersities for these random copolymers were 1.08-1.16, which increased to 1.19-1.26 for molecular weights above 200 000 amu. This increased polydispersity is due, at least on part, to the significantly reduced concentration of initiating groups at these high molecular weights and has been observed previously for both ATRP- and nitroxide-mediated procedures. The BCB-functionalized polystyrene derivatives, Q8, can be readily characterized by standard techniques and incorporation of the BCB units monitored by $^1$H NMR which showed characteristic aliphatic resonances for the cyclobutene ring at 3.10 ppm. Intramolecular collapse was then examined under traditional ultrahigh dilution techniques. For this, a solution of a 80:20 styrene/BCB random copolymer, Q8 (Mw=95 000; PDI=1.11) in dibenzyl ether was heated at a variety of concentrations under $N_2$ for 30 min at 250° C. As can be seen in FIG. 15, at very low concentrations of BCB groups, ca. $5.0 \times 10^{-5}$ M (see inset, FIG. 15), intermolecular cross-linking becomes apparent as evidenced by the increase in molecular weight of the product from its base value of 65000 for a discrete nanoparticle due to chain-chain coupling. This ability to readily identify chain-chain coupling has been previously observed for dendrimer chemistry where even minor amounts of intermolecular coupling can be easily detected by gel permeation chromatography (GPC). This ability is due to the molecular weight doubling on chain-chain coupling, and the combination of this feature with the low polydispersity of the initial chains results in a lower limit of ca. 1-2% of intermolecular cross-linking being readily detected as a higher molecular shoulder under standard GPC conditions. At higher concentrations of ca. $9.0 \times 10^{-3}$ M crosslinking to a swollen gel occurs very rapidly due to the large number of BCB functional groups along the polymeric backbone. While these concentrations are comparable to results obtained with other traditional ultra-high dilution techniques, the results are in stark contrast to the continuous addition strategy. In this approach, a concentrated solution ([BCB]=0.2 M) of the same starting linear polymer, Q8, is continuously added via a peristaltic pump to a high-boiling solvent, such as dibenzyl ether, heated at 250° C. to give a final BCB concentration of 0.05 M. After addition, the solvent is removed, and the nanoparticles, Q9, are isolated using normal precipitation techniques (FIG. 16). No gelation or intermolecular crosslinking is observed under these conditions, and only after increasing the final concentration of BCB groups to 0.12 M were minor amounts of nanoparticle coupling observed. The ability to successfully conduct these chain-collapse reactions at final BCB concentrations of 0.01-0.1 M represents an increase of 3-4 orders of magnitude when compared to the traditional ultrahigh dilution strategy (FIG. 15). This permits multigram samples to be prepared on a routine basis with standard laboratory equipment, a dramatic improvement compared to previous approaches.

Figure 17:
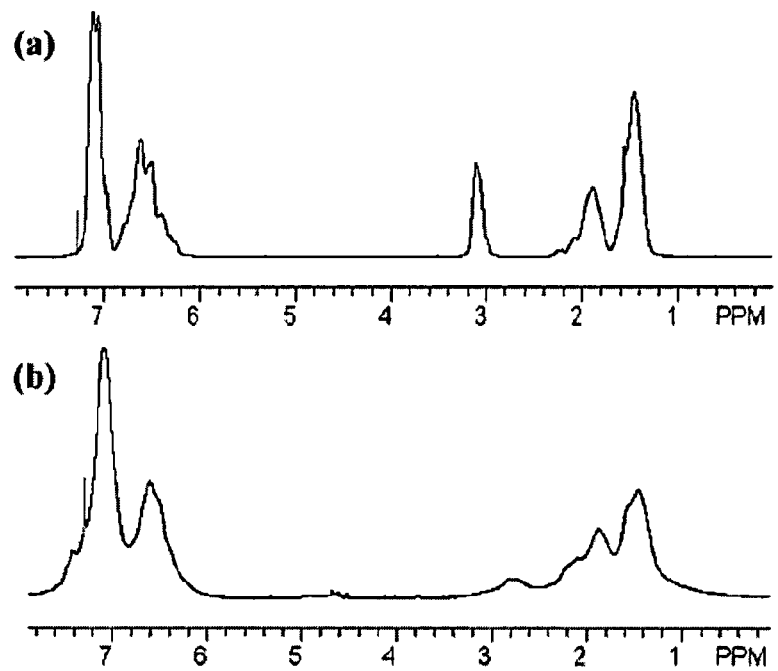
FIG. 17 shows a comparison of $^1$H NMR spectrum for (a) the starting linear polymer, 8, 80/20 Sty/BCB, Mw=95,000, PDI=1.12; and the resulting nanoparticle 9, Mw=65,000, PDI=1.10.

One significant feature of the above concentration studies is the reduction in hydrodynamic volume of the random coil linear polymer on intramolecular collapse to give the final nanoparticle. In the above example, the original linear polymer has a molecular weight, Mw of 95000 amu; however, upon reaction the macromolecule decreases in size to give a nanoparticle with an apparent or polystyrene equivalent Mw of 65000 amu. Dynamic light scattering was also employed to follow this decrease in size, and a reduction in the hydrodynamic radius, Rh from 8.7 to 6.6 nm, was observed upon intramolecular collapse. Since essentially no byproducts are produced during this reaction and no molecular weight lost, this decrease can only be due to a change in the architecture of the macromolecule from a random coil to a nanoparticle. Again, this is consistent with dendrimer chemistry where the compact, three-dimensional dendritic structure leads to an apparent molecular weight which is significantly smaller than the actual molecular weight. Further confirmation of the structural change was obtained from NMR studies; of particular note is the observed absence of unreacted BCB units in the final nanoparticles, Q9. As shown in FIG. 17, comparison of the $^1$H NMR spectra for the starting linear polymer, Q8, and the nanoparticle, Q9, shows the prominent resonance for the aliphatic protons of the cyclobutene group at 3.10 ppm in the former, which completely disappear after collapse, and a broad resonance at 2.0-3.0 ppm is observed. This is consistent with ring opening of the benzocyclobutene group and coupling to give cyclooctane derivatives and higher aliphatic coupled oligomers. A direct consequence of this ring opening is that the BCB groups undergo reaction to give dimers and oligomers that do not undergo any further coupling chemistry. This fulfils one of the requirements discussed above for a successful intramolecular chain collapse reaction and permits the substantial build-up of product in the final reaction mixture. The lack of reactivity can also be demonstrated by repeated thermal cycling of the isolated nanoparticles, which results in no observable change in physical properties such as molecular weight, NMR spectra, and so forth. Formation of the nanoparticles also leads to an increase in the glass transition temperature of the nanoparticles when compared to the starting linear polymers. The BCB functionalized linear polystyrenes, Q8, show Tg's similar to that observed for polystyrene, ca. 100-105° C., while the glass transition temperature for the nanoparticles, Q9, increase by ca. 20° C. to 120-130° C. at 20% BCB incorporation with an associated broadening of the transition. All of the above data is consistent with the intramolecular collapse of a random coil linear polymer to give a single, higher density nanoparticle.

Figure 18:
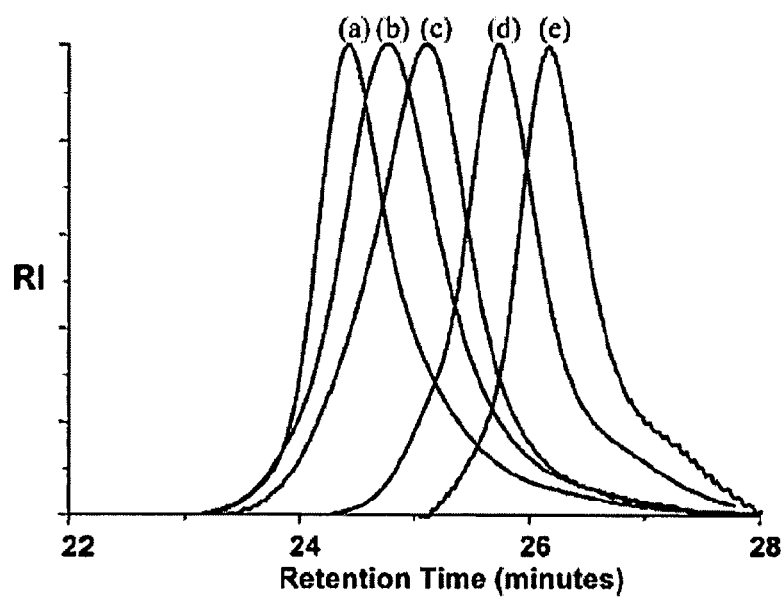
FIG. 18 shows an overlay of GPC traces for (a) the starting linear polymer, Q8, Mw=105000, PDI=1.12; and nanoparticles Q9 with (a) 0 mol % BCB incorporation, (b) 5 mol % BCB incorporation, (c) 10 mol % BCB incorporation, (d) 20 mol % BCB incorporation, and (e) 25 mol % BCB incorporation.

One unique feature of being able to tailor the nanoparticle via the starting linear polymer was then examined in detail using three different series of polystyrene derivatives, ca. 44000; 110000; and 230000 amu containing varying levels of BCB incorporation from 1.25 to 30% (Table 1). Under the continuous addition technique described above, conversion of the linear polymers to nanoparticles was a facile process at all molecular weights and percent BCB incorporations studied. At concentrations of up to 0.01-0.1 M, no indication of intermolecular crosslinking was observed, and in each case the GPC trace shifted to lower hydrodynamic volumes. As can be seen in FIG. 18, for the same molecular weight of the starting linear polymer, Q8, a systematic decrease in the hydrodynamic volume of the nanoparticles is observed on increasing the percent of benzocyclobutene groups, which is consistent with an increase in the level of intramolecular coupling and a more globular, three-dimensional structure. A further pertinent feature of FIG. 18(b-e) is the symmetrical nature/low PDI of the GPC traces for the nanoparticles and the associated lack of higher-molecular weight shoulders. This demonstrates that even at high BCB loadings, ca. 25 mol %, no detectable amount of intermolecular cross-linking is occurring.

TABLE 1

Comparison of the Polystyrene Equivalent Molecular Weights and PDI for the Starting Linear Polymers, Q8, and the Final Nanoparticles, Q9

| | linear | | nanoparticle | | |
|---|---|---|---|---|---|
| composition | Mw | PDI | Mw | PDI | % BCB |
| Sty/BCB | 44000 | 1.09 | 41700 | 1.09 | 2.50 |
| Sty/BCB | 44500 | 1.08 | 38200 | 1.12 | 5.00 |
| Sty/BCB | 45500 | 1.09 | 29100 | 1.11 | 10.00 |
| Sty/BCB | 43500 | 1.10 | 20700 | 1.12 | 15.00 |
| Sty/BCB | 44000 | 1.07 | 18500 | 1.12 | 20.00 |
| Sty/BCB | 110500 | 1.15 | 103000 | 1.17 | 1.25 |
| Sty/BCB | 113000 | 1.12 | 94500 | 1.19 | 2.50 |
| Sty/BCB | 109000 | 1.14 | 79300 | 1.18 | 5.00 |

TABLE 1-continued

Comparison of the Polystyrene Equivalent Molecular Weights and PDI for the Starting Linear Polymers, Q8, and the Final Nanoparticles, Q9

| composition | linear | | nanoparticle | | |
| --- | --- | --- | --- | --- | --- |
| | Mw | PDI | Mw | PDI | % BCB |
| Sty/BCB | 108000 | 1.15 | 59800 | 1.18 | 7.50 |
| Sty/BCB | 112000 | 1.10 | 56000 | 1.19 | 10.00 |
| Sty/BCB | 110000 | 1.16 | 44200 | 1.16 | 15.00 |
| Sty/BCB | 111000 | 1.11 | 42800 | 1.15 | 20.00 |
| Sty/BCB | 112000 | 1.12 | 40500 | 1.09 | 25.00 |
| Sty/BCB | 231000 | 1.23 | 189800 | 1.26 | 1.25 |
| Sty/BCB | 235000 | 1.25 | 174000 | 1.22 | 2.50 |
| Sty/BCB | 228000 | 1.22 | 109000 | 1.26 | 5.00 |
| Sty/BCB | 230000 | 1.19 | 98000 | 1.18 | 7.50 |
| Sty/BCB | 233000 | 1.26 | 91500 | 1.16 | 10.00 |
| Sty/BCB | 231000 | 1.24 | 81000 | 1.17 | 12.50 |
| Sty/BCB | 235000 | 1.23 | 80300 | 1.19 | 15.00 |
| Sty/BCB | 230000 | 1.21 | 66000 | 1.17 | 20.00 |
| Sty/BCB | 229000 | 1.24 | 62000 | 1.25 | 25.00 |
| Sty/BCB | 234000 | 1.23 | 63500 | 1.16 | 30.00 |

Figure 19:
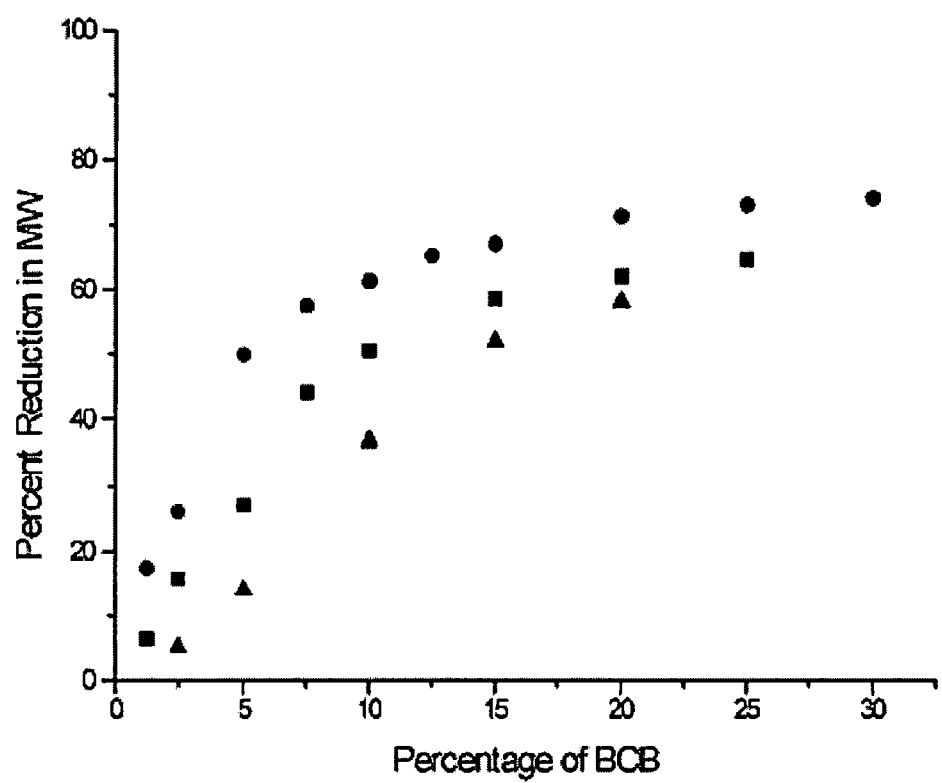
FIG. 19 shows variation in the percent reduction in molecular weight for the nanoparticles Q9 with the mol % of BCB units in the starting linear polymer Q8, for 44 K (b), 110 K (9), and 230 K (b) series.

Analysis of the trends within each series showed that the percent reduction in hydrodynamic volume increases with both increasing molar percentage of BCB and the molecular weight of the starting linear polymer. In each case, the actual molecular weight of the cross-linked macromolecules is significantly greater than the apparent molecular weight. For example, a 70/30 styrene/BCB random copolymer with an initial molecular weight, Mw=234000 (PDI=1.23) gives a nanoparticle with a polystyrene equivalent molecular weight, Mw=63500 (PDI=1.16) which represents a reduction in hydrodynamic volume of 73%. The actual molecular weight of the final nanoparticle was also determined by light scattering and found to be 230000, which is within experimental error of that of the starting linear polymer which demonstrates that the actual molecular weights of the starting linear polymer and the final nanoparticles are approximately the same. This collapse and associated change in hydrodynamic volume is therefore due to the formation of up to 310 intramolecular links per nanoparticle, assuming that each activated BCB group reacts with one other activated BCB group. Interestingly, all plots are of a similar shape and seem to reach a plateau of between 65 and 75% reduction in apparent molecular weight (FIG. 19). It should also be noted that in the control experiments, heating polystyrene with 0% BCB incorporation resulted in no detectable change in the chromatographic or spectral properties of the polymers.

Figure 20:
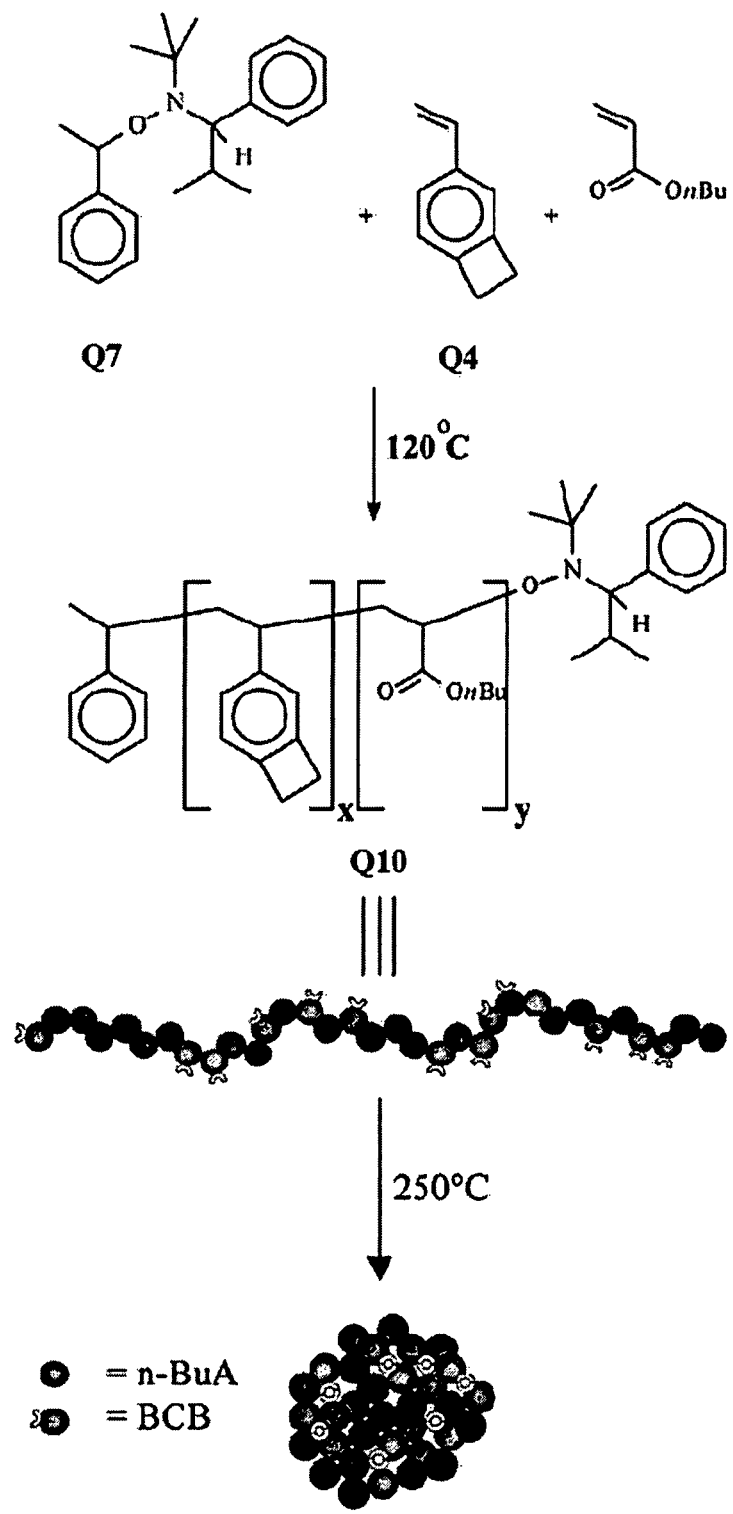
FIG. 20 shows a schematic representation of the intramolecular collapse of a random n-butyl acrylate-based linear polymer, Q10, to give the nanoparticle, Q11.

Examination of the data in Table 1 also demonstrates the inherent versatility of this approach in controlling the size of the final nanoparticle. Not only can the size and cross-link density of the nanoparticle be controlled by the level of BCB incorporation, but the molecular weight of the starting linear polymer also plays a key role in determining the hydrodynamic volume of the final nanoparticle. For example, a polystyrene derivative with a 10% incorporation of BCB and a molecular weight, Mw, of 112000 gives a nanoparticle with a Rh of 6.2 nm. Increasing the molecular weight, Mw, of the starting linear polymer to 233 000 while still retaining the 10% incorporation of BCB gives a larger nanoparticle with a Rh of 9.5 nm. In turn, a polystyrene derivative with an analogously higher molecular weight of 229000 but with a 25% incorporation of BCB gives a nanoparticle with a Rh of 6.4 nm, very similar to the first example with a lower molecular weight (117000) and level of BCB incorporation (10%). A consequence of this is that the size and physical characteristics of the final nanoparticle can be directly dictated by the structure and functionality of the starting linear polymer. The versatile nature of this intramolecular chain collapse approach to nanoparticles coupled with the ability to prepare a wide variety of linear polymers by living free radical techniques also opens up the possibility of preparing well-defined nanoparticles incorporating functional groups, nonstryrenic monomers, or different macromolecular architectures. As shown in Table 2, starting linear polymers based on methyl methacrylate (MMA) or n-butyl acrylate (n-BuA) can be employed as the backbone polymer with no change in the efficiency of the intramolecular collapse process. For example, copolymerization of an 85:15 mixture of n-butyl acrylate and the vinyl BCB derivative, Q4, in the presence of the alkoxyamine initiator, 7, proceeds smoothly to give the well-defined random copolymer, Q10, with a molecular weight, Mw of 75000 and a polydispersity of 1.09. Addition of a concentrated solution of Q10 (0.1 M) to dibenzyl ether, heated at 250° C. gives a poly(n-butyl acrylate) nanoparticle, Q11, with an apparent molecular weight, Mw of 33 500 and a polydispersity of 1.09. (FIG. 20). The relative selectivity of the thermal procedure used to activate the BCB group also allows other functional groups such as chloromethyl substituents to be introduced into the linear polymer, thereby leading to functionalized nanoparticles.

TABLE 2

Comparison of Molecular Weight (Linear Standard Equivalent) and PDI for the Starting Functionalized Linear Polymers, Q10, and the Final Nanoparticles, Q11

| composition | linear | | nanoparticle | | |
| --- | --- | --- | --- | --- | --- |
| | Mw | PDI | Mw | PDI | % BCB |
| MMA/BCB | 52500 | 1.17 | 36500 | 1.14 | 10.00 |
| MMA/BCB | 54500 | 1.12 | 28000 | 1.11 | 15.00 |
| MMA/BCB | 56000 | 1.13 | 26900 | 1.13 | 20.00 |
| n-BuA/BCB | 74500 | 1.10 | 58100 | 1.12 | 5.00 |
| n-BuA/BCB | 77500 | 1.12 | 45700 | 1.14 | 10.00 |
| n-BuA/BCB | 75000 | 1.09 | 33500 | 1.09 | 15.00 |
| n-BuA/BCB | 73000 | 1.09 | 27800 | 1.10 | 20.00 |
| Sty/Cl-Sty/BCB[a] | 101000 | 1.18 | 73500 | 1.20 | 5.00 |
| Sty/Cl-Sty/BCB[a] | 92000 | 1.14 | 48500 | 1.13 | 10.00 |
| Sty/Cl-Sty/BCB[a] | 85000 | 1.14 | 34000 | 1.17 | 20.00 |
| PEG-Sty/BCB[b] | 92000 | 1.13 | 70500 | 1.10 | 5.0 |
| PEG-Sty/BCB[b] | 95000 | 1.11 | 52000 | 1.09 | 10.0 |
| PEG-Sty/BCB[b] | 89500 | 1.12 | 36500 | 1.14 | 20.0 |

[a]10 mol % incorporation of p-chloromethylstyrene
[b]PEG block, Mn = 5000; PDI = 1.06.

Figure 21:
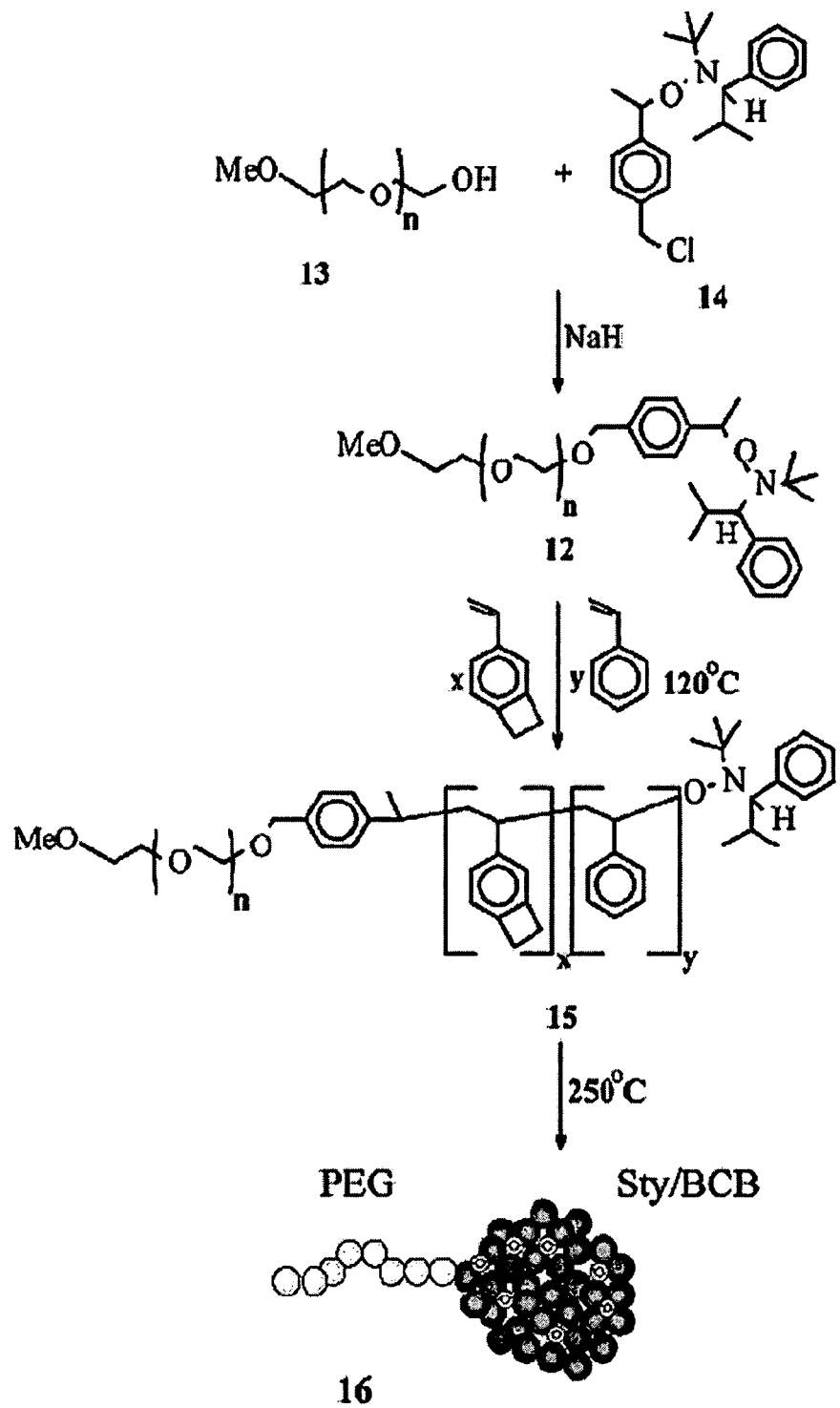
FIG. 21 shows a schematic of the formation and intramolecular collapse of the PEG-b-PSt/BCB block copolymer, Q15, to give a hybrid linear-nanoparticle copolymer, Q16.
Figure 22:
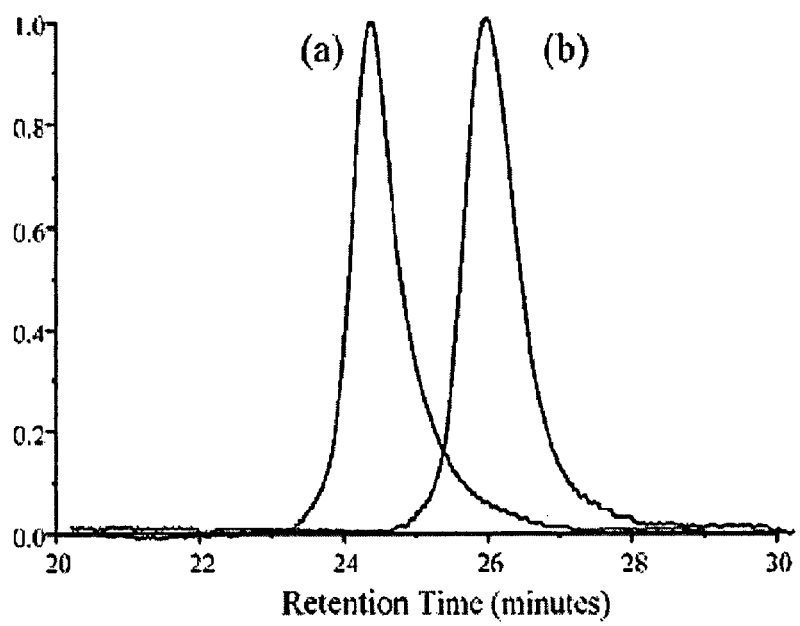
FIG. 22 shows GPC traces for (a) the starting poly(ethylene glycol)-b-poly(styrene-co-benzocyclobutene), Q15, (Mw=95,000, PDI=1.11) and (b) the final hybrid nanoparticle-linear block copolymer, Q16, (Mw) 52,000, PDI=1.09).
Figure 23:
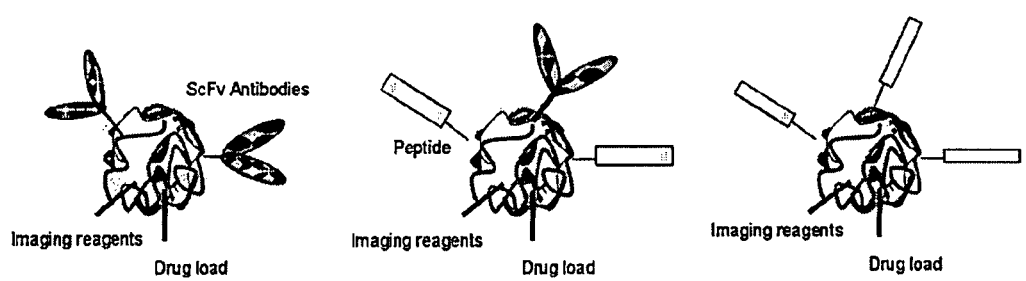
FIG. 23 shows a schematic of exemplary multimodal nanoparticles.
Figure 24:
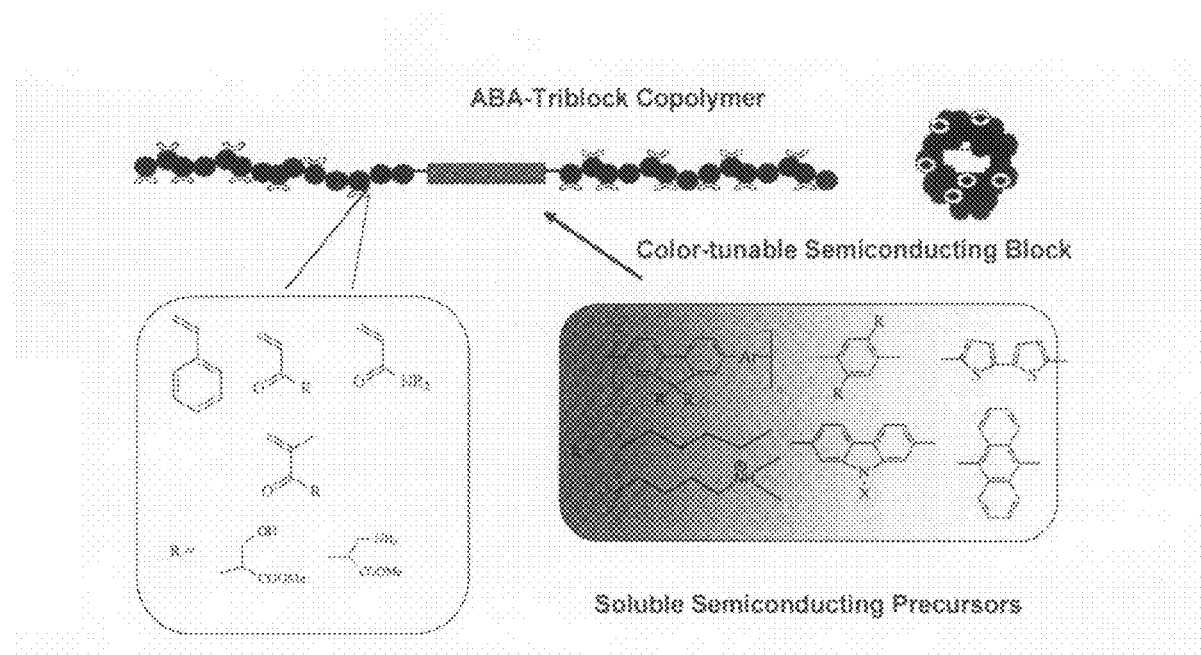
FIG. 24 shows a schematic of an exemplary synthesis of ABA-triblock copolymer linear precursors before and after chain-collapse.
Figure 35:
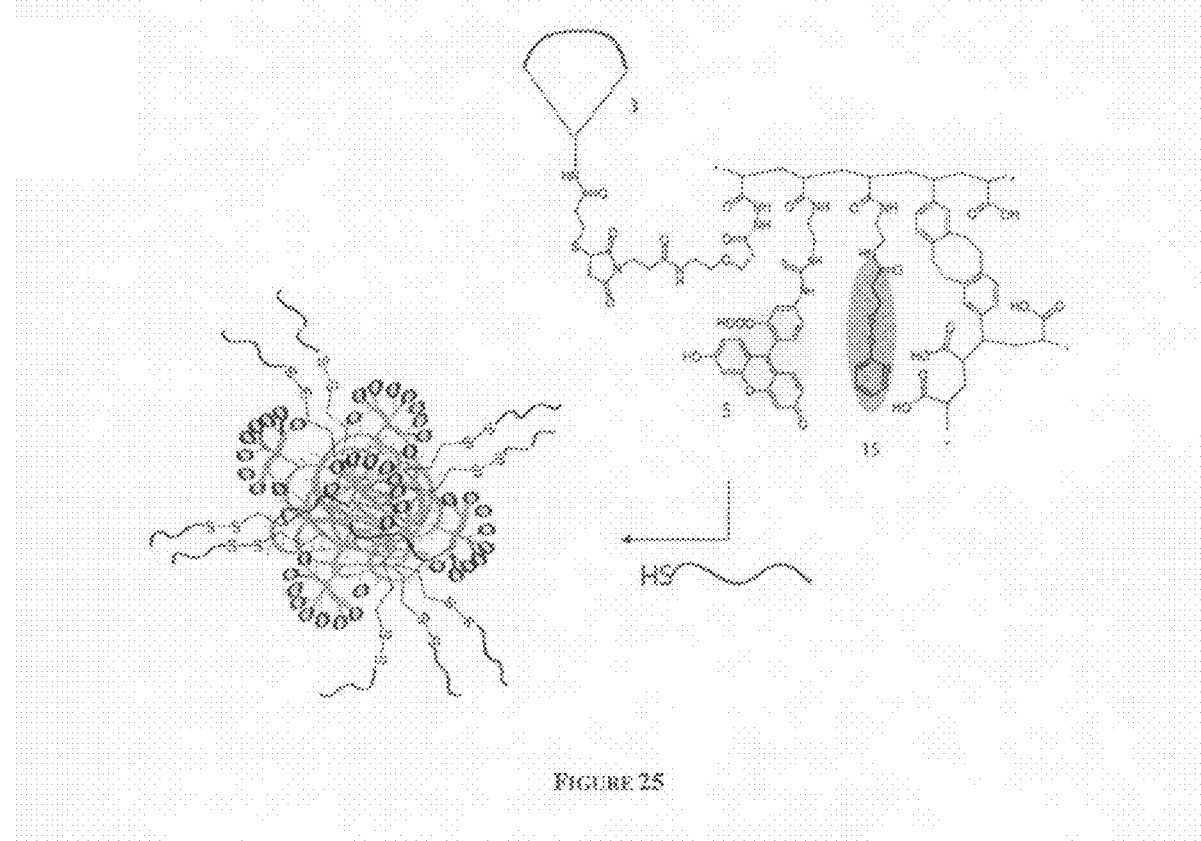
FIG. 35 shows micrographs demonstrating intercellular transport of an aprotinin-fluorophore-transporter conjugate (FD-1, illustrated) into HAEC cells.
Figure 26:
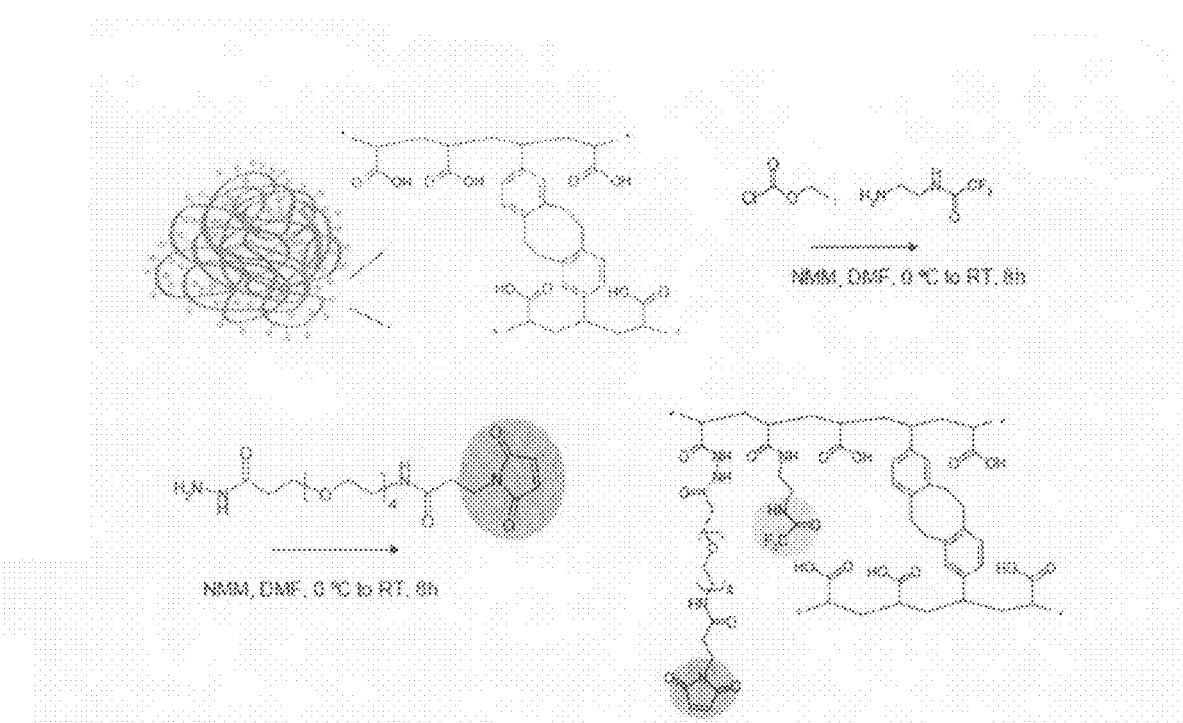
FIG. 26 shows an exemplary preparation of a cross-linked organic nanoparticle.
Figure 27:
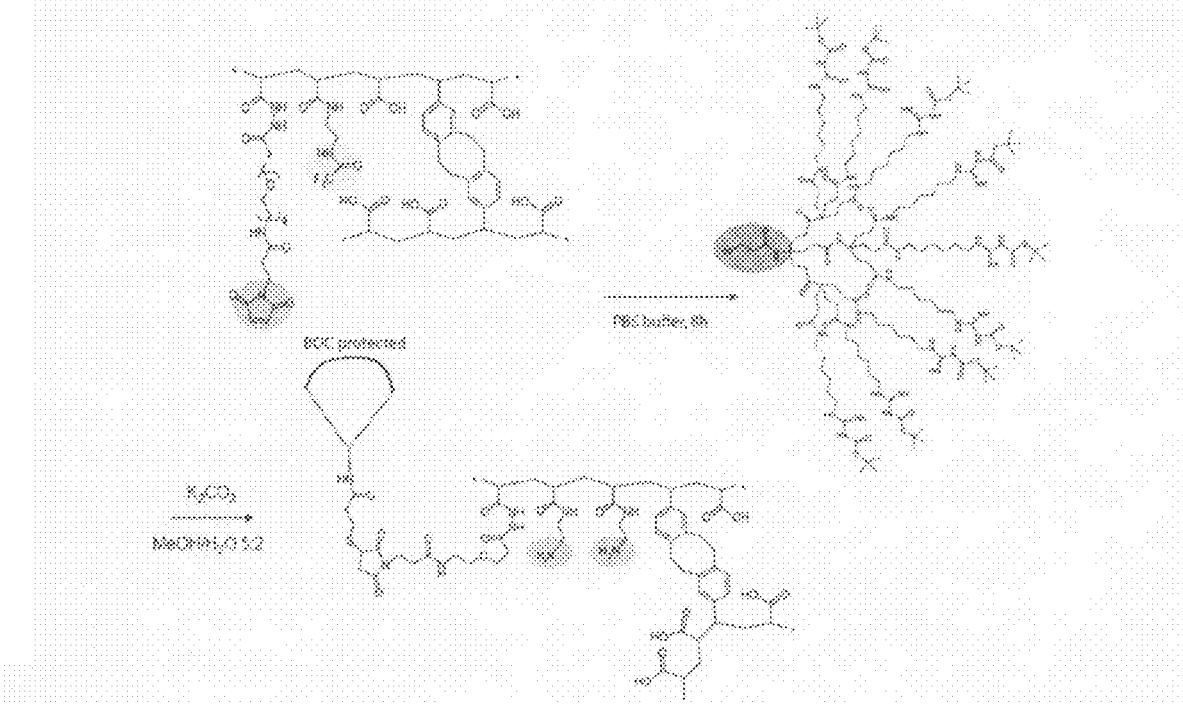
FIG. 27 shows an exemplary conjugation of a disclosed dendrimeric material with a disclosed cross-linked organic nanoparticle.
Figure 28:
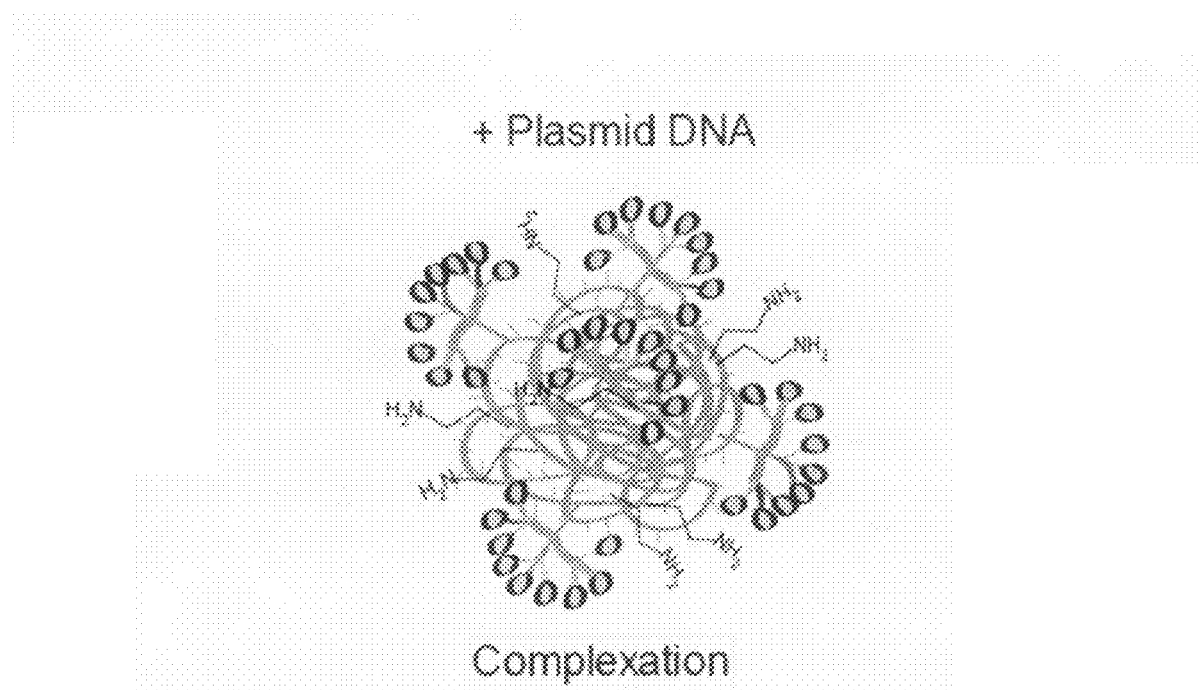
FIG. 28 shows a schematic illustrating a disclosed delivery system (e.g., gene delivery).
Figure 29:
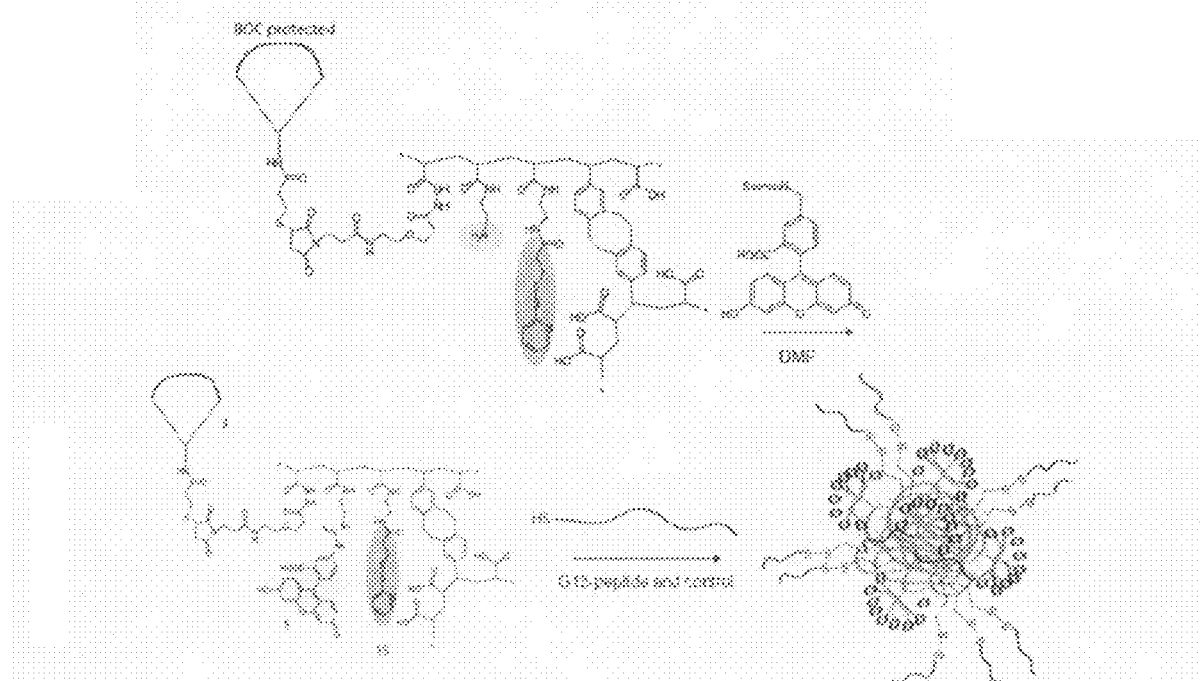
FIG. 29 illustrates preparation of a disclosed delivery system (e.g., gene delivery).
Figure 30:
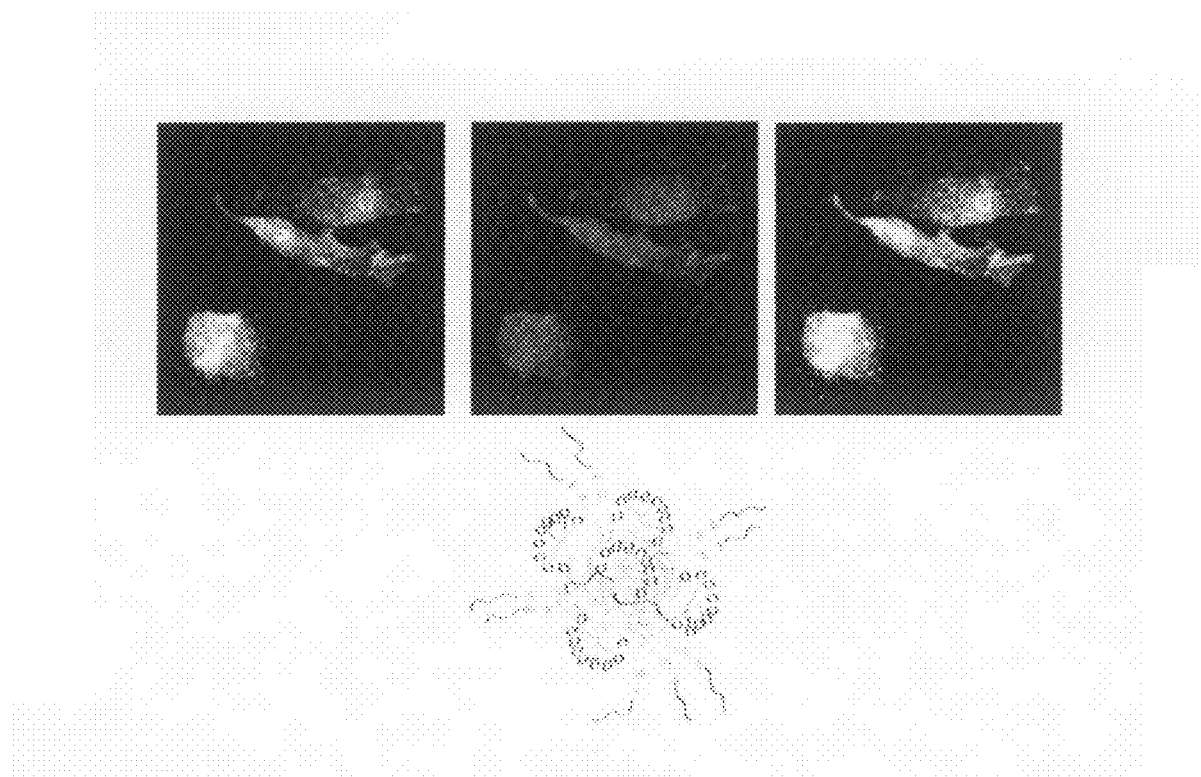
FIG. 30 shows micrographs demonstrating mitochondrial localization of the disclosed delivery systems (e.g., gene delivery).
Figure 31:
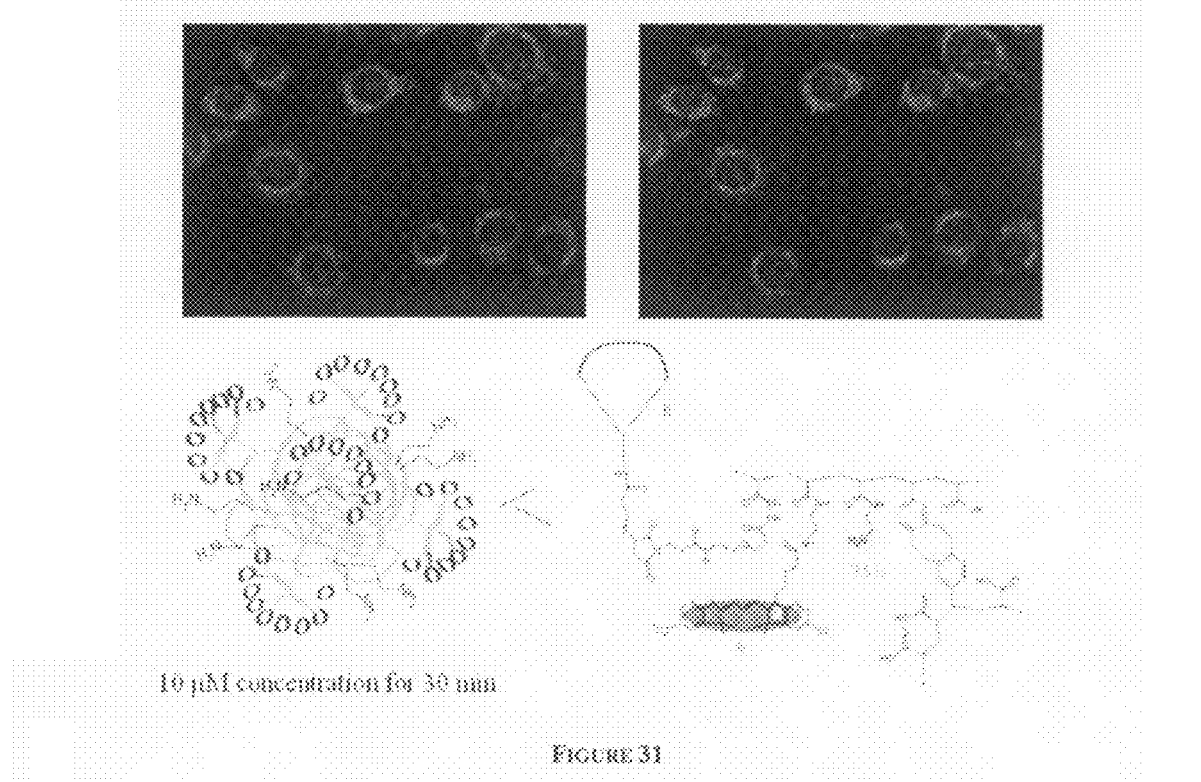
FIG. 31 shows micrographs demonstrating uptake of a disclosed delivery system (e.g., gene delivery) in ciEndothelial cells.

It should, however, be also noted that this intramolecular collapse procedure is not limited to simple linear random copolymers. Additional structural features can be built into the starting materials, which are then translated into the nanoparticle structure. For example, block copolymers can potentially be used in such an approach, and if the reactive BCB groups are contained in only one of the blocks, novel macromolecular architectures can be prepared in which a controlled number of linear chains, one or two for AB and ABA block copolymers respectively, are attached to the nanoparticle. To test this hypothesis, functionalized poly(styrene)-b-poly(ethylene glycol) AB block copolymers were prepared by living free radical procedures. The alkoxyamine substituted poly (ethylene glycol) macroinitiator, Q12, was obtained by reaction of the sodium salt of monomethylpoly(ethylene glycol), Q13 (Mn=5000, PDI=1.06), with the chloromethyl substituted alkoxyamine, Q14. The macroinitiator, Q12, was then used to initiate the polymerization of a mixture of styrene and Q4 at 120° C. to give the desired AB block copolymer, Q15, which contains the cross-linking BCB units in the second block only (FIG. 21). Reaction of Q15 under continuous addition conditions then results in the selective intramolecular collapse of the second block to give a novel hybrid linear-nanoparticle architecture, Q16, in which a single water soluble PEG linear chain is attached to a three-dimensional cross-linked polystyrene nanoparticle, similar in structure to that of hybrid dendritic-linear block copolymers. As can be seen in FIG. 22, the effect of intramolecular collapse is clearly evident in the shift of the GPC trace for the starting poly (ethylene glycol)-b-poly(styrene-co-benzocyclobutene), Q15, (Mw=95000, PDI=1.11) to that of the final hybrid nanoparticle-linear block copolymer, Q16, (Mw=52000, PDI=1.09) and demonstrates the controlled nature of this procedure. The solubility of these hybrid block copolymers were similar to that for the parent polystyrene nanoparticles, which can be due to the relatively small size of the PEG block.

2. Approaches in the Development of 3-D Nanoscopic, Multimodal Vectors

Nanoscopic particle design strategies (see, e.g., Huang, H.; Remsen, E. E.; Kowalewski, T.; Wooley, K. L. *J. Am Chem. Soc.* 1999, 121, 3805.) to develop multimodal architectures are still limited, and the understanding of key problems in biology and medicine will be one of the driving forces to implement materials to execute biological functions. See Lui, M.; Fréchet, J. M. J. *Pharm. Sci. Technol. Today.* 1999, 2, 393. The same care used for these designs can be applied to polymeric nanostructures with applications in imaging and device technologies.

First, highly versatile, biocompatible, building blocks from vinyl polymers with pendant amino acids as linear precursors were prepared. The approach mimics and facilitates pathways mediated in nature and allows the construction and investigation of collapsed supramolecular objects as well as nanoparticles with distinct and permanent shapes. These multifunctional nanoparticles are poised to become powerful tools for the targeted drug delivery with ScFv antibodies directed towards radiation-inducted antigens within the microvasculature. See Hallahan, D.; Geng, L.; Qu, S.; Scafone, C.; Giorgio, T.; Donnely, E.; Gao, X.; Claton, J. *Cancer Cell.* 2003, 3, 63. Lu, S. X.; Cebe, P.; Capel, M. *Macromolecules* 1997, 30(20), 6243. Multiple functionalities within the polymer backbone allow the attachment of anticancer drugs and the complexation of imaging reagents which engage the catechol units, including MRI reagents and radioactive compounds. As mentioned above, one result of this work is the development of synthetic platforms which hold the potential to be multifaceted in their application. The chemistries, which were applied, provide the opportunities to make pioneering steps towards "organic quantum dots" in the nanoscopic range of 5-15 nm and 60-100 nm. It is also contemplated that the incorporation of lanthanides can make these particles attractive objects to study in terms of their magnetic and fluorescent properties.

The synthesis of the multifunctional, biocompatible 3-D nanoparticles began with the preparation of random copolymers with pendant aminoacids. See Hatanaka, K. Y.; Miyahara, S.; Sato, T.; Ono, F.; Uryu, T.; Kuzuhara, H. *J. Med. Chem.*, 1987, 30, 810. Living free radical techniques were applied, such as nitroxide-medicated polymerization (NMP; see Smolders, W.; Monteiro, M. J. Macromolecules, 2004, 12, 34. Hawker, C. J.; Bosman, A.; Harth, E. *Chem. Rev.* 2001, 101, 12.) as well as Reversible Addition Chain Transfer Fragmentation (RAFT). N-Acryl amino acids gave polymers with narrow molecular weight distributions with polydispersities in the range of 1.15-1.28. The most successful RAFT polymerizations were observed in the presence of 2-cyanopentanoic acid dithiobenzoate as a dithioester chain transfer reagent. See Croce, T., Funk, M.; Adkins, C.; Harth, E. *Poly.Prep*, ACS Fall 2005. In experiments with NMP techniques, similar control was observed, but the polymerization appeared to be more sensitive towards the selected monomer conformation. The formation of the 3-D structures can be realized with the new vinyl benzosulfone crosslinking units, which result in non-reversible C—C bonds and are powerful alternatives to the well-known benzocyclobutene precursor. See Harth, E.; van Horn, B.; Lee, V. Y.; Germack, D. S.; Gonzales, C. P.; Miller, R. D.; Hawker, C. J. *J. Am. Chem. Soc.* 2002, 123, 8653. The nanoparticles in the range of 10-14 nm can be functionalized with spacer units to provide the optimum specific binding to expressed neo-antigens and show functionalities for the attachment of fluorophores for the first round of studies. The novel crosslinker was incorporated as well into vinyl polymer backbones growing from a fluorine-based (see McGehee, M.; Heeger, A. *Adv. Materials*, 200, 1655.) macroinitiator via NMP polymerization. The polystyrene blocks contained 10% crosslinking units and the resulting polymer could be prepared in the targeted MW of 20K (2:1:2).

3. o-Chinodimethane Crosslinking Precursors

Benzosulfone derivatives can serve as precursors for o-chinodimethane intermediates to form nanoparticles via an intramolecular chain collapse process. In a five-step synthesis the sulfone functionality was introduced over the oxidation of sulfides formed by a nucleophilic substitution reaction of 3,4-dimethyl benzobromine. A Heck Reaction can serve as an excellent method to transform the arylbromine derivative into the final vinylbenzosulfone in one step. The compatibility of the novel crosslinker towards living free radical polymer procedures can be confirmed, and the formation of monodisperse nanoparticles demonstrated the feasibility of the new crosslinker.

The number and diversity of techniques to create well defined polymeric architectures has led the foundation to built more refined structures with multifaceted, cross disciplinary applications. The fascination to prepare 3-D nanostructures stems from the desire to benefit from the shape and thereby the function in a biological environment or artificial system. In order to control a range of different size dimensions in the nanoscale a number of techniques have been recently successfully investigated and applied. Recently, the synthesis of nanoparticles in the size dimension of 5-10 nm was reported implementing an intramolecular chain collapse process of one linear polymer. The folded linear polymer is locked into the 3-D architecture by covalent crosslinking units incorporated into the polymer. The copolymerized crosslinking units are thermally activated and form a highly reactive o-chinodimethane unit from benzocyclobutene derivatives. However, the copolymerized crosslinking monomer, vinyl benzocyclobutene is not easily accessible and requires a multistep synthesis with over all low yields. In response to the demand to find alternative crosslinking units with the same features but more convenient synthesis, benzothiophen-dioxide derivatives as potenial o-chinodimethane precursors were identified. Benzothiophene derivatives are well known structures to from o-chinodimethanes upon heating at 250° C. under the loss of $SO_2$ and can be prepared in a number of different ways described in the literature. In contrast to known benzothiophene derivatives, a novel brome substituted benzothiophen-dioxide derivative was converted into the desired vinylbenzodevivate crosslinking monomer. In order to overcome difficult synthetic steps, a one step procedure was developed in which a modified Heck coupling reaction provides the vinyl derivative in high yields. Additionally, this novel reaction can be applied to the preparation of other monomer and is poised to open up novel opportunities to combine the crucial vinyl functionality to perform living free radical polymerization procedures with demanding moieties for the further utilization of macromolecules. The novel benzosulfone crosslinking unit was proved to be compatible with standard living free radical polymerization conditions. The intramolecular chain collapse process of polystyrene polymers with a variety of crosslinking units gave well defined monodisperse nanoparticles in the 5-10 nm dimension.

4. Compounds a. Reactive Moieties

In one aspect, the invention relates to a compound comprising the structure:

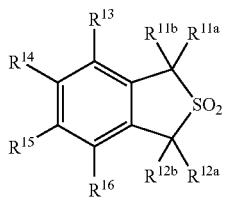

wherein $R^{11a}$, $R^{11b}$, $R^{12a}$, and $R^{12b}$ are, independently, hydrogen, alkyl, alkoxyl, acyl, or carbonyl; wherein $R^{13}$, $R^{14}$, $R^{15}$, and $R^{16}$ are, independently, hydrogen, alkyl, alkenyl, alkynyl, alkoxyl, acyl, or carbonyl, with the proviso that at least one of $R^{13}$, $R^{14}$, $R^{15}$, or $R^{16}$ is a polymerizable group; and wherein the compound eliminates $SO_2$ to form a reactive intermediate at a reaction temperature. In a further aspect, at least one of $R^{13}$, $R^{14}$, $R^{15}$, and $R^{16}$ is alkenyl or alkynyl. In a yet further aspect, $R^{14}$ is vinyl. In a still further aspect, $R^{11a}$, $R^{11b}$, $R^{12a}$, and $R^{12b}$ are hydrogen. In a still further aspect, $R^{14}$ is vinyl and $R^{13}$, $R^{15}$, and $R^{16}$ are hydrogen.

In one aspect, the compound comprises the structure:

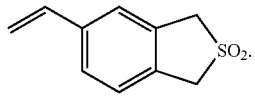

In a further aspect, the compound undergoes polymerization at a polymerization temperature. In one aspect, the polymerization temperature is less than the reaction temperature. In a further aspect, the reaction temperature is less than about 250° C. In a still further aspect, the reaction temperature is less than about 225° C. In a yet further aspect, the reaction temperature is less than about 200° C. In a further aspect, the reaction temperature is less than about 175° C. In a still further aspect, the reaction temperature is from about 175° C. to about 250° C.

In one aspect, the invention relates to a compound comprising the structure:

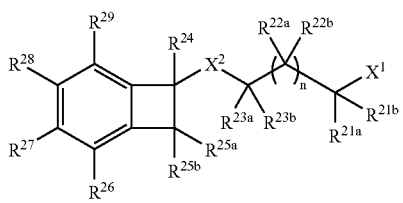

wherein $X^1$ is hydroxyl, primary amino, secondary amino, tertiary amino, thiol, or carboxyl; wherein n is zero or a positive integer; wherein $R^{21a}$, $R^{21b}$, $R^{22a}$, and $R^{22b}$, $R^{23a}$, and $R^{23b}$ are, independently, hydrogen, alkyl, alkoxyl, acyl, or carbonyl; wherein $X^2$ is oxygen, secondary nitrogen, tertiary nitrogen, or sulfur; wherein $R^{24}$, $R^{25a}$, $R^{25b}$, $R^{26}$, $R^{27}$, $R^{28}$, and $R^{29}$ are, independently, hydrogen, alkyl, alkenyl, alkynyl, alkoxyl, acyl, or carbonyl; and wherein the cyclobutane ring undergoes ring opening to form a reactive intermediate at a reaction temperature.

In a further aspect, n is an integer from 0 to 4. In a yet further aspect, n is 0, 1, or 2. In a still further aspect, $X^2$ is oxygen. In a further aspect, $R^{24}$, $R^{25a}$, and $R^{25b}$ are hydrogen. In a yet further aspect, $R^{24}$, $R^{27}$, $R^{28}$, and $R^{29}$ are hydrogen.

In a further aspect, the compound comprises the structure:

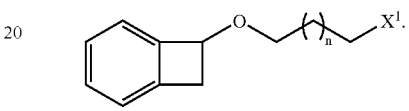

In a further aspect, n is 0, 1, or 2. In a yet further aspect, the reaction temperature is less than about 150° C. In a still further aspect, the reaction temperature is less than about 125° C. In a yet further aspect, the reaction temperature is less than about 115° C. In a still further aspect, the reaction temperature is less than about 110° C. In a further aspect, the reaction temperature is from about 100° C. to about 150° C.

In a further aspect, the invention relates to a polymer or an oligomer comprising at least one residue of at least one disclosed compound.

b. Compounds Capable of Forming an o-Quinoid Moiety

In a further aspect, the invention relates to a compound capable of forming a reactive intermediate comprising an o-quinoid moiety at a reaction temperature of less than about 175° C. In a further aspect, the reaction temperature is less than about 150° C. In a yet further aspect, the reaction temperature is less than about 125° C. In a still further aspect, the reaction temperature is less than about 115° C. In one aspect, the reaction temperature is less than about 110° C. In a further aspect, the reaction temperature is from about 100° C. to about 150° C.

In a further aspect, the compound comprises the structure:

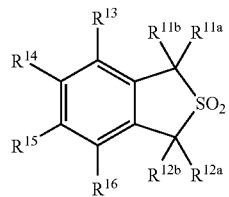

wherein $R^{11a}$, $R^{11b}$, $R^{12a}$, and $R^{12b}$ are, independently, hydrogen, alkyl, alkoxyl, acyl, or carbonyl; wherein $R^{13}$, $R^{14}$, $R^{15}$, and $R^{16}$ are, independently, hydrogen, alkyl, alkenyl, alkynyl, alkoxyl, acyl, or carbonyl, with the proviso that at least one of $R^{13}$, $R^{14}$, $R^{15}$, or $R^{16}$ is a polymerizable group; and wherein the compound eliminates $SO_2$ to form a reactive intermediate at a reaction temperature.

In a further aspect, the compound comprises the structure:

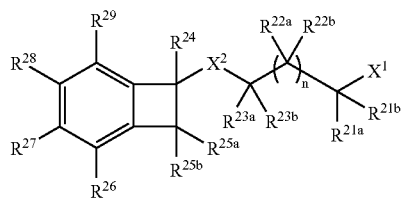

wherein $X^1$ is hydroxyl, primary amino, secondary amino, tertiary amino, thiol, or carboxyl; wherein n is zero or a positive integer; wherein $R^{21a}$, $R^{21b}$, $R^{22a}$, and $R^{22b}$, $R^{23a}$, and $R^{23b}$ are, independently, hydrogen, alkyl, alkoxyl, acyl, or carbonyl; wherein $X^2$ is oxygen, secondary nitrogen, tertiary nitrogen, or sulfur; wherein $R^{24}$, $R^{25a}$, $R^{25b}$, $R^{26}$, $R^{27}$, $R^{28}$, and $R^{29}$ are, independently, hydrogen, alkyl, alkenyl, alkynyl, alkoxyl, acyl, or carbonyl; and wherein the cyclobutane ring undergoes ring opening to form a reactive intermediate at a reaction temperature.

In a further aspect, the invention relates to a polymer or an oligomer comprising at least one residue of at least one disclosed compound.

c. Low Temperature Crosslinker

In one aspect, the invention relates to a low temperature crosslinker. That is, the invention relates to a reactive moiety capable of undergoing reaction to form a reactive intermediate and, thus, undergo intramolecular chain collapse at a relatively low temperature and/or in response to a stimulus. In one aspect, the low temperature crosslinkers comprise reactive moieties suitable for incorporation in polymers and/or copolymers as pendant groups.

Exemplary low temperature crosslinkers can be prepared, for example, with the following reaction sequence.

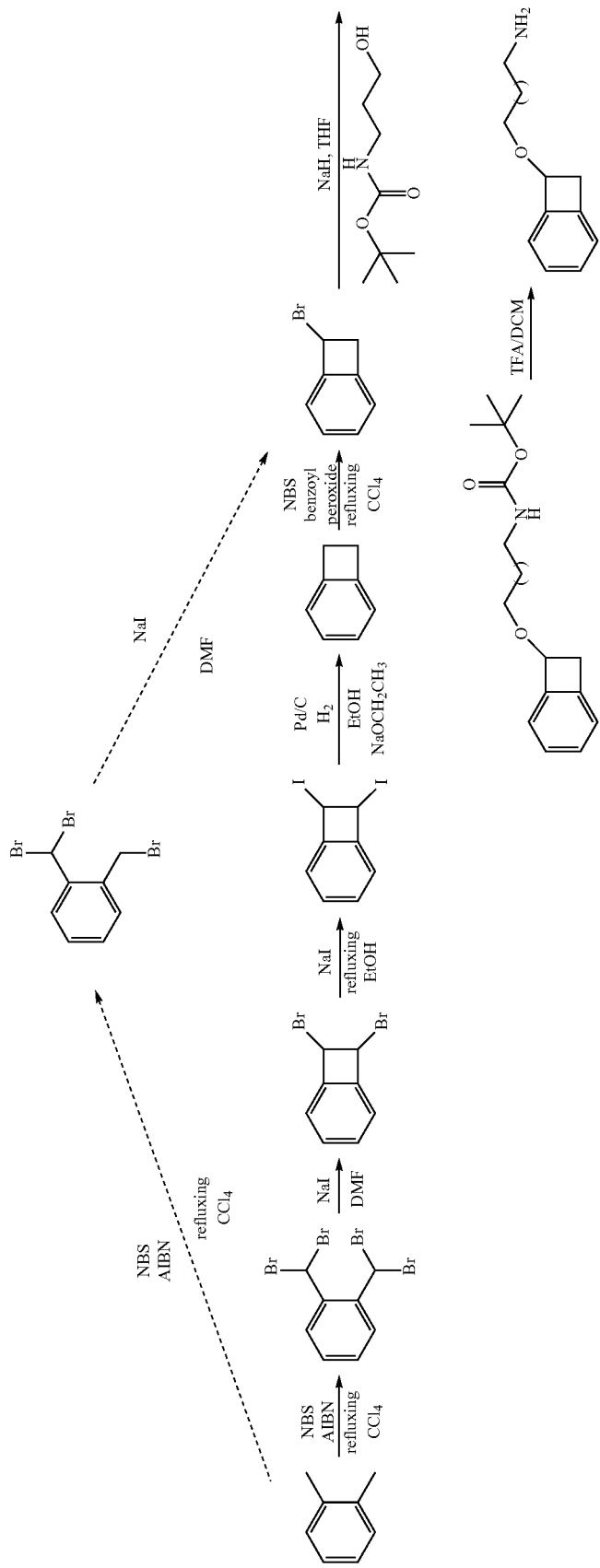

In a further aspect, exemplary low temperature crosslinkers can be prepared, for example, with one or more of the following reaction sequences:
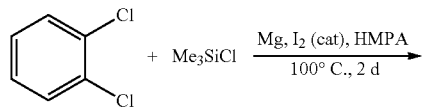
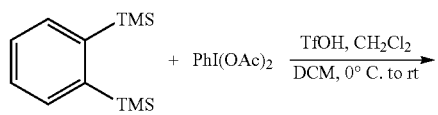
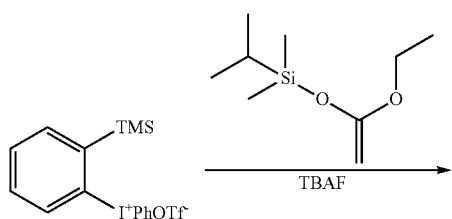
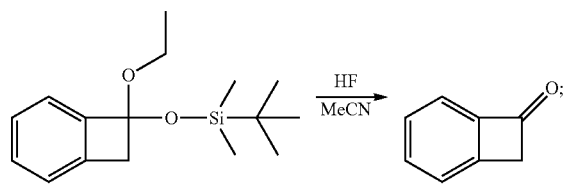
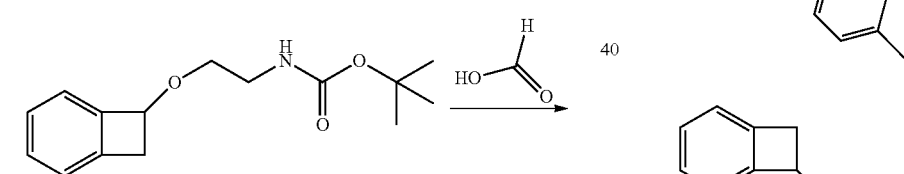
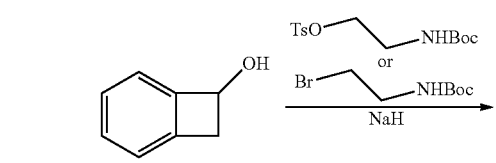
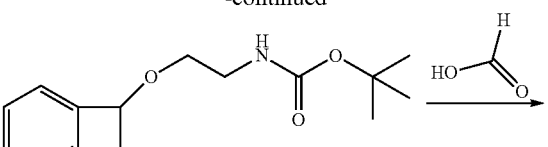
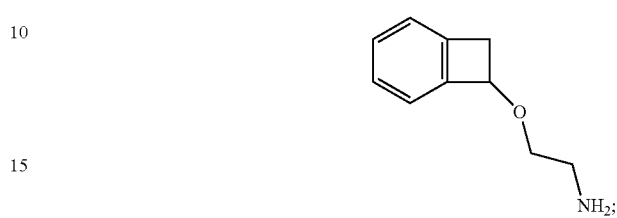
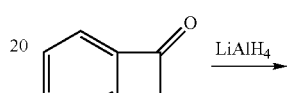
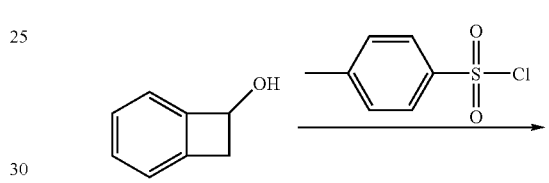
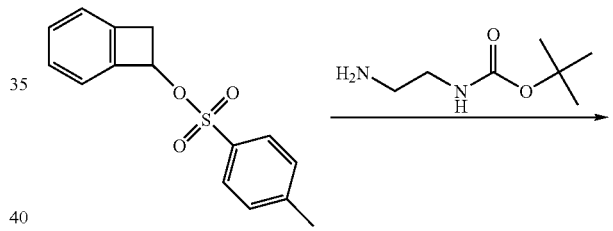
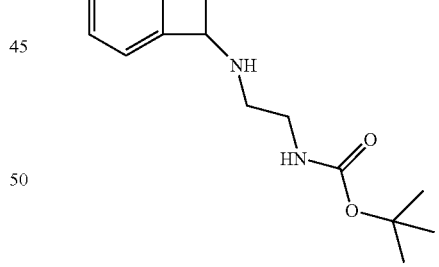
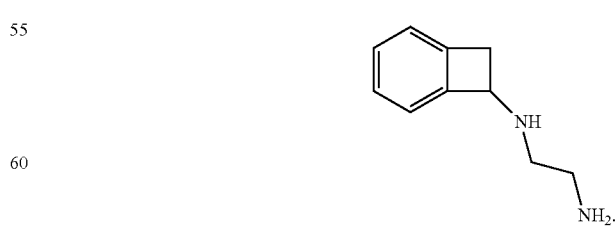
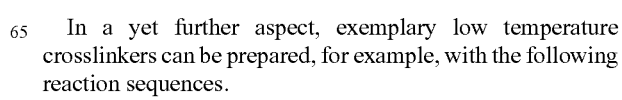
In a yet further aspect, exemplary low temperature crosslinkers can be prepared, for example, with the following reaction sequences.

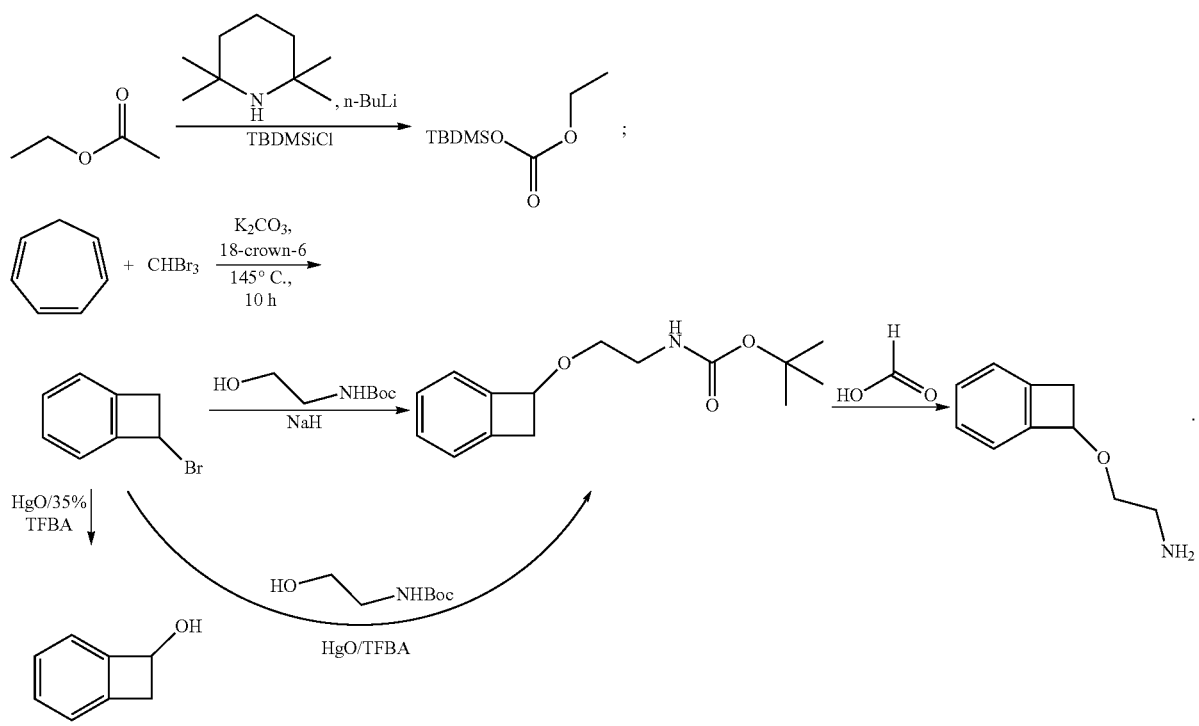

Thus, in one aspect, the invention relates to a method for preparing a nucleophile-functionalized benzocyclobutane comprising the steps of: providing a benzocyclobutane having a structure represented by a formula:

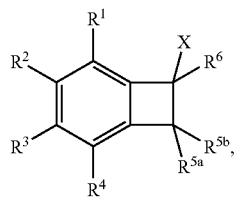

wherein $R^1$, $R^2$, $R^3$, $R^4$, $R^5$, $R^5b$ and $R^6$ are, independently, hydrogen, alkyl, alkene, alkyne, alkoxyl, hydroxyl, or carboxyl and wherein X is a leaving group; reacting the benzocyclobutene with a nucleophile having a structure represented by a formula:

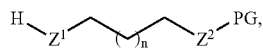

wherein $Z^1$ and $Z^2$ are, independently, hydroxyl, amino, or thiol, wherein n is an integer from 0 to 10, and wherein PG is a hydrogen or a protecting group; and optionally, removing the protecting group, if present, thereby preparing a nucleophile-functionalized benzocyclobutane having a structure represented by a formula:

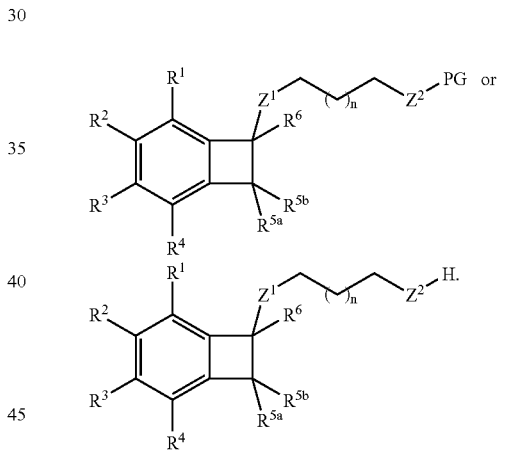

In a further aspect, $R^6$ is hydrogen. In a yet further aspect, $R^1$, $R^2$, $R^3$, and $R^4$ are hydrogen.

In various aspects, n can be zero or a positive integer. For example, n can be from 0 to 10, from 0 to 4, or from 2 to 4. It is understood that, in one aspect, n is the average for a distribution of alkyl moieties and, thus, can be a non-integer.

In a further aspect, the method further comprises the step of incorporating the nucleophile-functionalized benzocyclobutane into a polymer or oligomer. In a still further aspect, the incorporating step is grafting the nucleophile-functionalized benzocyclobutene onto a polymer or oligomer after polymerization.

In one aspect, the leaving group, X, is a halogen. In a further aspect, X is a sulfonyl-based leaving group, for example, tosylate, brosylate, or mesylate.

In one aspect, both $Z^1$ and $Z^2$ are oxygen. In a further aspect, both $Z^1$ and $Z^2$ are amino. In a yet further aspect, one of $Z^1$ and $Z^2$ is oxygen and one of $Z^1$ and $Z^2$ is amino, for example, $Z^1$=O and $Z^2$=NH. In a yet further aspect, $Z^2$ is amino and PG is a protecting group selected from benzyl, tert-butyloxycarbonyl, benzyloxycarbonyl, allyloxycarbonyl, and 2,2,2-trichloroethyloxycarbonyl. In a still further aspect, $Z^2$ is oxygen and PG is a protecting group selected from trimethylsilyl, tert-butyldimethylsilyl, triisopropylsilyl, acetyl, tetrahydropyran, methoxymethyl ether, β-methoxyethoxymethyl ether, p-methoxybenzyl ether, methylthiomethyl ether, and pivaloyl.

Note that the bromobenzocyclobutane intermediate can be conveniently prepared in two steps from o-xylene. The intermediate can then be readied for incorporation by conversion to a primary amine derivative. Alternatively, the intermediate can be readied for incorporation by conversion to a primary alcohol derivative.

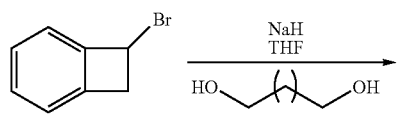

In one aspect, to avoid high temperatures during the intramolecular crosslinking process, a crosslinking unit which can form an o-chinodimethane derivative at around 100-120° C. was developed. In contrast to other crosslinking units, this unit can be conjugated to a linear polymer after polymerization. This allows the polymerization at 124° C., which is necessary for polymerization through NMP, without activating the low temperature crosslinker. Alternatively, by conjugating the unit to acrylmonomers (e.g., via esterification, amidation, or etherification) and copolymerizing, a vinyl monomer can be prepared, suitable for use in with living free radical methods allowing, for example, polymerization temperatures of 80° C. or less.

Exemplary low-temperature crosslinking units for attachment onto polymers as pendant groups are illustrated below:

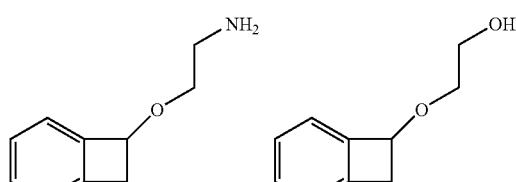

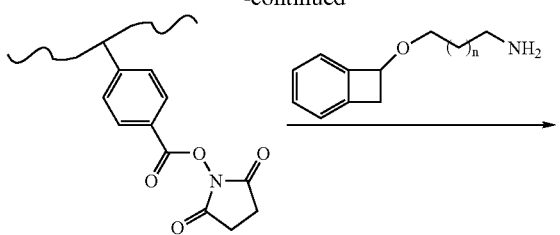

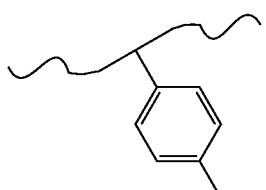

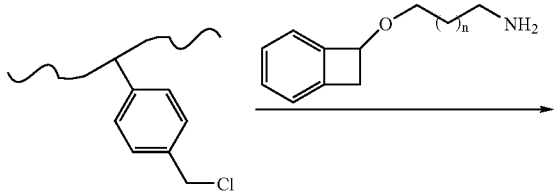

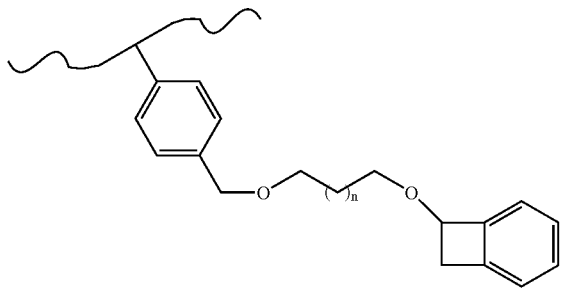

Exemplary low temperature crosslinking units synthesized as monomers for copolymerization are illustrated below:

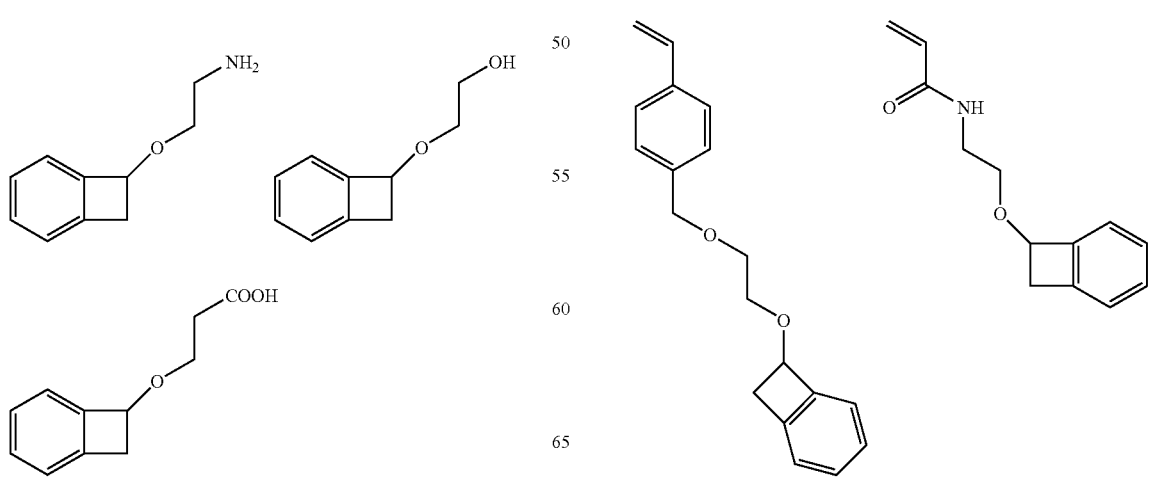

-continued

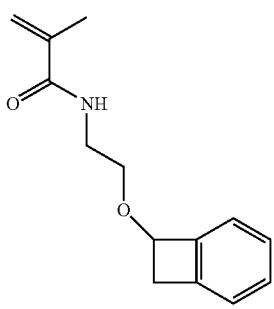

d. Intramolecular Chain Collapse

The disclosed crosslinking units can be imparted with a stimulus (e.g., increased temperature) to effect intramolecular chain collapse as shown below:

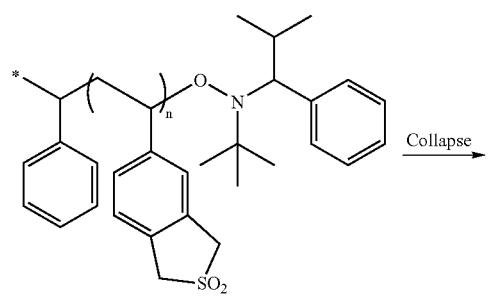

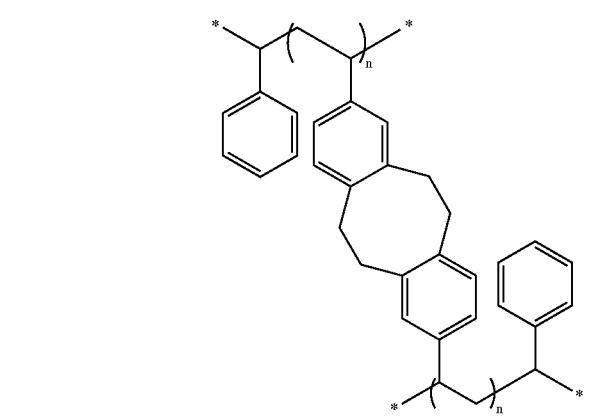

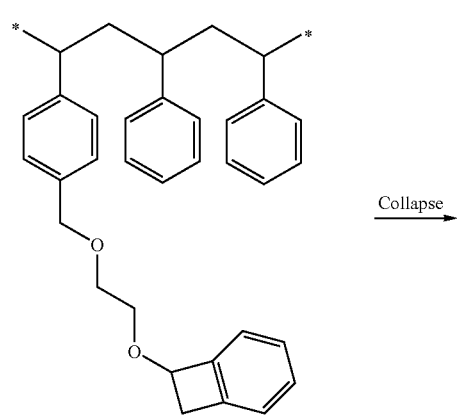

-continued

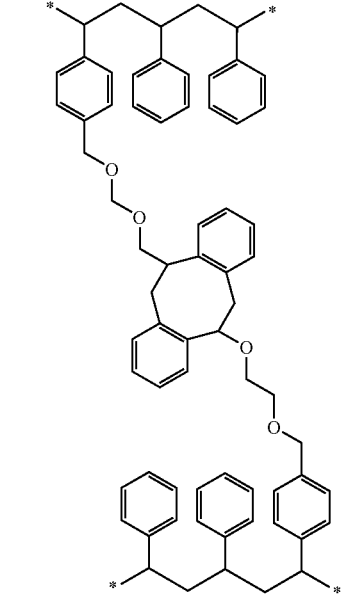

5. Block Copolymers

In one aspect, the invention relates to a block copolymer comprising the structure A-B, wherein A is an oligomeric block comprising at least two reactive residues, and wherein B is a block comprising at least one functional moiety. In one aspect, B comprises substantially no reactive residues. That is, reactive residues are essentially absent from B. In a further aspect, B further comprises at least one reactive residue.

In one aspect, the disclosed block copolymers relate to the disclosed compounds.

a. Functional Moeities

In a further aspect, the functional moiety comprises a semi-conducting moiety, an imaging moiety, or a drug-delivery moiety. In a yet further aspect, the functional moiety comprises a semiconducting moiety. In one aspect, the semiconducting moiety comprises one or more residues selected from:

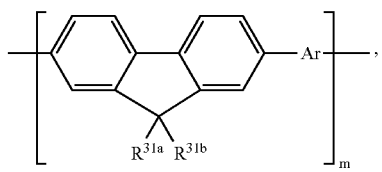

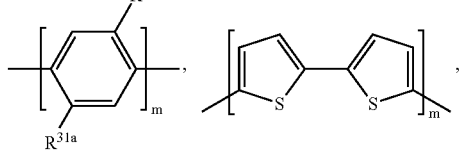

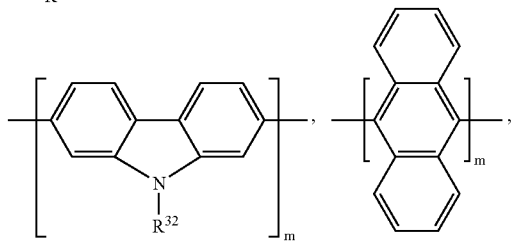

-continued

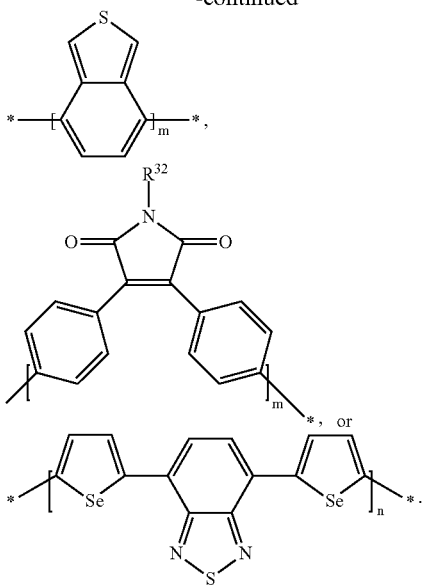

wherein $R^{31a}$ and $R^{31b}$ are, independently, hydrogen or alkyl; wherein $R^{32}$ is hydrogen, alkyl, or polyalkylene glycol; and wherein m is zero or a positive integer.

In a further aspect, $R^{31a}$ and $R^{31b}$ are independently selected from

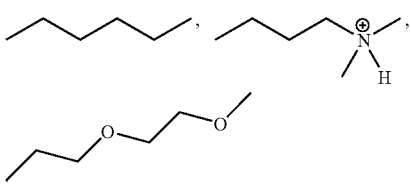

In one aspect, m is an integer from 1 to 20.

In one aspect, the functional moiety comprises an imaging moiety. In a further aspect, the imaging moiety comprises are least one catechol unit for the complexation of radioactive metals such as $^{64}Cu$, $^{111}In$, lanthanides, rare earth metals, iron oxide, or complexing units such as DOTA, DPTA, chromophores, nonlinear optical (NLO) materials, fluorophores, and/or other electroactive materials.

In one aspect, the functional moiety comprises a drug-delivery moiety. In a further aspect, the drug-delivery moiety bears at least one of a biologically active agent and/or a pharmaceutically active agent. In a yet further aspect, the drug-delivery moiety comprises cis-platinum, cancer drugs such as taxol, doxorubicin, abraxene, anastrozol paclitaxel, exemestane, cyclophoshamide, epirubicin, tormifene, letrozole, trastuzumab, megestrol, nolvadex, docetaxel, capecitabine, goserelin acetate, zoledronic acid, raloxifene, faslodex. methotrexate, multiple sclerosis agents, hormones, antioxidants, antimicrobials, antibacterial agents, antidepressants, sedatives, antihypertensive drugs, antibodies, a carbohydrate-based drug, Fab fragments of the anti-melanoma antibody NRML-05, pan-carcinoma antibody NRLU-10, anti-CEA immunotoxin, liposome drugs, fusogenic, dendritic cell vaccines, viralcapsids, and/or bacteria. These drugs can be directly connected to the backbone of a copolymer or conjugated with a linker. In a further aspect, the drug-delivery moiety can be a hypothermally-resposive metal, for example, gold. In a still further aspect, the drug-delivery moiety comprises at least one of a peptide and a glycoside, such as α-mannose or other sugar molecules). It is also contemplated that further drug functionalities can be incorporated if capable of bonding to the disclosed compounds.

In one aspect, m is from about 5 to about 15. In a further aspect, A is from about 5 to about 15 residues in length. In a still further aspect, B is from about 5 to about 15 residues in length. In a yet further aspect, B is an oligomeric block.

In a further aspect, A further comprises at least one residue selected from styrene, acrylate, acrylamide, and methyl methacrylate and/or derivatives thereof, including:

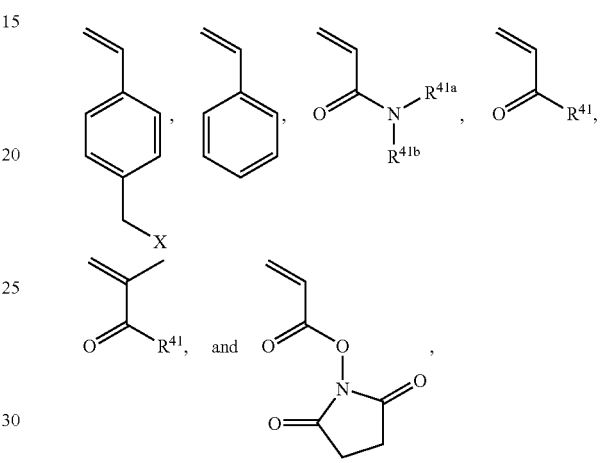

wherein X is halogen; wherein $R^{41}$, $R^{41a}$, and $R^{41b}$ are, independently, hydrogen, alkyl, or alkoxyl. It is contemplated that, in certain aspects, other non-halogen leaving groups (e.g., tosylate) can be substituted for halogen. In a still further aspect, $R^{41}$, $R^{41a}$, and $R^{41b}$ are independently selected from:

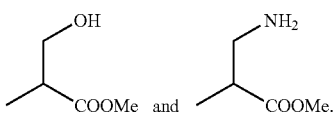

b. Reactive Residues

In one aspect, the at least two reactive residues comprise the structure:

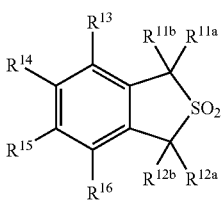

wherein $R^{11a}$, $R^{11b}$, $R^{12a}$, and $R^{12b}$ are, independently, hydrogen, alkyl, alkoxyl, acyl, or carbonyl; wherein $R^{13}$, $R^{14}$, $R^{15}$, and $R^{16}$ are, independently, hydrogen, alkyl, alkenyl, alkynyl, alkoxyl, acyl, or carbonyl, with the proviso that at least one of $R^{13}$, $R^{14}$, $R^{15}$, or $R^{16}$ is a polymerizable group; and wherein the compound eliminates $SO_2$ to form a reactive intermediate at a reaction temperature.

In a further aspect, the at least two reactive residues comprise the structure:

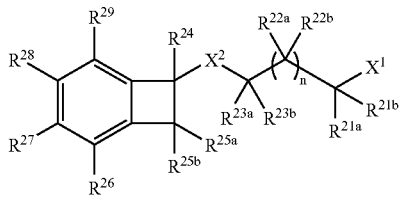

wherein $X^1$ is hydroxyl, primary amino, secondary amino, tertiary amino, thiol, or carboxyl; wherein n is zero or a positive integer; wherein $R^{21a}$, $R^{21b}$, $R^{22a}$, and $R^{22b}$, $R^{23a}$, and $R^{23b}$ are, independently, hydrogen, alkyl, alkoxyl, acyl, or carbonyl; wherein $X^2$ is oxygen, secondary nitrogen, tertiary nitrogen, or sulfur; wherein $R^{24}$, $R^{25a}$, $R^{25b}$, $R^{26}$, $R^{27}$, $R^{28}$, and $R^{29}$ are, independently, hydrogen, alkyl, alkenyl, alkynyl, alkoxyl, acyl, or carbonyl; and wherein the cyclobutane ring undergoes ring opening to form a reactive intermediate at a reaction temperature.

In a further aspect, the at least two reactive residues are capable of forming a reactive intermediate comprising an o-quinoid moiety at a reaction temperature of less than about 175° C. In a yet further aspect, the reaction temperature is less than about 150° C. In a yet further aspect, the reaction temperature is less than about 125° C. In a yet further aspect, the reaction temperature is less than about 115° C. In a yet further aspect, the reaction temperature is less than about 110° C. In a still further aspect, the reaction temperature is from about 100° C. to about 150° C.

c. Structure

In one aspect, the block copolymer comprises the structure A-B-A. In a further aspect, the block copolymer comprises the structure A-B-C, wherein C is an oligomeric block comprising at least two reactive residues. In a yet further aspect, the at least two reactive residues of block A are different from the at least two reactive residues of block C. In a still further aspect, the block copolymer comprises the structure P-A-B, wherein P comprises a peptide moiety attached to block A. In various further aspects, the peptide moiety comprises cell penetrating peptides such as oligoarginines or Tat peptide, peptide ligands to irradiated tumor cells, G protein, $p16^{INK4a}$, Bak BH3 domain peptide, cGPK-Iα inhibitory peptide, IKKβ C-terminal peptide, PKA inhibitory peptide, MEK 1 N-terminal peptide, a peptide nucleic acid (PNA) cardioprotective EPKC agonist peptide, VHL tumor suppressor peptide, HER-2, Pro-apotoxic Smac peptide, oligonucleotides, a plasmid DNA, an immunoglobulin, and antisense oligoDNA. It is contemplated that proteins known for certain functions (e.g., peptides for targeting, immunoresponse, etc.) can be used in connection with the invention. In one aspect, the block copolymer comprises the structure P-A-B-A. In a further aspect, the block copolymer comprises the structure P-A-B-C, wherein C is an oligomeric block comprising at least two reactive residues.

In a still further aspect, the block copolymer comprises the structure E-A-B, wherein E comprises an enzyme moiety attached to block A. In various further aspects, the enzyme moiety comprises β-galactosidase, horseradish peroxidase, RNase, anti-apoptotic proteins Bcl-X(L)/PEA-15, catalase, green fluorescence protein, heat shock protein 70, human glutamate dehydrogenase, ovalbumin, neuroptotectant Bcl-xL, E2 protein, phosphorothioate antisense oligonucleotides, anti-tetanus F(ab')$_2$, caspase-3, $p14^{INK4a}$, $p27^{kip1}$, luciferin, RhoA, APO-BEC-1, Cre recombinase, H-Ras, Filmin-1, p16, HPC-1/syntaxin, Cdk2, E2f-1/p73/p53, influenza virus, bacteria, birdflu virus, and/or bacteria. In a further aspect, the block copolymer comprises the structure E-A-B-A. In a still further aspect, the block copolymer comprises the structure E-A-B-C, wherein C is an oligomeric block comprising at least two reactive residues.

6. Methods of Nanoparticle Formation

In one aspect, the invention relates to a method of nanoparticle formation comprising the steps of providing a reactor capable of imparting a stimulus and adding to the reactor a block copolymer comprising at least two reactive residues, thereby imparting the stimulus on at least a portion of the block copolymer; wherein the at least two reactive residues form reactive intermediates upon exposure to the stimulus, and wherein the reactive intermediates are capable of undergoing a bond-forming reaction.

In one aspect, the disclosed methods relate to the disclosed block copolymers.

In a further aspect, the adding step is performed at a first rate, wherein the reactive intermediates are formed at a second rate, wherein the reactive intermediates undergo the bond-forming reaction at a third rate, and wherein the third rate is greater than the first rate. In a yet further aspect, the third rate is greater than the second rate. In one aspect, the linear precursor concentration during the first rate is $10^{-7}$ molar and is added to the solution with 12.6 ml/h.

In one aspect, the stimulus is at least one of a thermal stimulus, a chemical stimulus, or an electromagnetic stimulus or a mixture thereof. In a further aspect, the stimulus is a thermal stimulus comprising increased heat, decreased heat, increased agitation, decreased agitation, increased kinetic energy, or decreased kinetic energy or a mixture thereof. In a yet further aspect, the stimulus is a chemical stimulus comprising an increase in pH, a decrease in pH, an addition of radical initiator, an initiation of radical scavenger, an increase in polarity, or a decrease in polarity or a mixture thereof. In a still further aspect, the stimulus is an electromagnetic stimulus comprising visible light, ultraviolet light, infrared light, microwaves, radio waves, or magnetic waves or a mixture thereof.

In one aspect, the at least two reactive residues comprise the structure:

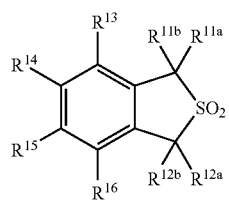

wherein $R^{11a}$, $R^{11b}$, $R^{12a}$, and $R^{12b}$ are, independently, hydrogen, alkyl, alkoxyl, acyl, or carbonyl; wherein $R^{13}$, $R^{14}$, $R^{15}$, and $R^{16}$ are, independently, hydrogen, alkyl, alkenyl, alkynyl, alkoxyl, acyl, or carbonyl, with the proviso that at least one of $R^{13}$, $R^{14}$, $R^{15}$, or $R^{16}$ is a polymerizable group; and wherein the compound eliminates $SO_2$ to form a reactive intermediate at a reaction temperature.

In a further aspect, the at least two reactive residues comprise the structure:

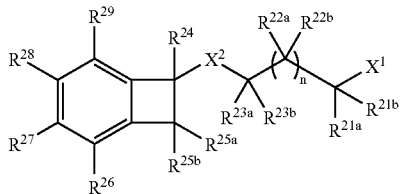

wherein $X^1$ is hydroxyl, primary amino, secondary amino, tertiary amino, thiol, or carboxyl; wherein n is zero or a positive integer; wherein $R^{21a}$, $R^{21b}$, $R^{22a}$, and $R^{22b}$, $R^{23a}$, and $R^{23b}$ are, independently, hydrogen, alkyl, alkoxyl, acyl, or carbonyl; wherein $X^2$ is oxygen, secondary nitrogen, tertiary nitrogen, or sulfur; wherein $R^{24}$, $R^{25a}$, $R^{25b}$, $R^{26}$, $R^{27}$, $R^{28}$, and $R^{29}$ are, independently, hydrogen, alkyl, alkenyl, alkynyl, alkoxyl, acyl, or carbonyl; and wherein the cyclobutane ring undergoes ring opening to form a reactive intermediate at a reaction temperature.

In one aspect, the at least two reactive residues are capable of forming a reactive intermediate comprising an o-quinoid moiety at a reaction temperature of less than about 175° C. In a further aspect, the reaction temperature is less than about 150° C. In a further aspect, the reaction temperature is less than about 125° C. In a further aspect, the reaction temperature is less than about 115° C. In a further aspect, the reaction temperature is less than about 110° C. In a further aspect, the reaction temperature is from about 100° C. to about 150° C.

G. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

General.

Commercial reagents were obtained from commercial sources (Aldrich, EMD, Alfa-Aesar, Fisher Scientific, and Acros) and used without further purification. Analytical TLC was performed on commercial Merck plates coated with silica gel GF254 (0.24 mm thick) and spots located by UV light (254 and 366 nm). Silica gel for flash chromatography was Merck Kieselgel 60 (230-400 mesh, ASTM) or Sorbent Technologies 60 Å (40-63 µm, technical grade). MAL-dPeg™₄-t-boc-hydrazide was obtained from Quanta Biodesign, Ltd. (Powell, Ohio) and used as received. Cy3 NHS dye and PD-10 Desalting columns were received from GE Healthcare (Piscataway, N.J.). Spectra/Por® Biotech Cellulose Ester (CE) Dialysis Membranes (1,000 MWCO) obtained from Spectrum Laboratories, Inc. (Rancho Dominguez, Calif.). SnakeSkin® Pleated Dialysis Tubing (10,000 MWCO) was obtained from Pierce Biotechnology, Inc. (Rockford, Ill.).

Instrumentation:

Samples were centrifuged at 600 rpm on a Model CS International Centrifuge from International Equipment Company (Boston, Mass.). Reverse-phase high performance liquid chromatography (RP-HPLC) was carried out with a Varian Prostar HPLC. The products were eluted using a solvent gradient (solvent A=0.05% TFA/$H_2O$; solvent B=0.05% TFA/$CH_3CN$). Nuclear magnetic resonance was performed on Bruker AC300 and AC400 Fourier Transform Spectrometers using deuterated solvents and the solvent peak as a reference. Gel permeation chromatography was performed in tetrahydrofuran (THF) with the eluent at a flow rate of 1 mL/min on a Waters chromatograph equipped with four 5 mm Waters columns (300 mm×7.7 mm) connected in series with increasing pore size (100, 1000, 100,000 and 1,000,000 Å respectively). A Waters 2487 Dual λ Absorbance Detector and a 2414 Refractive Index Detector were employed. Dynamic light scattering was performed on a Malvern Zetasizer Nanoseries instrument with a CGS-3 compact goniometer system.

1. Synthesis of Compound 1

To a solution of dimethoxyethane (40 mL) was added $MeNO_2$ (11.37 mL, 200 mmol) followed by Triton B (2 mL). The mixture was heated to 67° C. and then tert-butyl acrylate (91.83 mL, 620 mmol) was added to maintain the temperature at 75° C. When the temperature started to decrease, additional Triton B (1 mL) was added. After the addition was completed, the solution was heated to maintain at 75° C. for 2 hours. The solvent was removed in vacuo and the residue was dissolved in $CHCl_3$ and the resulting organic solution was washed with 10% HCl, brine, and dried over anhydrous $Na_2SO_4$. Removal of the solvent in vacuo gave a crude solid that was further purified by recrystallization from EtOH to obtain a colorless crystal (95% yield). $^1H$ NMR ($CDCl_3$): δ1.44 (s, $CH_3$, 27H), 2.21 (m, $CH_2$, 12H). $^{13}C$ NMR ($CDCl_3$): 27.93 ($CH_3$), 29.68 ($CH_2CO$), 30.22 ($CCH_2$), 81.02 ($CCH_3$), 92.09 ($CNH_2$), 170.97 ($CO_2$).

2. Synthesis of Compound 2

A solution of compound 1 (6.0 g, 0.0135 mol) in a mixture of ethanol (140 mL) and dichloromethane (20 mL) was added to a Parr hydrogenation bottle. Then, 4 grams of Raney-nickel was added. The mixture was hydrogenated at 50 psi and room temperature. The reaction was monitored by thin-layer chromatography (TLC) until the starting material disappeared. The catalyst was carefully filtered through Celite, and the solvent was removed in vacuo yielding a crude solid. The residue was dissolved in dichloromethane and washed with saturated $NaHCO_3$ and water, and then dried over anhydrous $Na_2SO_4$. Removal of dichloromethane gave a white solid (93%). $^1H$ NMR ($CDCl_3$): δ1.44 (s, $CH_3$, 27H), 1.95 (t, $CH_2$, 6H), 2.43 (t, $CH_2$, 6H); $^{13}C$ NMR ($CDCl_3$): 27.98 ($CH_3$), 29.46 ($CH_2CO$), 31.47 ($CCH_2$), 56.99 ($CNH_2$), 80.96 ($CCH_3$), 172.30 ($CO_2$).

3. Synthesis of Compound 4

To a solution of compound 3 (0.65 g, 2.35 mmol) in 50 mL dry THF the following reagents were added 1-hydrobenzotriazole (HOBt) (0.96 g, 7.10 mmol), DCC (1.46 g, 7.10 mmol) and then 2 (3.54 g, 8.5 mmol). The solution was stirred at room temperature and the reaction was monitored by TLC. After 40 hrs, the white precipitate was filtered and the solution was concentrated to yield a crude residue. The product was purified by column chromatography (silica gel, hexane: ethyl acetate=3:2) yielding a white solid (85%). $^1$H NMR (CDCl$_3$): δ1.44 (m, CH$_3$, 81H), 1.95 (m, CH$_2$, 18 H), 2.21 (m, CH$_2$, 30H), 6.20 (s, NH, 3H); $^{13}$C NMR (CDCl$_3$): 28.04, 29.74, 29.85, 31.28, 57.56, 80.69, 92.47, 170.46, 172.76.

4. Synthesis of Compound 5

A solution of compound 4 (1.47 g, 1 mmol) in 15 mL of formic acid was stirred at room temperature overnight. After the solution was concentrated, toluene was added and the solution was evaporated to remove any residue of formic acid to give a white solid (100%). $^1$H NMR (DMSO): δ1.81 (m, CH$_2$, 18 H), 2.11 (m, CH$_2$, 30H), 7.29 (s, NH, 3H), 12.10 (br, COOH); $^{13}$C NMR (DMSO): 28.03, 29.03, 30.08, 56.41, 93.31, 170.43, 174.42.

5. Synthesis of Compound 6

To a solution of compound 5 (2.12 g, 0.0022 mol) in DMF (30 mL), HOBt (2.68 g, 0.0198 mol) and DCC (4.09 g, 0.0198 mol) were added. The mixture was chilled to 0° C. with ice-water bath. Then, a solution of N-Boc-ethylenediamine (3.49 g, 0.0218 mol) in DMF (5 mL) was added dropwise at 0° C. The reaction mixture was stirred at room temperature for 48 hrs. The solution was then filtered and 200 mL of dichloromethane was added, and washed with 1N HCl, saturated NaHCO$_3$, and water. The organic phase was dried over anhydrous Na$_2$SO4 and evaporated to yield a crude residue. The product was purified by column chromatography (eluted first with 2% methanol in dichloromethane, then with 6% methanol in dichloromethane, followed by 10% methanol in dichloromethane) to obtain a white solid (51%). $^1$HNMR (CD$_3$OD): δ 1.44 (m, CH$_3$, 81H), 1.80-2.10 (m, CH$_2$, 48H), 3.0-3.2 (m, CH$_2$, 36H), 6.20 (m, NH, 3H), 6.46 (m, NH, 8H), 7.71 (m, NH, 8H); $^{13}$C NMR (CD$_3$OD): 28.40, 31.24, 31.44, 31.80, 32.09, 40.66, 40.97, 59.14, 80.13, 94.42, 158.48, 173.48, 175.91. This white solid was then dissolved in 40 mL of 1,4-dioxane. At 0° C., 40 mL of 4 M HCl in dioxane was added to the solution under Ar atmosphere and stirred at room temperature for 1 hr. Removal of the solvent gave a white solid as the deprotected HCl salt (100%). $^1$HNMR (D$_2$O): δ 1.70-2.15 (m, CH$_2$, 48H), 3.30 (m, CH$_2$, 18H), 3.36 (m, CH$_2$, 18H); $^{13}$C NMR (D$_2$O): 27.61, 27.98, 28.86, 35.11, 37.41, 56.29, 92.01, 171.84, 174.98. 1.53 g (0.92 mmol) of the resulting HCl salt was dissolved in 80 mL of methanol. At 0° C., 3.5 mL of Et$_3$N was added to the solution, followed by the addition of N,N'-diBoc-N"-triflylguanidine (4.2 g, 10.73 mmol). The solution was stirred at room temperature for 24 hr. After removal of the solvent, the residue was dissolved in dichloromethane and washed with water, 1N HCl, saturated NaHCO$_3$, and water. The organic layer was dried over anhydrous Na$_2$SO$_4$ and removed in vacuo. The residue product was purified by column chromatography (eluted with 2% methanol in dichloromethane, then 10% methanol in dichloromethane) to give a white solid (90%) as compound 6. $^1$H NMR (CD$_3$OD): δ 1.45 (m, CH$_3$, 81H), 1.51 (m, CH$_3$, 81H), 1.90-2.25 (m, CH$_2$, 48 H), 3.30-3.52 (m, CH$_2$, 36H); $^{13}$C NMR (CD$_3$OD): 28.37, 28.67, 31.32, 31.67, 32.06, 39.74, 41.24, 59.02, 80.23, 84.35, 94.31, 153.91, 157.737, 164.38, 173.33, 175.87.

6. Synthesis of Compound 7

To a solution of compound 5 (1.2, 0.001245 mol), HOBt (1.514 g, 0.0112 mol) and DCC (2.311 g, 0.0112 mol) were added in 20 mL of DMF. Then, N-Boc-1,6-diaminohexane (2.66 g, 0.0123 mol) was dissolved in 5 mL of DMF dropwise at 0° C. The solution was then stirred at room temperature for 48 hrs. The solution was then filtered and 200 mL of dichloromethane was added, and washed with 1N HCl, saturated NaHCO$_3$, and water. The organic phase was dried over anhydrous Na$_2$SO$_4$ and evaporated to yield a crude residue. The product was purified by column chromatography (eluted first with 2% methanol in dichloromethane, then with 5% methanol in dichloromethane, followed by 10% methanol in dichloromethane) to obtain a white solid (45%). $^1$H NMR (CD$_3$OD): δ 1.2-1.6 (m, CH$_3$, CH$_2$, 153H), 1.80-2.10 (m, CH$_2$, 48 H), 3.0-3.2 (m, CH$_2$, 36H); $^{13}$C NMR (CD$_3$OD): 27.54, 28.85, 30.37, 30.90, 31.28, 31.60, 32.14, 40.58, 41.24, 59.13, 79.30, 94.30, 158.49, 173.50, 175.56. This white solid was then dissolved in 40 mL of 1,4-dioxane. At 0° C., 40 mL of 4 M HCl in dioxane was added to the solution under Ar atmosphere and stirred at room temperature for 1 hr. Removal of the solvent gave a white solid as the deprotected HCl salt (100%). $^1$HNMR (D$_2$O): δ 1.10-1.60 (m, CH$_2$, 72), 1.7-2.2 (m, CH$_2$, 48H), 3.30 (m, CH$_2$, 18H), 3.36 (m, CH$_2$, 18H). 0.838 g (0.385 mmol) of the resulting HCl salt was dissolved in 80 mL of methanol. At 0° C., 1.45 mL of Et$_3$N was added to the solution, followed by the addition of N,N'-diBoc-N"-triflylguanidine (1.765 g, 4.51 mmol). The solution was stirred at room temperature for 24 hr. After removal of the solvent, the residue was dissolved in dichloromethane and washed with water, 1N HCl, and water. The organic layer was dried over anhydrous Na$_2$SO$_4$ and removed in vacuo. The residue product was purified by column chromatography (eluted with 2% methanol in dichloromethane, then 10% methanol in dichloromethane) to give a white solid (90%) as compound 7. $^1$H NMR (CD$_3$OD): $^1$H NMR of 9 (CD$_3$OD): δ 1.15-1.55 (m, 234H), 1.70-2.15 (m, CH$_2$, 48 H), 3.29-3.30 (m, CH$_2$, 36H); $^{13}$C NMR (CD$_3$OD): 27.70, 27.62, 28.33, 28.67, 30.08, 30.33, 31.30, 31.60, 40.48, 40.62, 41.27, 54.5, 59.14, 80.25, 84.40, 154.22, 157.49, 164.53, 173.50, 175.53.

7. Synthesis of Compound 8 and 9

Compound 6 (or 7, 0.10 mmol) was dissolved in 40 mL of ethanol and transferred into a hydrogenation bottle containing 5 g of Raney-Nickel catalyst. The solution was hydrogenated at room temperature at 65 psi and monitored by TLC. The catalyst was filtered through Celite. The solvent was removed in vacuo to give a white solid 8 or 9 (80%). $^1$H NMR of 8 (CD$_3$OD): δ 1.46 (m, CH$_3$, 81H), 1.51 (m, CH$_3$, 81H), 1.90-2.25 (m, CH$_2$, 48 H), 3.30-3.55 (m, CH$_2$, 36H); $^{13}$C NMR (CD$_3$OD): 28.37, 28.67, 31.40, 31.76, 39.76, 41.27, 54.0, 58.86, 80.32, 84.37, 153.97, 157.81, 164.4, 175.61, 176.02. $^1$HNMR of 9 (CD$_3$OD): δ 1.20-1.70 (m, 234H), 1.85-2.40 (m, CH$_2$, 48 H), 3.10-3.50 (m, CH$_2$, 36H); $^{13}$C NMR (CD$_3$OD): 27.01, 27.18, 28.27, 28.53, 29.42, 29.71, 30.15, 30.88, 31.19, 40.03, 41.23, 54.3, 58.21, 79.93, 83.84, 153.62, 156.65, 163.83, 175.77.

8. Synthesis of Compound FD-1

FITC (0.14 g, 0.36 mmol), dissolved in 1 mL of DMF, was added to a solution of compound 8 (0.23 g, 0.066 mmol) in a mixture of DMF and dichloromethane. The solution was chilled to 0° C., to which Et$_3$N (0.092 mL, 0.66 mmol) was added. The mixture was stirred overnight at room temperature. After removal of DMF in vacuo, the residue was dissolved in dichloromethane and washed with 1N HCl and water. The dichloromethane layer was dried over anhydrous Na$_2$SO$_4$ and concentrated to obtain a yellow solid. $^1$H NMR (CD$_3$OD): δ 1.46 (m, CH$_3$, 81H), 1.51 (m, CH$_3$, 81H), 1.90-

2.25 (m, CH$_2$, 48 H), 3.30-3.55 (m, CH$_2$, 36H), 6.52-6.72 (br, 4H), 7.15 (br, 1H), 7.5 (br, 2H), 7.72 (br, 1H), 8.4 (br, 1H). The resulting yellow solid (200 mg, 0.052 mmol) was dissolved in 10 mL of 1,4-dioxane. At 0° C., 10 mL of 4 M HCl in dioxane was added to the solution under Ar protection and stirred at room temperature overnight. After evaporation of the solvent in vacuo, the product was dissolved in water and the insoluble precipitate was filtered. Removal of water yielded a crude yellow solid, which was further purifed by RP-HPLC using a solvent gradient (solvent A=0.05% TFA/H$_2$O; solvent B=0.05% TFA/CH$_3$CN) to obtain compound 10. $^1$H NMR (D$_2$O): δ 1.85-2.30 (m, CH$_2$, 48 H), 3.10-3.30 (m, CH$_2$, 36H), 6.9 (br, 2H), 7.10-7.2 (m, 3H), 7.4 (s, 2H), 7.5 (br, 1H), 8.1 (s, 1H).

9. Synthesis of Compound Fd-2

FITC (0.016 g, 0.0376 mmol), dissolved in 1 mL of DMF, was added to a solution of compound 9 (0.050 g, 0.0125 mmol) in a mixture of DMF and dichloromethane (1:1). The solution was chilled to 0° C., to which Et$_3$N (12 µL) was added. The mixture was stirred overnight at room temperature. After removal of DMF in vacuo, the residue was dissolved in dichloromethane and washed with 1N HCl and water. The dichloromethane layer was dried over anhydrous Na$_2$SO$_4$ and concentrated to obtain a solid. The product was dissolved in methanol and purified by dialysis with Spectro®Por Biotech RC membranes (MWCO 3500). After removal of the methanol, a yellow solid was obtained. $^1$H NMR (CD$_3$OD): δ 1.20-1.7 (m, CH$_3$, CH$_2$, 234H), 1.89-2.30 (m, CH$_2$, 48 H), 3.10-3.40 (m, CH$_2$, 36H), 6.52-6.72 (br, 4H), 7.15 (br, 1H), 7.5-7.72 (br, 3H), 8.1 (br, 1H). The resulting yellow solid (200 mg, 0.052 mmol) was dissolved in 10 mL of 1,4-dioxane. At 0° C., 10 mL of 4 M HCl in dioxane was added to the solution under Ar protection and stirred at room temperature overnight. The precipitate was filtered out and dried in vacuo. The obtained yellow solid was dissolved in water and lyophilized to yield compound 11. $^1$H NMR (D$_2$O): δ 1.1-1.50, (m, CH$_2$, 72H), 1.50-2.20 (m, CH$_2$, 48 H), 3.10-3.30 (m, CH$_2$, 36H), 6.5-6.7 (br, 6H), 7.10 (m, 1H), 7.5 (br, 3H).

10. Examples FD-1 and FD-2

As examples of the compounds of the invention, two non-peptidic fluorescently labeled Newkome-type dendrimers, differentiated over a varied alkylspacer with guanidine end moieties, were designed and synthesized. The assessment of internalization into mammalian cells using NIH-3T3 fibroblasts and human microvascular endothelial cells (HMEC) showed that the spacer length at the terminal generation of the dendrimers can affect direction of cargo molecules precisely into specific subcellular compartments (e.g., nucleus or cytosol). Such direction can be particularly advantageous for the controlled intracellular delivery of bioactive cargo molecules into targeted locations.

Figure 2:
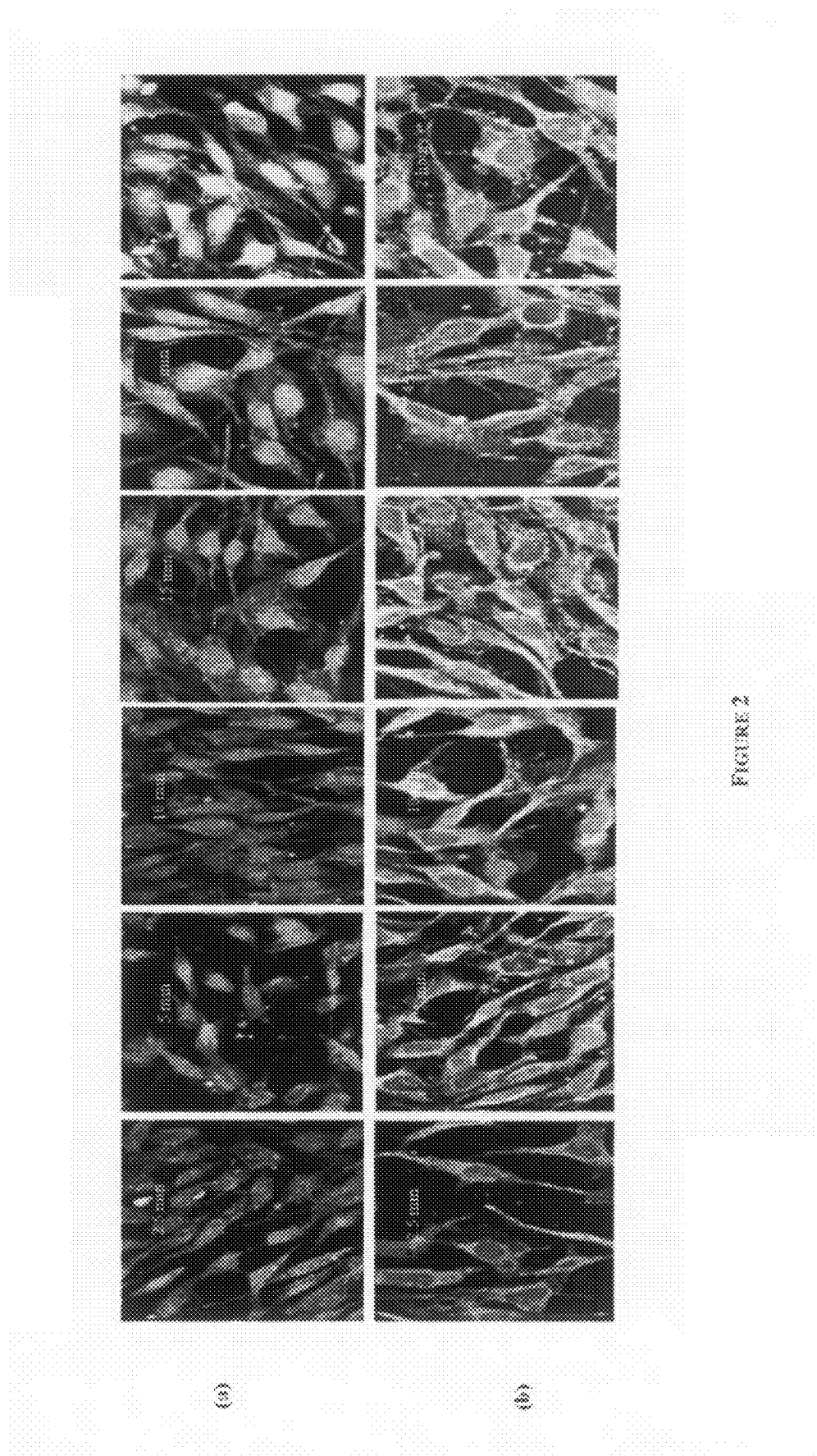
FIG. 2 shows time course of internalization of (a) FD-1 and (b) FD-2 into NIH-3T3 Fibroblasts at 37° C. The conjugate concentration was 10 μM.

The two exemplary FITC-dendrimer conjugates were found to be highly water soluble and were further investigated for their capability to translocate through the cell membrane. Internalization of FD-1 and FD-2 in mammalian cells was assessed using two different cell lines and a previously described method [Futaki, S.; Nakase, I.; Suzuki, T.; Youjun, Y.; Sugiura, Y. Biochemistry 2002, 41, 7925.] with NIH-3T3 fibroblasts and HMEC (human microvascular endothelial cells) and a Zeiss LSM 510 confocal microscope. FIG. 2 shows the time course of uptake of FD-1 and FD-2 into NIH-3T3 Fibroblasts at 37° C. The fluorescence was clearly observed within the cells 2.5 min after the addition of conjugates to the medium, which is comparable to the uptake rate of Tat-peptide. [Futaki, S.; Nakase, I.; Suzuki, T.; Youjun, Y.; Sugiura, Y. Biochemistry 2002, 41, 7925.; Vivès, E.; Brodin, P.; Lebleu, B. J. Biol. Chem. 1997, 272, 16010.] Furthermore, the extent of internalization increased in an incubation time-dependent manner, and it was observed that after just 10 min, the fluorescence intensity of cells treated with FD-2 was near saturation. However, the fluorescence intensity of cells treated with FD-1 did not approach saturation until the longer time points (45 min 2 hr). Additionally, FD-1 and FD-2 exhibited differential patterns of subcellular localization, as FD-1 appeared to concentrate in the nucleus while FD-2 appeared to concentrate in the cytosol. Without wishing to be bound by theory, it is believed that the length of the spacer at the terminal generation of the dendrimer can not only control the uptake rate, [Wender, P. A.; Kreider, E.; Pelkey, E. T.; Steinman, L.; Rothbard, J. B.; VanDeusen, C. L. Org. Lett. 2005, 7, 4815.] but also regulate the subcellular localization of the molecule and its putative cargo. For instance, the uptake levels of FD-2 appeared to be generally stronger than those of FD-1 after the same incubation time at the same concentration. Therefore, the dendrimer with a hexyl spacer crosses the cell membrane faster than the molecule with an ethyl chain. On the other hand, the localization patterns can also be controlled by the length of the spacer, FD-1 with the short spacer appeared to be localized everywhere in the cell, but highly concentrated in the nucleus. However, FD-2, with its longer spacer, was observed to reside mainly in the cytosol. These translocation features of guanidinlyated dendritic scaffolds as carriers can be important for intracellular delivery of cargo molecules to specific subcellular compartments (e.g., cytosol or nucleus). For example, a translocation approach that does not saturate the nucleus can be highly attractive as it can be both less cytotoxic and could afford cytosolic-targeted cargos with greater accuracy in delivery, and therefore higher efficacy. Without wishing to be bound by theory, it is believed that the differential uptake patterns by FD-1 and FD-2 are due to the presence of a hexyl spacing chain in FD-2, resulting in a greater hydrophobicity of the entire conjugate as compared with FD-1. Additionally, the uptake of FD-1 and FD-2 conjugates by HMEC was also conducted. Entry of the two conjugates into HMEC shows a similar internalization pattern to that seen in fibroblasts.

Figure 3:
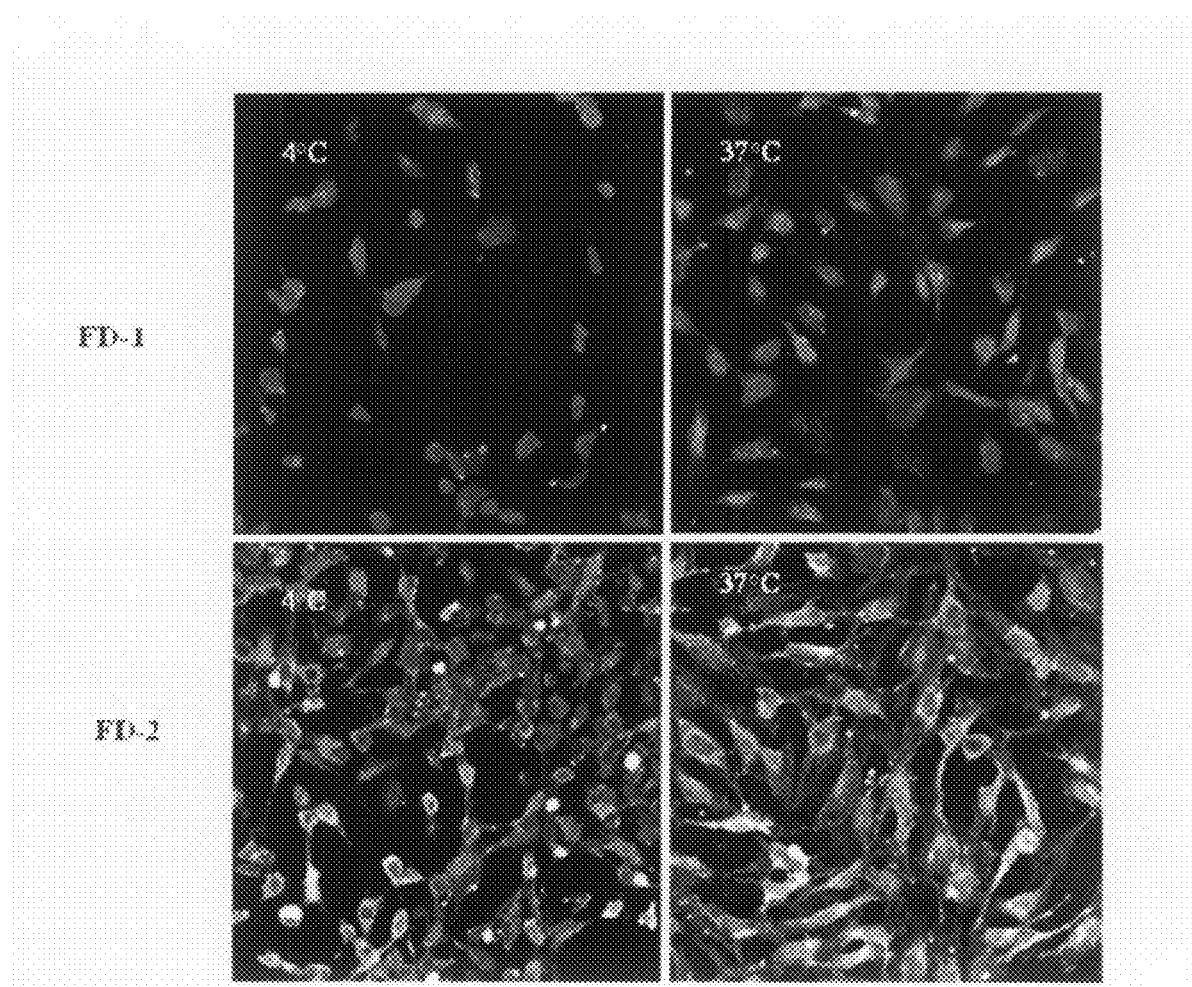
FIG. 3 shows the effect of temperature on (a) FD-1 and (b) FD-2 internalization. The human microvascular endothelial cells (HMEC) cells were incubated with conjugates (10 uM) for 2.5 min at 4° C. or at 37° C.
Figure 4:
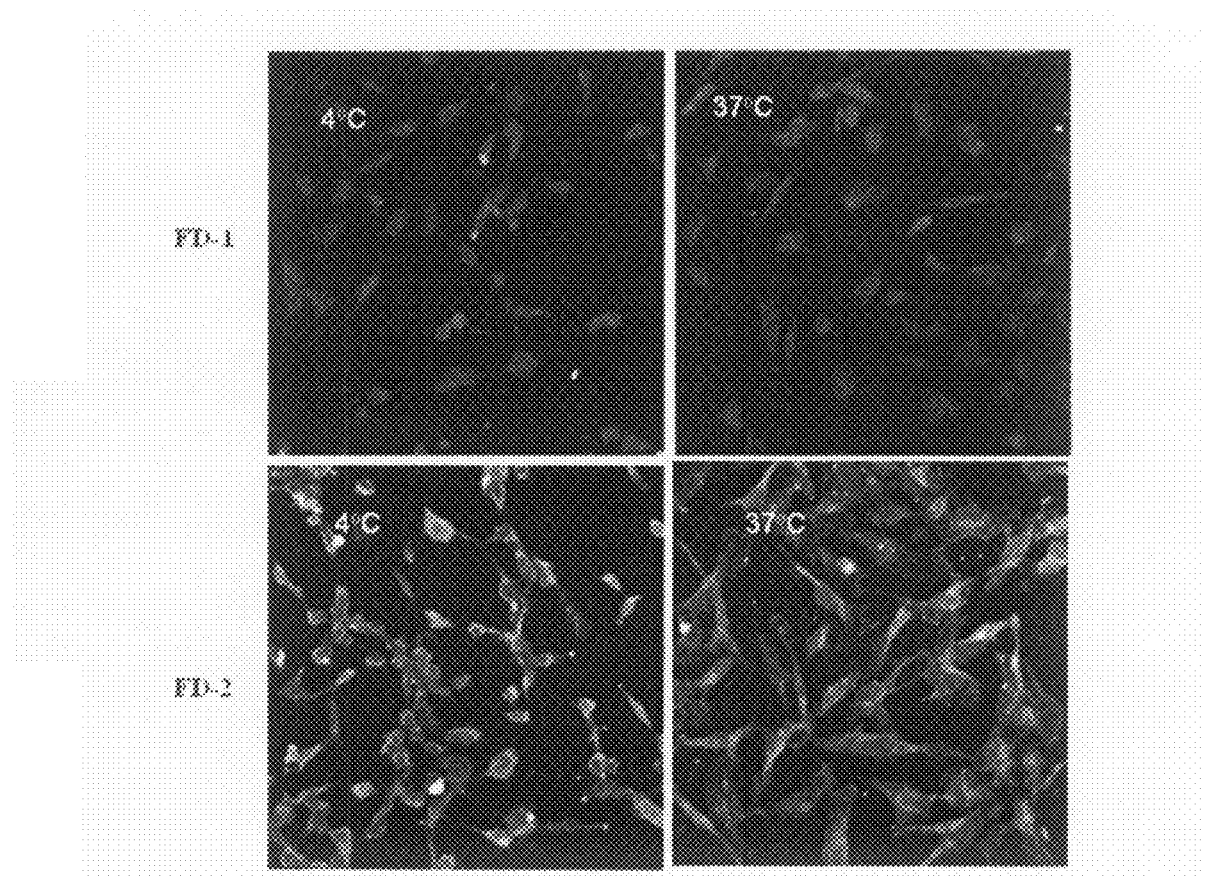
FIG. 4 shows the effect of temperature on (a) FD-1 and (b) FD-2 internalization. The HMEC cells were incubated with conjugates (1 uM) for 30 min at 4° C. or at 37° C.
Figure 5:
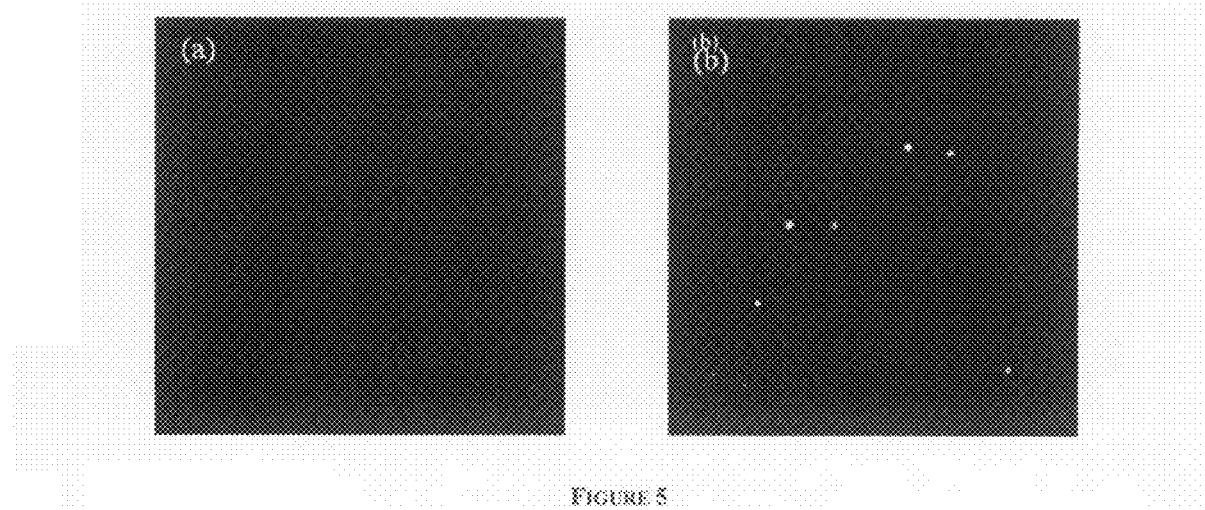
FIG. 5 shows control experiments: (a) The HMEC cells were incubated with free FITC conjugates (10 uM) for 60 min at 37° C. (b) The HMEC cells were incubated with Boc-protected guanidinylated FD-2 (10 uM) for 60 min at 37° C.

In control experiments, cells treated with free FITC and Boc-protected guanidinylated FITC-dendrimer showed no or extremely weak fluorescence, respectively. Therefore, the guanidino groups play an important role in the cell permeability of these molecules, while the length of the spacing chain determines both the differential rate of uptake and subcellular localization patterns. Although the mechanism of Tat translocation remains to be understood, it has been demonstrated that the rate of uptake is not temperature dependent. [Futaki, S.; Nakase, I.; Suzuki, T.; Youjun, Y.; Sugiura, Y. Biochemistry 2002, 41, 7925.; Vivès, E.; Brodin, P.; Lebleu, B. J. Biol. Chem. 1997, 272, 16010.] This indicates that endocytosis does not play a crucial role in the translocation process. Evaluation of the effect of temperature on the internalization of FD-1 and FD-2 indicated that the two conjugates are able to get into cells not only at 37° C., but also at 4° C., even at a lower dendrimer concentration (1 µM) (see FIGS. 3 and 4 in contrast to control experiments, as shown in FIG. 5). No significant decrease in fluorescence intensity of cells treated with FD-1 or FD-2 was observed, indicating that the uptake process does not occur via endocytosis.

11. Synthesis of Dendrimer B11

A three-neck round bottom flask was flame-dried under argon, to which nitrotriacid B3 (3.192 g, 0.0115 mmol), 1-hydrobenzotriazole (HOBt) (5.609 g, 0.0415 mol), DCC (8.560 g, 0.0415 mol) and 100 mL THF were added sequentially. After 2 hours activation, aminotriester B2 (17.216 g, 0.0415 mol) was added. The solution was stirred at room temperature for 40 h, and the crude product was purified by flash column chromatography, eluting first with hexane/ethyl acetate (10:1) and then hexane/ethyl acetate (3:2) to yield dendrimer B1 (15.91 g, 94.1%). $^1$H NMR (400 MHz, CDCl$_3$): δ= 1.44 (m, CH$_3$, 81 H), 1.95 (m, CH$_2$, 18 H), 2.21 (m, CH$_2$, 30 H), 6.20 (s, NH, 3H); $^{13}$C NMR (400 MHz, CDCl$_3$): δ=28.04, 29.74, 29.85, 31.28, 57.56, 80.69, 92.47, 170.46, 172.76.

12. Synthesis of Dendrimer B12

A solution of B11 (10.0 g, 0.0 mol) in 150 mL of absolute ethanol in the presence of 8 grams of Raney-Nickel was hydrogenated at 60 psi of hydrogen at room temperature for 24 h. The suspension was carefully filtered through Celite and removal of the solvent under reduced pressure yielded B12 (9.86 g, 98.5%). $^1$H NMR (400 MHz, CD$_3$OD): δ= 1.44 (m, CH$_3$, 81 H), 1.61 (m, CH$_2$, 6 H), 1.95 (m, CH$_2$, 12 H), 2.21 (m, CH$_2$, 30 H); $^{13}$C NMR (400 MHz, CD$_3$OD): δ=28.42, 30.24, 30.47, 32.02, 36.24, 53.53, 58.37, 81.18, 173.96, 175.39.

13. Synthesis of B25

To a room temperature stirred solution of 6-bromohexanoic acid (2.0 g, 0.0102 mol) in 7 mL of DMF was added NaN$_3$ (1.30 g, 0.020 mol). The reaction mixture was heated and stirred at 85° C. for 5 h. After DMF was removed, DCM was added to dissolve the residue. The mixture was washed with 0.1 N HCl and dried over anhydrous NaSO$_4$. Removal of the solvent gave a crude oil that was purified by flash column chromatography, eluting first with DCM and then ethyl acetate/DCM (3:7) to yield B25 (1.67 g, 69.07%). $^1$H NMR (400 MHz, MeOD): δ= 1.38-1.49 (m, CH$_2$, 2H), 1.54-1.70 (m, CH$_2$, 4 H), 2.32 (t, CH$_2$, 2 H), 3.30 (t, CH$_2$, 2 H); $^{13}$C NMR (400 MHz, MeOD): δ= 25.57, 27.32, 29.62, 34.72, 52.27, 177.38.

14. Synthesis of Dendrimer B13

To a stirred solution of B25 (1.29 g, 8.22 mmol) in anhydrous THF (50 mL) were added DCC (1.70 g, 8.22 mmol) and HOBt (1.112 g, 8.22 mmol) at room temperature. The mixture was stirred for 2 h, then dendrimer B12 (9.86 g, 6.85 mmol) was added and the resulting solution was stirred for 40 h. After filtration and removal of THF, the product was purified by flash column chromatography, eluting with hexane/ethyl acetate (1:1) to yield B13 (8.50 g, 78.53%). $^1$H NMR (400 MHz, CD$_3$OD): δ= 1.44 (m, CH$_3$, CH$_2$, 83 H), 1.95 (m, CH$_2$, 18 H), 2.21 (m, CH$_2$, 32 H), 3.30 (m, CH$_2$, 2 H); $^{13}$C NMR (400 MHz, CD$_3$OD): δ=26.47, 27.47, 28.43, 29.62, 30.35, 30.61, 32.07, 32.23, 37.56, 52.28, 58.63, 58.77, 81.54, 174.21, 175.35, 175.66.

15. Synthesis of Dendrimer B14

To a 0° C. stirred solution of nona-amine B5 (4.06 g, 2.43 mmol) in a methanol/acetonitrile (25 mL/15 mL) were added triethylamine (6.87 g, 68.0 mmol) and ethyl trifluoroacetate (9.32 g, 65.6 mmol) and the reaction mixture was stirred at 0° C. for 1 h and then at room temperature overnight. The solvent was removed in vacuo and the residue was taken up in ethyl acetate, and the resulting organic solution was washed with 1N HCl and brine and dried over anhydrous NaSO$_4$. Removal of the solvent in vacuo gave a crude solid that was purified by flash chromatography (EtOAc/Methanol gradient) to yield a solid (3.02 g, 56.3%). $^1$HNMR (400 MHz, CD$_3$OD): δ= 1.85-2.10 (m, CH$_2$, 18 H), 2.11-2.35 (m, CH$_2$, 30 H), 3.24-3.48 (m, CH$_2$, 36 H); $^{13}$C NMR (400 MHz, CD$_3$OD): δ= 31.08, 31.26, 31.75, 32.01, 39.42, 40.42, 58.93, 94.33, 111.74, 115.54, 119.33, 123.13, 158.57, 159.06, 159.55, 160.04, 173.57, 176.14. The resulting white solid (1.0 g, 0.453 mmol) was dissolved in ethanol (45 mL) and transferred into a hydrogenation vessel containing Raney-Nickel catalyst (5 g) and the suspension was stirred at 80 psi of hydrogen at 50° C. for 48 h. After filtration through Celite, the solvent was removed under reduced pressure to give a B14 as a white solid (0.964 g, 97.7%).

$^1$HNMR (400 MHz, CD$_3$OD): δ=1.61.67 (m, CH$_2$, 6 H), 1986 (m, CH$_2$, 12 H), 2.188 (m, CH$_2$, 30 H), 3.30-3.55 (m, CH$_2$, 36 H); $^{13}$C NMR (400 MHz, CD$_3$OD)
δ=31.20, 32.11, 36.17, 39.38, 40.52, 54.06, 58.80, 111.79, 115.53, 119.36, 123.10, 158.58, 159.04, 159.50, 160.11, 175.55, 176.24.

16. Synthesis of Dendrimer B..

To a stirred solution of 6-heptynoic acid (0.3022 g, 2.40 mmol) in anhydrous THF (50 mL) were added DCC (0.4952 g, 2.40 mmol) and HOBt (0.3245 g, 2.40 mmol) at room temperature. The mixture was stirred for 2 h, then dendrimer B14 (1.0432 g, 0.48 mmol) was added and the resulting solution was stirred for 40 h. After filtration and removal of THF, the product was purified by flash column chromatography, eluting with ethyl acetate/methanol gradient to yield B11 (0.620 g, 56.57%). $^1$H NMR (400 MHz, CD$_3$OD): δ=1.53 (m, CH$_2$, 2 H), 1.71 (m, CH$_2$, 3 H), 1.890-2.5 (m, CH$_2$, 50 H), 3.30 (m, CH$_2$, 36 H); $^{13}$C NMR (400 MHz, CD$_3$OD): δ = 18.81, 26.14, 29.43, 31.27, 31.80, 37.37, 39.35, 40.43, 58.83, 59.05, 69.95, 83.4, 111.74, 115.57, 119.37, 123.13, 158.55, 159.07, 159.53, 159.99, 175.60, 176.25.

17. Synthesis of Dendrimer B16

Azide dendron B13 (100 mg, 0.044 mmol) and alkyne dendron B15 (70 mg, 0.044 mmol) were dissolved in THF/H$_2$O (4:1) and DIPEA (0.017 g, 0.132 mmol, 3 equiv) followed by Cu(PPh$_3$)$_3$Br (0.0042 g, 0.0044 mmol) were added. The reaction mixture was placed in the microwave reactor (Biotage) and irradiated at 120° C. for 20 min. After completion of the reaction, THF was removed and the residue was taken up in DCM. The organic layer was washed with water once and dried over anhydrous Na$_2$SO$_4$. 1H NMR of B16 (400 MHz, CD$_3$OD): δ= 1.43 (m, CH$_3$, 81 H), 1.71 (m, CH$_2$, 8 H), 1.890-2.5 (m, CH$_2$, 96 H), 2.71 (m, CH$_2$, 2 H), 3.30 (m, CH$_2$, 36 H), 4.38 (m, CH$_2$, 2 H), 7.75 (s, 1H).

18. Synthesis of B17 and B18

The "Bow-Tie" B16 was stirred in formic acid overnight at room temperature. After the solvent was evaporated under reduced pressure, toluene was added and concentrated in vacuo to remove any residue of formic acid to give a white nonacid (100%). To a solution of the above resulting solid in DMF, HOBt and DCC were added and the solution was cooled to 0° C. N-Boc-ethylenediamine or N-Boc-hexyldiamine was added dropwise and the mixture was stirred for 48 h at room temperature, filtered and concentrated under reduced pressure. The residue was dissolved in dichloromethane and the resulting organic solution was washed sequentially with 1N HCl, water and dried over anhydrous Na₂SO₄. The solvent was evaporated under reduced pressure and the crude residue was purified by flash column chromatography to yield B17 or B18.

19. Synthesis of B19 and B20

Potassium carbonate was added to B17 or B18 in methanol/water, the mixture was stirred at room temperature for 6 h. The crude product was purified by dialysis against methanol with Spectra®Por Biotech regenerated cellulose membranes (MWCO=3500) for 24 h to give B19 or B20.

20. Synthesis of B21 and B22

The above B19 or B20 was then dissolved in 1,4-dioxane and the solution cooled 0° C., 4 M HCl in dioxane was added and stirred for 1 hr at room temperature. Removal of the solvent under reduced pressure gave a white solid. The resulting HCl salt was dissolved in methanol and the solution was cooled to 0° C. Et₃N was added, followed by N,N'-diBoc-N"-triflylguanidine and the mixture was stirred for 24 h at room temperature. After the solvent was evaporated under reduced pressure, the residue was dissolved in dichloromethane and the solution was washed with 1N HCl water, and dried over anhydrous Na₂SO₄. After removal of the solvent under reduced pressure, the crude product was purified by dialysis against methanol with Spectra®Por Biotech regenerated cellulose membranes (MWCO=3500) for 24 h to give B21 or B22.

21. Synthesis of B23 and B24

The resulting solid B21 or B22 was dissolved in 1,4-dioxane and the solution cooled to 0° C., 4 M HCl in dioxane was added and the solution stirred overnight at room temperature. The precipitate was filtered off and dried to give a crude product. The solid was re-dissolved in water and insoluble precipitate was filtered off and the filtrate was dialyzed against water with Spectra Por Biotech cellulose ester membranes (MWCO=1000) for 48 hrs and lyophilized to yield a water-soluble B23 or B24.

22. Compound Q6

3-Carboxaldehydebicyclo[4,2,0]octa-1,3,5-triene or 4-Carboxaldehydebenzocyclobutene, Q6. To a 500-mL flask was added 50 mL dry of THF, Mg turnings (2.88 g, 120 mmol), and 1,2-dibromoethane (4 drops). The reaction mixture was then heated under reflux for 15 min, 4-Bromobenzocyclobutene, 5,11 (20.0 g, 109 mmol) in 25 mL THF was added via a dropping funnel to form the Grignard reagent. After addition and rinsing the dropping funnel with 25 mL of dry THF, the reaction mixture was heated for an additional 45 min under reflux to give a green brown solution. The reaction mixture was then cooled to 0° C., DMF (15 mL, 210 mmol) was added dropwise to the solution, and the reaction mixture was heated under reflux for 15 min. The reaction mixture was poured onto 150 g of ice, acidified to pH), and neutralized with saturated NaHCO₃ solution. The crude product was extracted with ethyl acetate, the organic phase was filtered over Celite, and evaporation of the solvent gave the crude product. The product was purified by column chromatography using 10% diethyl ether/hexane as eluting solvents and was finally purified by Kugelrohr distillation (145° C., 0.5 mm) to give the aldehyde Q6 (11.7 g, 81.2%) as a colorless liquid; IR 3000-2800, 1690, 1598, 1216, 1067 and 827 cm⁻¹; ¹H NMR (400 MHz, CDCl₃) δ 9.9 (s, 1H, CHO), 7.65 (dd, 1H, J=7.4 Hz, J'=1.2 Hz, ArH), 7.50 (s, 1H, ArH), 7.14 (dd, 1H, J=7.4 Hz, J') 1.2 Hz, ArH), 3.15 (s, 4H, CH2); ¹³C NMR (100 MHz, CDCl₃) δ 192.28, 153.69, 146.57, 135.4, 130.26, 122.89, 122.81, 29.97, and 29.23. Anal. Calcd for C₉H₈O; C, 81.8; H, 6.10. Found: C, 81.7; H, 5.94.

23. Compound Q4

3-Ethenylbicyclo[4,2,0]octa-1,3,5-triene or 4-Vinylbenzocyclobutene, Q4. To a 500-mL round-bottom neck flask was added (Ph)₃PCH₃Br (24.3 g, 68.1 mmol), 110 mL of dry THF, and the solution was cooled to −78° C. n-BuLi (2.5 M in hexane, 26.4 mL, 66 mmol) was added dropwise, and the reaction mixture was allowed to warm to room temperature. The yellow-orange solution was cooled to −78° C., and the aldehyde 6 (7.16 g, 54.2 mmol), diluted in 34 mL of dry THF, was added slowly. The mixture warmed to room temperature, and stirring continued for 2 h. The reaction was treated sequentially with saturated NH₄Cl and saturated NaHCO₃ solution, and the crude product was filtered over Celite, washed with diethyl ether/hexane (1:1), and evaporated to dryness (no heat) to give the crude product. Further purification by column chromatography using 5% diethyl ether/hexane as an eluting solvent followed by Kugelrohr distillation (75° C., 1.0 mm) gave the pure styrene derivative Q4 as a colorless liquid (5.50 g, 78%); IR 2925, 1627, 1473, 989, 901, and 829 cm⁻¹; ¹H NMR (400 MHz, CDCl₃) δ 7.26 (d, 1H, J=7.4 Hz, ArH), 7.20 (s, 1H, ArH), 7.04 (d, 1H, J=7.4 Hz, ArH), 6.74 (dd, 1H, J=17.5 Hz, J'=10.8 Hz, CH), 5.70 (d, 1H, J=17.5 Hz, CH₂), 5.20 (d, 1H, J=10.8 Hz, CH2), 3.19 (s, 4H, CH₂); ¹³C NMR (100 MHz, CDCl3) ä 146.09, 145.75, 137.94, 136.69, 125.71, 122.58, 119.90, 112.38, 29.52, and 29.35. Anal. Calcd for C₁₀H₁₀; C, 92.2; H, 7.80. Found: C, 92.0; H, 8.03.

24. Random Copolymer of Q4 and Styrene, Q8

The alkoxyamine initiator, Q7 (32.5 mg, 0.1 mmol), Q12 dissolved in styrene (10.4 g, 100 mol) and 4-vinylbenzocyclobutene, Q4 (3.25 g, 25.0 mmol) were added to a glass ampule with a stir bar. After three freeze and thaw cycles the ampule was sealed under argon and heated for 6 h at 120° C. The resulting polymer was dissolved in dichloromethane and purified by precipitation into a 1:1 mixture of 2-propanol/acetone followed by reprecipitation into methanol to give Q8 as a colorless powder (12.1 g, 88%), Mw=111 000; PDI) 1.11; IR 3100-2850, 1601, 1492, 1452, 909, and 699 cm⁻¹; ¹HNMR (400 MHz, CDCl₃) δ 7.24-6.57 (m, ArH), 3.05 (br s, CH2), 1.83-1.26 (m, CH₂, CH); ¹³C NMR (100 MHz, CDCl₃) δ 145.0-146.4, 1127.9, 125.5, 121.8, 42.0-44.0, 40.4, and 29.2.

25. Random Copolymer of Q4 and N-Butylacylate, Q10

The alkoxyamine initiator Q7 (32.5 mg, 0.1 mmol) was dissolved in n-butyl acrylate (10.2 g, 72.0 mmol) and Q4 (1.04 g, 8.0 mmol) and placed in a glass ampule with a stir bar. After three freeze and thaw cycles the ampule was sealed under argon and heated for 15 h at 125° C. The resulting polymer was dissolved in dichloromethane and precipitated in MeOH/H2O (3:1) to give Q10 as a colorless gum (10.2 g, 91%), Mw=77 500; PDI) 1.12; ¹H NMR (400 MHz, CDCl₃) δ 6.83-6.63 (m, ArH), 4.10-3.83 (m, CH2, CH), 3.05 (bs, CH2), 2.22-1.01 (m, CH2, CH3).

26. Compound Q12

Methyl(2,2,5-Trimethyl-3-(benzylethoxy)-4-phenyl-3-azahexane)-poly(ethylene Glycol), Q12. NaH (0.23 g, 6.3 mmol) was slowly added to a mixture of monomethylpoly(ethylene glycol), Q14 (7.85 g, 1.57 mmol), and 18-crown-6 (10 mg) dissolved in 10 mL of THF under a constant argon flow. After 15 min, the chloromethyl-substituted alkoxyamine, 13 (1.16 g, 3.14 mmol) was added to the reaction mixture, which was subsequently heated at reflux for 16 h. After the addition of a few drops of water to neutralize the excess NaH, the reaction mixture was concentrated, dissolved in dichloromethane, filtered, and evaporated to dryness. The crude product was obtained after flash chromatography eluting with dichloromethane gradually increasing to 10% methanol/dichloromethane to give the PEG-macroinitiator, Q12, as a colorless solid (8.03 g, 89%); IR (KBr) 3439 cm$^{-1}$ (NH), 1693 cm$^{-1}$ (amide). $^1$H NMR (400 MHz, CDCl$_3$) δ 7.4-7.1 (m, ArH), 5.10 (d, CH), 4.92 (d, CH$_2$OAr), 3.65 (s, OCH$_2$), 3.41 (d, CH), 3.28 (d, CH), 2.43 (m, CH), 1.65 (d, CH$_3$), 1.52 (d, CH$_3$), 1.40 (m, CH), 1.33 (d, CH3), 1.05 (s, t-Bu), 0.89 (d, CH3), 0.80 (s, t-Bu), 0.61 (d, CH$_3$), and 0.22 (d, CH$_3$).

27. Compound Q15

Poly(ethylene glycol)-b-(styrene-co-benzocyclobutene), Q15. The poly(ethylene glycol) terminated alkoxyamine, Q12 (500 mg, 0.1 mmol) (Mn=5 000, PDI) 1.06) was dissolved in styrene (10.4 g, 100 mol) and 4-vinylbenzocyclobutene, Q4 (3.25 g, 25.0 mmol) in a glass ampule with a stir bar. After three freeze and thaw cycles the ampule was sealed under argon and heated for 6 h at 125° C. The resulting polymer was dissolved in dichloromethane and purified by precipitation into a 1:1 mixture of isopropoanol/acetone followed by reprecipitation into methanol to give Q15 as a colorless powder (10.7 g, 76.1%), Mw=89 500; PDI=1.12; $^1$H NMR (400 MHz, CDCl$_3$) δ 7.24-6.57 (m, ArH), 3.65 (s, OCH2), 3.05 (br s, CH2), 1.83-1.26 (m, CH$_2$, CH).

28. General Procedure for Nanoparticle Formation Q9

In a 500-mL three-necked flask equipped with a internal thermometer, condenser, and septum, 120 mL of benzyl ether was heated at 250° C. under argon. A solution of the benzocyclobutene (BCB)-functionalized linear polymer, Q8 (4.00 g, Mn=108000; PDI=1.15, 7.5 mol % BCB), dissolved in benzyl ether (40 mL) was added dropwise via a peristaltic pump at ca. 12.8 mL/h with vigorously stirring under argon. After addition the reaction mixture was heated for an additional 1 h, the solvent was distilled under reduced pressure, and the remaining crude product was dissolved in dichloromethane and precipitated into methanol. This gave the nanoparticles, Q9, as a colorless solid (3.76 g, 94% yield), $^1$H NMR (400 MHz, CDCl$_3$). The significant change is the disappearance of the aliphatic benzocyclobutene protons at 3.05 on formation of the cross-linked nanoparticles; all other aspects of the spectrum are similar.

29. Compound Q20

Synthesis of 5-Vinyl-1,3-dihydro-benzo(c)thiophene 2,2-dioxide, Q20. Under classical Heck reaction conditions, 5-Bromo-1,3-dihydro-benzo(c)thiophene 2,2-dioxide was transformed with PPh$_3$, Pd(OAc)$_2$, TEA, and vinyltrimethylsilane at 90° C. in DMF. The crude product was extracted with CH$_2$Cl$_2$ and concentrated. Deprotection in CH$_2$Cl$_2$/TFA gave the pure product after purification with flash chromatography (CH$_2$Cl$_2$) in high yields.

Compounds Q22 to Q26 were prepared according to the following procedures, as set forth schematically below.

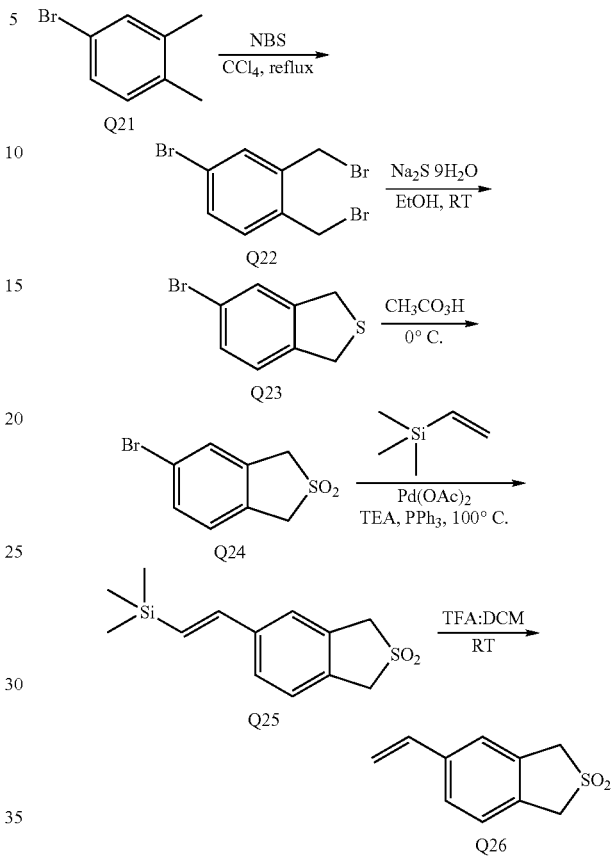

COMPOUND Q22

4-bromo-1,2-bis(bromomethyl)benzene (Q22). To a 1000 mL round bottom flask was added 4-bromo-o-xylene (21) (0.0811 mol, 15.00 g), NBS (0.0426 mol, 7.580 g), 2,2'-azobisisobutyronitrile (0.00405 mol, 0.6650 g) and 500 mL of CCl$_4$. The reaction mixture was then heated under reflux for 1 h. After this time another amount of NBS and AIBN was added and repeated over four times in total. The precipitate was filtered off from the warm reaction mixture and the filtrate concentrated. Crude material was crystallized from hexanes to form white crystals (23 g, 93%). $^1$H NMR (300 MHz, CDCl$_3$) δ 7.53 (d, 1H, ArH, J=2.0 Hz), 7.44 (dd, 1H, ArH, J=8.1 Hz, J'-2.0 Hz), 7.24 (d, 1H, ArH, J=8.10), 4.60 (d, 4H, CH$_2$, J=4.20 Hz)

31. Compound Q23

5-bromo-1,3-dihydro-2-benzo[c]thiophene (Q23). To the stirring solution of Na$_2$S.9H$_2$O (0.0502 mol, 12.043 g) in 800 mL of ethanol was added dropwise a solution of 4-bromo-1,2-bis(bromomethyl)benzene (0.0418 mol, 14.334 g) in 200 mL of ethanol in room temperature. After 20 h a cloudy white reaction mixture was filtered and concentrated down to a 200 mL volume. Then 250 mL of ethyl acetate was added and the organic solution was washed 3× with water (125 mL) and 1× with brine (125 ml). The organic phase was dried over anhydrous MgSO$_4$ and concentrated. The crude product gave a yellow oil and was used without further purification. $^1$H NMR (300 MHz, CDCl$_3$) δ 7.38 (s, 1H, ArH) ppm 7.32 (dd, 1H, J=1.8 Hz, J=8.1 Hz, ArH) ppm 7.11 (d, 1H, J=8.1 Hz, ArH) ppm 4.21 (dd, 1H, J=1.8 Hz, J=8.5 Hz)

32. Compound Q24

5-bromo-1,3-dihydro-2-benzo[c]thiophene-2,2 dioxide (Q24). The crude 5-bromo-1,3-dihydrobenzo[c]thiophene (Q21) from previous reaction 7.815 g was dissolved in 5.00 mL of glacial acetic acid and cooled in an ice bath. This suspension was added dropwise to 11 ml of cold peracetic acid cooled with an ice bath. After complete addition, the reaction was allowed to warm up to RT and a white precipitate formed over night. The reaction mixture was filtered and the precipitated washed with cold ethanol. The crude product was a light yellow precipitate and was used without any further purification. A typical yield of 3.749 g was observed for the reaction. $^1$H-NMR (300 MHz, CDCl$_3$) ppm 7.36 (dd, 1H, J=9.8 Hz, J=92.9 Hz) (m, ArH), 4.34 (d, 1H, J=13.0Hz) (d, CH$_2$). $^{13}$C-NMR (400 MHz, CDCl$_3$) ppm 133.604, 132.549, 130.559, 129.570, 127.999, 123.088, 57.017, 56.914

33. Compound Q25

5-Trimethylsilylvinyl-1,3-dihydro-benzo[c]thiophene 2,2-dioxide (Q25). A 250 mL 3-neck round bottom flask was purged with N$_2$ for 10 minutes. Compound Q23 (5 g, 20.2 mmol), vinyl trimethylsilane (10.10 g, 100.77 mmol), triethylamine (5.562 g, 54.97 mmol), triphenyl phosphine (0.433 g, 1.65 mmol), and palladium (II) acetate (0.185 g, 0.824 mmol) were then added to the flask with 50 mL of anhydrous DMF. Nitrogen was then bubbled through the mixture for 10 min. The round bottom flask was then sealed via a rubber septum and was charged with N$_2$ the mixture was yellow-orange in color. The reaction mixture heated to 100° C. and additional vinyl trimethylsilane (5.005 g, 50.39 mmol), triethylamine (2.781 g, 27.48 mmol), triphenylphospine (0.216 g, 0.824 mmol), and palladium (II) acetate (0.0925 g, 0.413 mmol) were added to the mixture followed by a N$_2$ purge of the reaction and charge of the vessel after 1 hour. After reacting a total of 2 hours, another equivalent vinyl trimethylsilane (5.005 g, 50.39 mmol), triethylamine (2.781 g, 27.48 mmol), triphenylphosphine (0.216 g, 0.824 mmol), and palladium (II) acetate (0.0925 g, 0.413 mmol) was added and the reaction mixture was again purged then charged with N$_2$ and was allowed to react a total of 18 h. The reaction mixture was removed from the oil bath and allowed to cool to room temperature. The mixture was diluted with methylene chloride, washed 3× with water (500 ml), dried over MgSO$_4$, filtered, and concentrated to give the crude product, Q25. $^1$H NMR (300 MHz, CDCl$_3$): δ 7.43-7.26 (m, 3H, ArH), 6.83 (d, 1H, CH), 6.51 (d, 1H, CH), 4.37 (s, 4H, CH$_2$), 0.16 (s, 9H, CH$_3$); $^{13}$C NMR (400 MHz, CDCl$_3$): δ 142.03, 139.20, 131.84, 131.61, 130.59, 126.95, 126.14, 123.59, 56.95, 56.86, −1.03, −1.36.

34. Compound Q26

5-vinyl-1,3-dihydro-benzo[c]thiophene 2,2-dioxide (Q26). A 60% (wt) solution of trifluoroacetic acid in methylene chloride was prepared and added to the crude product Q25. The reaction was allowed to stir for 14 h at which time it was diluted with CH$_2$Cl$_2$ and washed 3× with 500 ml water with H$_2$O. The organic phase was dried over MgSO$_4$, filtered and concentrated. The crude product was then purified by column chromatography using a gradient system of 4:1 hexanes:ethyl acetate followed by 3:2 hexanes:ethyl acetate. The pure product Q26 was isolated as a light yellow powder (0.91 g, 93.2%). 1H-NMR (300 MHz, CDCl$_3$) ppm 7.39 (d, 1H, J=8.1 Hz, ArH) ppm 7.33 (s, 1H, ArH) ppm 7.26 (d, 1H, J=8.1 Hz, ArH) ppm 6.69 (dd, 1H, J=10.9 Hz, J=17.6 Hz, =CH) ppm 5.77 (d, 1H, J=17.6 Hz, =CH$_2$) ppm 5.32 (d, 1H, J=10.9 Hz, =CH$_2$) ppm 4.35 (s, 1H, CH$_2$) $^{13}$C NMR (400 MHz, CDCl$_3$): δ 138.11, 130.14, 126.47, 125.90, 123.26, 115.21, 56.63, 56.54

35. Synthesis of Benzene Diazonium Carboxylate

Anthranilic acid (10.0 g, 72.9 mmol) and a solution of trifluoroacetic acid (60.7 mg, 0.532 mmol) in 6 mL of THF were dissolved with stirring in 73.1 mL tetrahydrofuran in a plastic beaker. The solution was cooled to 0° C. and isoamyl nitrite (16.0 mL, 119.6 mmol) added dropwise over a period of 1-2 minutes. The reaction mixture was allowed to warm to room temperature and stirred 1-1.5 h. A brick-red precipitate formed and was slowly converted to the tan product. Upon completion, the product was collected by suction filtration on a plastic Buchner funnel and washed on the funnel with cold tetrahydrofuran until the washings were colorless. The product was then washed with 1,2-dichloroethane to displace the tetrahydrofuran. The solvent-wet product was used without further purification.

36. Synthesis of Benzocyclobutenyl Acetate

In a 1000 mL round bottomed flask, benzenediazonium-2-carboxylate was dissolved with stirring in a minimal amount 1,2-dichloroethane. Vinyl acetate (40.4 mL, 437.4 mmol) was added dropwise to the solution and the reaction heated to 80° C. The reaction was refluxed for 4 hrs and yielded an orange oil which was purified via column chromatography eluting with a 1:1 dichloromethane:hexanes solvent system (0.515 g, 4.36%). $^1$H NMR (300 MHz, CDCl$_3$) δ 7.35-7.14 (m, 4H, ArH), 5.91 (d, 1H, J=4.4 Hz, CH), 3.66 (dd, 1H, J=4.6 Hz, J=14.5 Hz, CH$_2$), 3.22 (d, 1H, J=14.5 Hz, CH$_2$).

37. Hydrolysis of Benocycobutenyl Acetate

A mixture of benzocyclobutenyl acetate (0.515 g, 3.18 mmol), Na$_2$CO$_3$ (0.337 g, 3.18 mmol), methanol (2.79 mL), and water (5.58 mL) was vigorously stirred overnight. The solution was extracted with diethyl ether (3×, 200 mL) and the organic phase washed with water (3×, 400 mL) and dried with MgSO$_4$ and concentrated. The resulting orange oil was recrystallized from pentane to yield white crystals. $^1$H NMR (300 MHz, CDCl$_3$) δ 7.33-7.14 (m, 4H, ArH), 5.30 (ddd, 1H, J=1.7 Hz, J=4.4 Hz, J=8.8 Hz, CH), 3.63 (dd, 1H, J=4.4 Hz, J=14.4 Hz, CH$_2$), 3.05 (dd, 1H, J=1.3 Hz, J=14.1 Hz, CH$_2$); $^1$H NMR (400 MHz, CDCl$_3$) δ 7.33-7.14 (m, 4H, ArH), 5.30 (dd, 1H, J=4.4 Hz, J=6.6 Hz, CH), 3.63 (dd, 1H, J=4.5 Hz, J=14.3 Hz, CH$_2$), 3.05 (d, 1H, J=14.3 Hz, CH$_2$)

38. Attachment of 2-(Boc-amino)-ethyl bromine to benzocyclobutenol

Sodium hydride (143.15 mg, 3.58 mmol) was placed in a dried flask which was then sealed and charged with N$_2$. A solution of benzocyclobutenol (400 mg, 3.33 mmol) in a minimal amount of THF was added to the flask and the solution stirred at room temperature for 30 minutes. The solution was then chilled to 0° C. and a solution 2-(boc-amino)ethyl bromide (1.0 g, 4.46 mmol) in a minimal amount of THF was added dropwise to the reaction and the solution was stirred at room temperature for an hour. The precipitate was filtered off and the filtrate diluted with ether and washed with water (3×, 50 mL). The organic phase was dried and concentrated to yield an orange oil that was purified via column chromatography using a 5:2 Hex:EtOAc solvent system (0.44 g, 50.2%).

39. Deprotection of T-butyl 2-(1,2)dihydrocyclobutabenzen-1-yloxy)ehtylcarbamate In a 200 mL round bottomed flask, t-Butyl 2-(1,2-dihydrocyclobutabenzen-1-yloxyl)ethylcarbamate (275.0 mg, 1.044 mmol) was dissolved in formic acid and $CH_2Cl_2$ and allowed to stir for 48 h at room temperature. After the solvent was evaporated under reduced pressure, toluene was added and concentrated to remove any residual formic acid yielding a green oil which was purified via column chromatography using a 5:2 Hex:EtOAc solvent system to yield the product (0.023 g, 13.5%).

40. Synthesis of 1,2-Bis(trimethylsilyl)benzene

Magnesium (9.72 g, 400 mmol), hexamethylphosphoramide (HMPA) (80 mL, 460 mmol), 1,2-dichlorobenzene (14.76 g, 100 mmol), and a catalytic amount of $I_2$ were combined in a 500 mL round bottomed flask and heated to 70° C. with stirring. Chlorotrimethylsilane was added dropwise to the solution at 70° C. The solution was stirred for an additional 30 minutes and then heated to 100° C. for 48 h. After cooling, the reaction mixture was poured over ice and $NaHCO_3$. The Mg and precipitate were filtered off and the filtrate was extracted with ether (3×, 200 mL). The organic phase was washed with water (2×, 400 mL) and brine (1×, 400 mL) and dried with $Na_2SO_4$ and concentrated. The product was distilled under reduced pressure at 128-133° C. to yield a light yellow oil (12.0426 g, 54.13%). $^1$H NMR (300 MHz, $CDCl_3$) δ 7.85 (dd, 2H, J=3.4 Hz, J=5.5 Hz, ArH), 7.49 (dd, 2H, J=3.4 Hz, J=5.5 Hz, ArH), 0.55 (s, 18H, $CH_3$); $^{13}$C NMR (300 MHz, $CDCl_3$) δ 145.98, 135.17, 127.76, 1.96

41. Synthesis of (Phenyl)[2-(trimethylsilyl)phenyl]iodonium Triflate

Iodobenzene diacetate (9.66 g, 30 mmol) was dissolved in $CH_2Cl_2$ (60 mL) with stirring and the solution chilled to 0° C. Triflic acid (5.1 mL, 58 mmol) was added dropwise to the solution and the reaction mixture was stirred for 2 h. A solution of 1,2-bis(trimethylsilyl)benzene (6.67 g, 30 mmol) in $CH_2Cl_2$ (10 mL) was added at 0° C. and the reaction was allowed to stir at room temperature for 2 h. Concentration of the reaction mixture gave crystals which were triturated in ether and collected by filtration to yield white crystals (9.82 g, 65.14%). $^1$H NMR (400 MHz, $CDCl_3$) δ 8.11-7.47 (m, 9H, ArH), 0.42 (s, 9H, $CH_3$); $^{13}$C NMR (400 MHz, $CDCl_3$): δ 139.0, 138.4, 133.3, 133.2, 132.4, 132.3, 132.1, 109.6, 0.1.

42. Synthesis of T-Butyl(1-ethoxyvinyloxy)dimethysilane

To a solution of 2,2,6,6-tetramethylpiperidine (17.34 mL, 102.14 mmol) in THF (63.4 mL) under argon, 2.9 M BuLi in hexanes (34.05 mL, 98.74 mmol) was added dropwise at 0° C. The reaction was stirred for 15 min. and subsequently cooled to −78° C. t-Butyldimethylchlorosilane (TBDMSCl) (16.94 g, 112.36 mmol) in THF (25.4 mL) was added and then a solution of anhydrous ethyl acetate (8.38 mL, 85.12 mmol) in THF (57.2 mL) was slowly added over 1 h. The mixture was stirred for an additional 10 min at −78° C. and then stirred at r.t. for 1 h. The solution was then diluted with hexanes (285.9 mL), filtered through a Celite pad, and the filtrate concentrated. Distillation under vacuum at 42-50° C. gave an orange oil (g, 2.0%). $^1$H NMR (400 MHz, $CDCl_3$) δ 3.74 (q, 2H, J=7.0 Hz, $CH_2$), 3.22 (d, 1H, J=2.0 Hz, $CH_2$), 3.05 (d, 1H, J=2.0 Hz, $CH_2$), 1.29 (t, 3H, J=7.1 Hz, $CH_3$), 0.94 (s, 9H, $CH_3$), 0.17 (s, 6H, $CH_3$); $^{13}$C NMR (400 MHz, $CDCl_3$) δ 160.3, 62.4, 59.6, 24.79, 17.3, 13.5, −5.4

43. Synthesis T-Butyl(1-ethoxy-1,2-dihydrocyclobutabenzen-1-yloxy)dimethylsilane A stirring solution of (phenyl)[2-(trimethylsilyl)phenyl]iodonium triflate (1.0 g, 2.0 mmol) and t-butyl(1-ethoxyvinyloxy)dimethylsilane (1.85 g, 9.96 mmol) in $CH_2Cl_2$ (14 mL) was chilled to 0° C. $Bu_4NF$ (2.39 mL) was added dropwise to the solution and the reaction allowed to come to r.t. After 3 h., water (75 mL) was added to the reaction and the solution was extracted with EtOAc (3×, 50 mL). The organic phases were dried ($Na_2SO_4$) and concentrated to give the crude cycloadduct. $^1$H-NMR (300 MHz, $CDCl_3$) δ 0.06 (s, 6H, $CH_3$), 0.89 (s, 9H, $CH_3$), 0.97 (s, 3H, $CH_3$), 3.19 (m, 2H, $CH_2$), 4.09 (q, 2H, J=7.1 Hz, $CH_2$), 7.08 (t, 1H, J=7.7 Hz, ArH), 7.18 (d, 1H, J=2.3 Hz, ArH), 7.30 (dd, 1H, J=5.0 Hz, J=8.7 Hz, ArH), 7.67 (d, 1H, J=7.2 Hz, ArH).

44. Synthesis of Benzocyclobutenone or Cyclobutabenzen-1(2H)-one

To a solution of t-butyl(1-ethoxy-1,2-dihydrocyclobutabenzen-1-yloxy)dimethylsilane (0.56 g, 2.0 mmol) in acetonitrile (2.3 mL) was added 48-50% aq. HF (0.23 mL) at 0° C. The solution was allowed to warm to room temperature and stirred for 15 hrs. The reaction was then diluted with water and washed with ether (3×, 50 mL). The combined organic extracts were washed with brine (3×, 100 mL), dried ($Na_2SO_4$), and concentrated. This gives a brown residue that was purified via column chromatography eluting with hexanes/EtOAc (9:1). $^1$H NMR (300 MHz, $CDCl_3$) δ 3.99 (s, 2H, $CH_2$), 7.40-7.24 (m, 4H, ArH).

45. Synthesis of 1-Bromobenzocyclobutene

In a 250 mL round bottomed flask equipped with a drying tube and a condenser, a solution of cycloheptatriene (30.7 g, 300 mmol), bromoform (25.3 g, 100 mmol), anhydrous $K_2CO_3$ (15.0 g, 109 mmol), and 18-crown-6 (0.75 g) was heated with stirring at 145° C. for 9-10 h. The solution was allowed to cool and diluted with an equal volume of acetone. Silica gel (15.0 g) was added to reaction mixture and the insoluble solid residue was separated via vacuum filtration and the filter cake washed with acetone until the washings were colorless. The filtrate was concentrated and distilled to remove residual cycloheptatriene. The viscous, brown residue was precipitated into hot petroleum ether. After filtration to remove the precipitate, the filtrate was concentrated and distilled in vacuo through a Vigreaux column to give slightly impure product. Pure 1-bromobenzocyclobutene was obtained as a light yellow liquid by redistillation yield (2.95 g, 5.94%). $^1$H NMR (300 MHz, $CDCl_3$) δ 7.28 (m, 1H, ArH), 7.16 (d, 1H, J=7.0 Hz, ArH), 7.07 (d, 1H, J=6.4 Hz, ArH), 5.39 (m, 1H, CH), 3.85 (dd, 1H, J=4.4 Hz, J=14.7 Hz, $CH_2$), 3.45 (d, 1H, J=14.7 Hz, $CH_2$).

46. Synthesis of Benzocyclobutenol

To a stirred solution of mercury(II) oxide (591.3 mg, 2.73 mmol) and 35% aqueous tetrafluoroboric acid (TFBA) (999.4 mg, 5.46 mmol) in 1,4-dioxane (10.9 mL), 1-bromobenzocyclobutene (1.0 g, 5.46 mmol) was added. The reaction stirred at room temperature for 2 h and was then treated successively with NaHCO$_3$ and 3N KOH until the solution remained basic. The precipitated mercury(II) oxide was filtered off and the filtrate extracted with CH$_2$Cl$_2$ (3×300 mL), dried with anhydrous Na$_2$SO$_4$, filtered, and concentrated to yield white crystals that were purified via column chromatography using a 3:2 Hexanes:EtOAc solvent system.

47. Styrene-Polyfluorene-Styrene Triblockcopolymer a. Synthesis of Macroinitiator

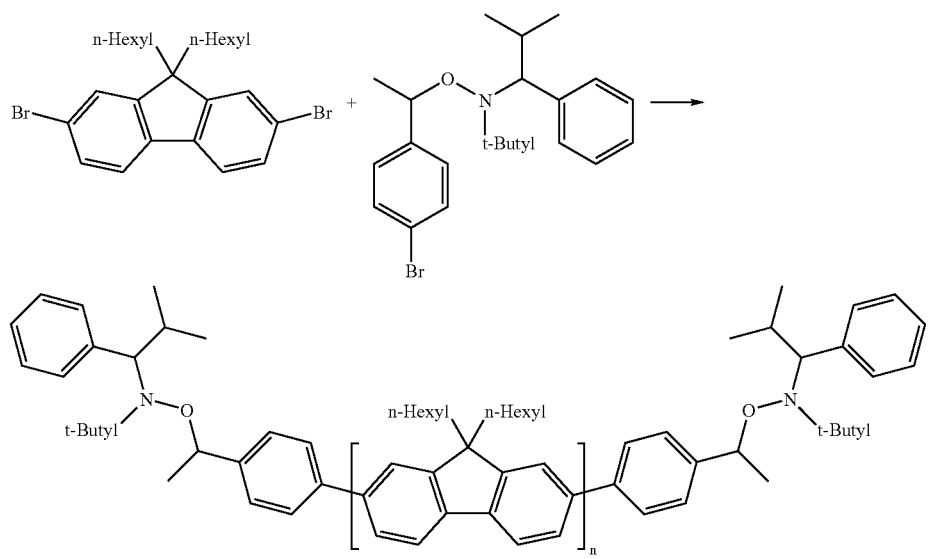

To the 3-necked round bottom flask, flushed with argon (30 min) added Nickel (5.080 mmol, 1.4000 g), 2,2'-bipirydyl (5.800 mmol, 0.9000 g), dry toluene (10 mL), 1,5-cyclooctadiene (0.5 mL), and dry DMF (12 mL). The mixture was heated to 80° C. under argon. After 30 minutes, brominated alkoxyamine initiator (0.7750 mmol, 0.3134 g) and 2,7-dibromo-9,9'-di-n-hexylfluorene (2.250 mmol, 1.1080 g) dissolved in dry toluene (13 mL) via syringe. The mixture stirred in 80° C. for 24 hours in the dark. After 24 hours, hot solution precipitated into 600 mL of solution of HCl$_{(conc)}$:acetone:methanol in ratio 1:1:1. The resulting dark brown precipitate was then filtered, dissolved in dichloromethane, concentrated in vacuo and reprecipitated with 200 mL solution of acetone:methanol, 1:1.

b. Synthesis of A-B-A Copolymer with 10% Crosslinker

Macromolecular initiator (M=3000, n=0.060 mmol, 180 mg), styrene (90 eq per chain end, 9.72 mmol, 1.0123 g), and crosslinker (5-Vinyl-1,3-dihydro-benzo[c]thiophene 2,2-dioxide) (10%, 1.08 mmol, 0.2098 g) were dissolved in 0.5 mL of chlorobenzene in 10 mL ampule. The ampule was degassed, sealed, and heated at 124° C. for 7-10 hours. After this time, the polymer was precipitated from methanol. The resulting brown precipitate was filtered, washed with methanol, and dried.

c. Intramolecular Chain Collapse Procedure for A-B-A 0.300 g of polymer was dissolved in 50 mL of benzyl ether. The solution of polymer was added dropwise 12.4 ml/hr to benzyl ether in 260° C. under nitrogen. After adding all of the polymer, the reaction was cooled down, and the benzyl ether was distilled from the reaction mixture, and the residue was precipitated from methanol.

48. Synthesis of N-Boc-N-TFA-Ethylenediamine

To a solution of N-boc-ethylenediamine (5.0 g, 31.2 mmol) in 20 mL THF, ethyl trifluoroacetate (3.72 mL, 31.2 mmol) was added dropwise and the reaction stirred overnight. The reaction solution was concentrated to yield a white crystalline product (8.0 g, 100%). $^1$HNMR (400 MHz, CDCl$_3$) δ 1.44 (s, 9H, CH$_3$), 3.37 (dd, 2H, J=5.4 Hz, J=10.2 Hz, CH$_2$), 3.46 (dd, 2H, J=5.1 Hz, J=10.4 Hz, CH$_2$), 5.01 (s, 1H, NH), 7.85 (s, 1 H, NH); $^{13}$C NMR (400 MHz, CDCl$_3$) δ 28.2, 39.1, 42.2, 80.6, 140.6, 151.2, 157.7.

49. Boc Deprotection of N-Boc-N-TFA-Ethylenediamine

N-Boc-N-Tfa-ethylenediamine (8.0 g, 31.5 mmol) was dissolved in 50 mL formic acid and stirred for 14 h at r.t After the solvent was evaporated under reduced pressure, toluene was added and concentrated to remove any residual formic acid, yielding an orange oil (4.90 g, 99.7%). $^1$H NMR (400 MHz, MeOD) δ 2.31 (s, 2H, NH$_2$), 3.15 (t, 2 H, J=6.1 Hz, CH$_2$), 3.61 (t, 2H, J=6.1 Hz, CH$_2$), 8.35 (s, 1H, NH); $^{13}$C NMR (400 MHz, MeOD) δ 38.5, 39.7, 113.1, 115.9, 118.8, 121.6, 159.7, 160.1.

50. Attachment of N-TFA-Ethylenediamine

The deprotected nanoparticles (77 mg, 0.00194 mmol) in DriSolv DMF (9.0 mL) were stirred under argon at 0° C. with N-methylmorpholine (6.9 mg, 0.0680 mmol) followed by dropwise addition of isobutyl chloroformate (10.2 mg, 0.0748 mmol) in DMF (0.5 mL). After 1.5 h, a solution of N-Tfa-ethylenediamine (10.6 mg, 0.0680 mmol) was added dropwise. The reaction was allowed to warm to room temperature and stirred overnight. After removal of DMF in vacuo, the product was dissolved in methanol and dialyzed against methanol with SnakeSkin® Pleated Dialysis Tubing (MWCO=10,000).

51. Deprotection of Mal-dPeg™₄-T-Boc-Hydrazide

In a 100 mL round bottomed flask, MAL-dPeg™₄-t-boc-hydrazide (8.8 mg, 135.0 nmol) was dissolved in 10.0 mL of formic acid and stirred over night at room temperature. After the solvent was evaporated under reduced pressure, toluene was added and concentrated to remove any residual formic acid to give MAL-dPeg™₄-hydrazide (58.1 mg, 100%).

52. Attachment of Mal-dPeg™₄-Hydrazide

The deprotected nanoparticles (77.5 mg, 0.00186 mmol) in DriSolv DMF (9.0 mL) were stirred under argon at 0° C. with N-methylmorpholine (1.5 mg, 0.0149 mmol) followed by dropwise addition of isobutyl chloroformate (2.2 mg, 0.0164 mmol) in DMF (0.1 mL). After 1.5 h, a solution of MAL-dPeg™₄—hydrazide (8.8 mg, mol) was added dropwise. The reaction was allowed to warm to room temperature and stirred overnight. After removal of DMF in vacuo, the product was dissolved in methanol and dialyzed against methanol with SnakeSkin® Pleated Dialysis Tubing (MWCO=10,000).

53. Attachment of Disulfide Linker to Boc-Protected Hexyl Molecular Transporter A solution of boc-protected hexyl molecular transporter (500.0 mg, 0.13 mmol), 3-(pyridine-2-yl disulfanyl)propanoic acid (269.5 mg, 1.25 mmol), 1-hydroxybenzotriazole (HOBt) (169.0 mg, 1.25 mmol), triethylamine (TEA) (126.7 mg, 1.25 mmol), N-(3-dimethylaminopropyl)-N'-ethylcarbodiimide hydrochloride (EDC HCl) (240.0 mg, 1.25 mmol) in 10 mL DriSolv DMF was stirred for 48 h. The DMF was removed under vacuum and the resulting brown oil purified via column chromatography eluting with a 2-10% methanol in dichloromethane gradient system (160.5 mg, 30.6%). $^1$H NMR (300 MHz, MeOD) δ 1.33-1.47 (m, 246H, $CH_2$, $CH_3$), 2.03 (d, 48H, J=65.3 Hz, $CH_2$), 3.15 (td, 30H, J=6.3 Hz, J=12.7 Hz, $CH_2$), 3.29 (m, 45H, $CH_2$), 7.42 (m, 1H, ArH), 7.67 (d, 1 H, J=8.2 Hz, ArH), 7.79 (d, 1H, J=8.1 Hz, ArH), 8.02 (s, 1H, ArH).

54. Cleavage of Disulfide Bridge on Molecular Transporter

A solution of the disulfide linker hexyl molecular transporter (118.2 mg, 2.82*10⁻⁵ mol) in DriSolv DMF (2.88 mL) was stirred under argon. A solution of DL-dithiothreitol (339.5 mg, 2.2*10⁻³ mol) in DMF (71.4 mL) was added dropwise to transporter and the reaction proceeded for 2 h at room temperature. After removal of DMF in vacuo, the reaction was purified using a Sephadex LH-20 column, eluting with DMF and concentrating the fractions in vacuo again.

55. Attachment of Molecular Transporter to Nanoparticles

The nanoparticles (77.5 mg, 1.76*10⁻⁶ mol) in DriSolv DMF (mL) were stirred under argon. The free thiol molecular transporter in DMF ## was added dropwise followed by the addition of a catalytic amount of N-methylmorpholine. After removal of DMF in vacuo, the product was dissolved in methanol and dialyzed against a 1:1 methanol:water solution, eventually dialyzing against pure methanol with SnakeSkin® Pleated Dialysis Tubing (MWCO=10,000). NMR

56. Deprotection of Trifluoroacetyl Protected Amines on Modified Particles

The nanoparticles (142.0 mg, xmol) were dissolved in a 10% $K_2CO_3$ solution of 5:3 methanol:water. Methanol was added as needed to completely dissolve the particles. The reaction proceeded overnight at room temperature. The reaction was purified by dialysis with SnakeSkin® Pleated Dialysis Tubing (MWCO=10 000) against a 5:3 methanol:water solution, eventually dialyzing against pure methanol. NMR

57. Attachment of FITC

Nanoparticles (30.0 mg, 4.75*10⁻⁷ mol) in DriSolv DMF (1.0 mL) were stirred under argon. A solution of FITC (2.8 mg, 7.13*10⁻⁶ mol) in DriSolv DMF (1.0 mL) was added dropwise and the reaction chilled to 0° C. Triethylamine (1.14 μL, 8.17*10⁻⁶ mol) was added to the solution and the reaction proceeded in the dark, overnight at room temperature.

58. Capping of the Remaining Amines

Upon completion of the FITC addition to the nanoparticles, a solution of N-acetoxysuccinimide (47.1 mg, 3.00*10⁻⁴ mol) in DriSolv DMF (1.0 mL) was added to the reaction solution. The reaction was allowed to proceed for 3 h at RT. After removal of DMF in vacuo, the product was dissolved in methanol and dialyzed against methanol with SnakeSkin® Pleated Dialysis Tubing (MWCO=10,000). NMR

59. Boc Deprotection of Modified Nanoparticles

Modified nanoparticles were dissolved in anhydrous 1,4-dioxane (10 mL) and chilled to 0° C. A solution of 4 M HCl in 1,4-dioxane (10 mL) was added dropwise to the stirring nanoparticles and the reaction was allowed to proceed overnight at room temperature The nanoparticle solution was diluted to three times the original volume with water and dialyzed against water with SnakeSkin® Pleated Dialysis Tubing (MWCO=10,000). Upon completion of dialysis, the aqueous solution was lyophilized to yield a yellow solid. NMR

60. $G_{13}$ Peptide Attachment to Multifunctional Nanoparticle

A solution of $G_{13}$ peptide (1.2 mg, 8.22*10⁻⁷ mol) in a solution of DriSolv DMF (1.0 mL) was added to a solution of MFNP (1.5 mg, 2.28*10⁻⁸ mol) in DriSolv DMF (0.75 mL) and allowed to stir overnight. The reaction was then diluted with water and dialyzed against water with SnakeSkin® Pleated Dialysis Tubing (MWCO=10,000). Upon completion of dialysis, the aqueous solution was lyophilized to yield a light yellow solid.

61. $G_{IR}$ Peptide Attachment to Multifunctional Nanoparticle

A solution of GiR peptide (1.2 mg, 8.22*10⁻⁷ mol) in a solution of DriSolv DMF (0.5 mL) was added to a solution of MFNP (1.5 mg, 2.28*10⁻⁸ mol) in DriSolv DMF (0.75 mL) and allowed to stir overnight. The reaction was then diluted with water and dialyzed against water with SnakeSkin® Pleated Dialysis Tubing (MWCO=10,000). Upon completion of dialysis, the aqueous solution was lyophilized to yield a light yellow solid.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having the structure:

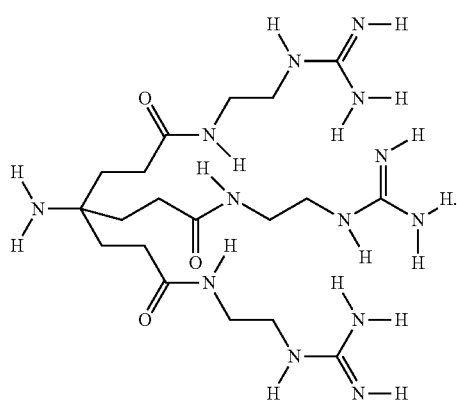

2. A compound having the structure:

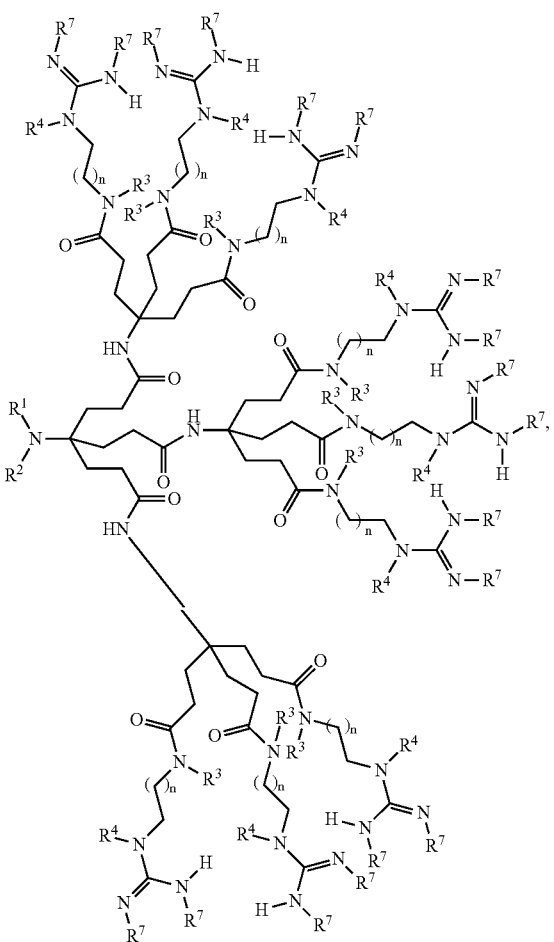

wherein n is 5;
wherein $R^1$ and $R^2$ are, independently, hydrogen, alkyl, a luminescent group, a biologically-active group, a pharmaceutically-active group, a moiety having a structure:

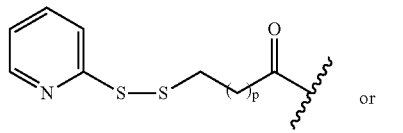

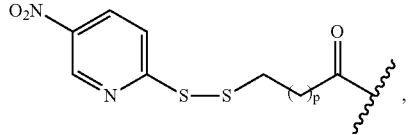

wherein p is zero or a positive integer;
a moiety having a structure:

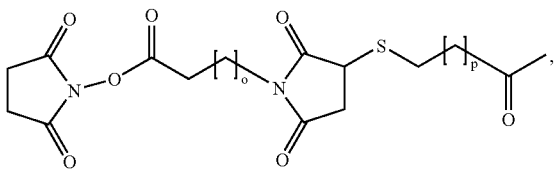

wherein o and p are, independently, zero or a positive integer;
a moiety having a structure:

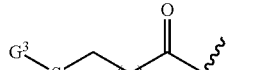

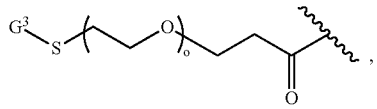

wherein o and p are, independently, zero or a positive integer, and wherein $G^3$ is
an thiol-protecting group;
a linking moiety of the structure:

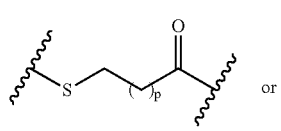

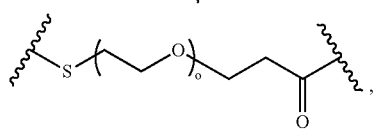

wherein o and p are, independently, zero or a positive integer, linked to a payload moiety; or
$R^1$, $R^2$, and the intermediate nitrogen form a nitro group; or
$R^1$, $R^2$, and the intermediate nitrogen form an azide group; or
$R^1$, $R^2$, and the intermediate nitrogen form an amide group; and
wherein all of $R^3$ and $R^4$ are hydrogen
wherein each $R^7$ is independently hydrogen or alkyloxycarbonyl.

3. A pharmaceutical composition comprising the compound of claim 1 and a pharmaceutically acceptable carrier for administration in a mammal.

4. A pharmaceutical composition comprising the compound of claim 2 and a pharmaceutically acceptable carrier for administration in a mammal.

5. The compound of claim 2, wherein $R^1$ is hydrogen, and wherein $R^2$ comprises a linking moiety of the structure:

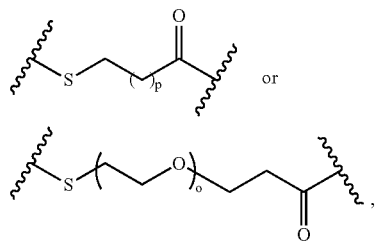

wherein o and p are, independently, zero or a positive integer;
linked to a payload moiety.

6. The compound of claim 5, wherein the payload moiety is a luminescent group, a biologically-active group, or a pharmaceutically-active group.

7. The compound of claim 2, wherein all of $R^7$ are hydrogen.

8. The compound of claim 2, wherein $R^1$, $R^2$, and the intermediate nitrogen form a luminescent group comprising the structure:

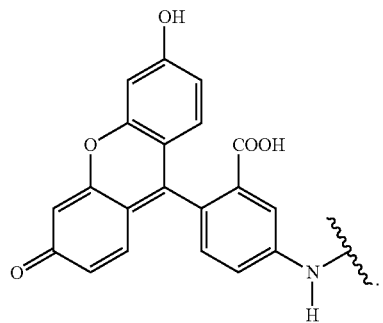 [SMILES: *Nc1ccc(-c2c3ccc(=O)cc-3oc3cc(O)ccc23)c(C(=O)O)c1]

9. The compound of claim 2, wherein $R^1$ is hydrogen, and wherein $R^2$ is a luminescent group selected from a dansyl group, a coumarin group, a fluorescein isothiocyanate (FITC) group, a 1,4,7,10-tetraazacyclododecane-1,4,7,10-tetraacetic acid (DOTA) group, a catechol group, and a diethylene triamine pentaacetic acid (DTPA) group.

10. The compound of claim 2, wherein $R^1$ is hydrogen, and wherein $R^2$ is a biologically-active group selected from an oligonucleotide, a plasmid DNA, a protein, an immunoglobulin, an antisense oligoDNA, a peptide nucleic acid (PNA), and a peptide.

11. The compound of claim 2, wherein $R^1$ is hydrogen, and wherein $R^2$ is a biologically-active group.

12. The compound of claim 2, wherein $R^1$ is hydrogen, and wherein $R^2$ is a pharmaceutically-active group selected from a drug, a protein, a peptide, a hydrogel, a dendrimer, and a hyperbranched polymeric structure.

13. The compound of claim 2, wherein $R^1$ is hydrogen, and wherein $R^2$ is a pharmaceutically-active group.

14. A compound having the structure:

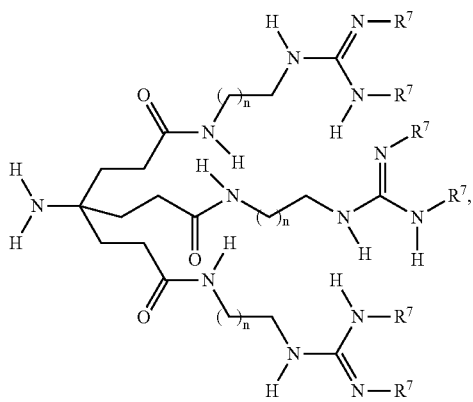

wherein n is 1 or 5; and
wherein each $R^7$ is independently hydrogen or alkyloxycarbonyl.

15. The compound of claim 11, wherein n is 5, and wherein all of $R^7$ are hydrogen.

* * * * *